United States Patent
Farrell et al.

(10) Patent No.: US 10,143,791 B2
(45) Date of Patent: Dec. 4, 2018

(54) MEDICAL FLUID PUMPING SYSTEMS AND RELATED DEVICES AND METHODS

(71) Applicant: Fresenius Medical Care Holdings, Inc., Waltham, MA (US)

(72) Inventors: Sean Farrell, Fresno, CA (US); Tri Ly, Dublin, CA (US); Gurpreet Singh, Antioch, CA (US); Kulwinder S. Plahey, Martinez, CA (US); DeLoy Lindley, Ogden, UT (US); Ignacio Serrato, Edinburg, TX (US); Venugopal Raghavendra Ghatikar, Salt Lake City, UT (US); Michael David Young, Antioch, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 458 days.

(21) Appl. No.: 14/870,926

(22) Filed: Sep. 30, 2015

(65) Prior Publication Data
US 2016/0015882 A1 Jan. 21, 2016

Related U.S. Application Data

(63) Continuation of application No. 13/442,184, filed on Apr. 9, 2012, now Pat. No. 9,180,240.
(Continued)

(51) Int. Cl.
*A61M 1/28* (2006.01)
*F04B 43/02* (2006.01)
(Continued)

(52) U.S. Cl.
CPC .............. *A61M 1/28* (2013.01); *F04B 43/02* (2013.01); *F04B 43/026* (2013.01);
(Continued)

(58) Field of Classification Search
CPC ...... F04B 43/02; F04B 43/025; F04B 43/026; A61M 1/28; A61M 1/1037; A61M 1/1046;
(Continued)

(56) References Cited

U.S. PATENT DOCUMENTS

| 329,773 A | 11/1885 | Perry |
|---|---|---|
| 2,383,193 A | 8/1945 | Herbert |

(Continued)

FOREIGN PATENT DOCUMENTS

| DE | 2628238 | 1/1978 |
|---|---|---|
| DE | 2827648 | 1/1979 |

(Continued)

OTHER PUBLICATIONS

Gambro®, "DEHP-free cartridge blood sets," © Nov. 2004, Gambro, Inc., Lakewood, CO, 4 pp.
(Continued)

*Primary Examiner* — Bradley J Osinski
*Assistant Examiner* — Nilay Shah
(74) *Attorney, Agent, or Firm* — Fish & Richardson P.C.

(57) ABSTRACT

This disclosure relates to medical fluid pumping systems and related devices and methods. In some aspects, a medical fluid pumping system includes a medical fluid pumping machine including a piston head that can be linearly displaced and a medical fluid cassette that can be secured to the medical fluid pumping machine. The medical fluid cassette includes a fastening member attached to a region of a flexible membrane overlying a fluid pump chamber, and the piston head is configured to be mechanically connected to the fastening member of the cassette.

20 Claims, 24 Drawing Sheets

Related U.S. Application Data

(60) Provisional application No. 61/477,742, filed on Apr. 21, 2011.

(51) Int. Cl.
*A61M 1/14* (2006.01)
*A61M 5/145* (2006.01)
*A61M 5/142* (2006.01)
*A61M 1/10* (2006.01)

(52) U.S. Cl.
CPC ......... *A61M 1/1006* (2014.02); *A61M 1/1037* (2013.01); *A61M 1/1046* (2013.01); *A61M 1/1081* (2013.01); *A61M 1/14* (2013.01); *A61M 5/1452* (2013.01); *A61M 5/14212* (2013.01); *A61M 5/14216* (2013.01); *A61M 2205/121* (2013.01)

(58) Field of Classification Search
CPC .... A61M 1/14; A61M 1/16; A61M 2205/121; A61M 2205/12; A61M 5/14212; A61M 5/14216; A61M 5/145; A61M 5/1452; A61M 5/31511; A61M 5/31515
See application file for complete search history.

(56) References Cited

U.S. PATENT DOCUMENTS

| | | | |
|---|---|---|---|
| 2,453,590 | A | 11/1948 | Poux |
| 2,529,028 | A | 11/1950 | Landon |
| 2,658,526 | A | 11/1953 | Porter |
| 2,711,134 | A | 6/1955 | Hughes |
| 2,755,745 | A | 7/1956 | Lewis |
| 2,871,795 | A | 2/1959 | Smith |
| 2,886,281 | A | 5/1959 | Canalizo |
| 3,083,943 | A | 4/1963 | Stewart, Jr. et al. |
| 3,323,786 | A | 6/1967 | Boschi |
| 3,556,465 | A | 1/1971 | Little |
| 3,671,814 | A | 6/1972 | Dick |
| 3,689,025 | A | 9/1972 | Kiser et al. |
| 3,741,687 | A | 6/1973 | Nystroem |
| 3,777,625 | A | 12/1973 | Andres |
| 3,781,141 | A | 12/1973 | Schall |
| 3,880,053 | A | 4/1975 | Trechsel et al. |
| 3,927,955 | A | 12/1975 | Spinosa et al. |
| 3,966,358 | A | 6/1976 | Heimes et al. |
| 3,985,135 | A | 10/1976 | Carpenter et al. |
| 4,026,669 | A | 5/1977 | Leonard et al. |
| 4,047,844 | A | 9/1977 | Robinson |
| 4,050,859 | A | 9/1977 | Vork |
| 4,091,812 | A | 5/1978 | Helixon et al. |
| 4,121,584 | A | 10/1978 | Turner et al. |
| 4,152,098 | A | 5/1979 | Moody et al. |
| 4,158,530 | A | 6/1979 | Bernstein |
| 4,178,940 | A | 12/1979 | Au |
| 4,273,121 | A | 6/1981 | Jassawalla |
| 4,303,376 | A | 12/1981 | Siekmann |
| 4,304,260 | A | 12/1981 | Turner et al. |
| 4,312,344 | A * | 1/1982 | Nilson ................ A61M 5/2425 604/212 |
| 4,322,201 | A | 3/1982 | Archibald |
| 4,333,452 | A | 6/1982 | Au |
| 4,370,983 | A | 2/1983 | Lichtenstein |
| 4,382,753 | A | 5/1983 | Archibald |
| 4,410,322 | A | 10/1983 | Archibald |
| 4,412,553 | A | 11/1983 | Kopp et al. |
| 4,436,620 | A | 3/1984 | Bellotti et al. |
| 4,453,932 | A | 6/1984 | Pastrone |
| 4,479,760 | A | 10/1984 | Bilstad et al. |
| 4,479,761 | A | 10/1984 | Bilstad et al. |
| 4,479,762 | A | 10/1984 | Bilstad et al. |
| 4,490,621 | A | 12/1984 | Watabe et al. |
| 4,536,201 | A | 8/1985 | Brorsson et al. |
| 4,558,715 | A | 12/1985 | Walton et al. |
| 4,569,378 | A | 2/1986 | Bergandy |
| 4,583,920 | A | 4/1986 | Lindner |
| 4,597,412 | A | 7/1986 | Stark |
| 4,610,605 | A | 9/1986 | Hartley |
| 4,623,328 | A | 11/1986 | Hartranft |
| 4,628,499 | A | 12/1986 | Hammett |
| 4,639,245 | A | 1/1987 | Pastrone et al. |
| 4,643,713 | A | 2/1987 | Viitala |
| 4,657,490 | A | 4/1987 | Abbott |
| 4,662,598 | A | 5/1987 | Weingarten |
| 4,662,906 | A | 5/1987 | Matkovich et al. |
| 4,676,467 | A | 6/1987 | Palsulich |
| 4,690,621 | A | 9/1987 | Swain |
| 4,703,913 | A | 11/1987 | Hunkapiller |
| 4,705,259 | A | 11/1987 | Dolhen et al. |
| 4,710,166 | A | 12/1987 | Thompson et al. |
| 4,735,558 | A | 4/1988 | Kienholz et al. |
| 4,778,451 | A | 10/1988 | Kamen |
| 4,786,240 | A | 11/1988 | Koroly et al. |
| 4,808,161 | A | 2/1989 | Kamen |
| 4,826,482 | A | 5/1989 | Kamen |
| 4,840,542 | A | 6/1989 | Abbott |
| 4,842,584 | A | 6/1989 | Pastrone |
| 4,846,636 | A | 7/1989 | Danby et al. |
| 4,850,980 | A | 7/1989 | Lentz et al. |
| 4,858,883 | A | 8/1989 | Webster |
| 4,902,282 | A | 2/1990 | Bellotti et al. |
| 4,906,260 | A | 3/1990 | Emheiser et al. |
| 4,927,411 | A | 5/1990 | Pastrone et al. |
| 4,950,134 | A | 8/1990 | Bailey et al. |
| 4,974,754 | A | 12/1990 | Wirz |
| 4,976,162 | A | 12/1990 | Kamen |
| 4,995,864 | A | 2/1991 | Bartholomew et al. |
| 4,997,464 | A | 3/1991 | Kopf |
| 5,002,471 | A | 3/1991 | Perlov |
| 5,006,050 | A | 4/1991 | Cooke et al. |
| 5,011,380 | A | 4/1991 | Kovacs et al. |
| 5,036,886 | A | 8/1991 | Olsen et al. |
| 5,061,236 | A | 10/1991 | Sutherland et al. |
| 5,088,515 | A | 2/1992 | Kamen |
| 5,098,262 | A | 3/1992 | Wecker et al. |
| 5,100,380 | A | 3/1992 | Epstein |
| 5,100,699 | A | 3/1992 | Roeser |
| 5,116,021 | A | 5/1992 | Faust et al. |
| 5,116,316 | A | 5/1992 | Sertic et al. |
| 5,146,713 | A | 9/1992 | Grafius |
| 5,151,019 | A | 9/1992 | Danby et al. |
| 5,167,837 | A | 12/1992 | Snodgrass et al. |
| 5,171,029 | A | 12/1992 | Maxwell et al. |
| 5,178,182 | A | 1/1993 | Kamen |
| 5,193,990 | A | 3/1993 | Kamen et al. |
| 5,211,201 | A | 5/1993 | Kamen et al. |
| 5,238,003 | A | 8/1993 | Baidwan et al. |
| 5,241,985 | A | 9/1993 | Faust et al. |
| 5,247,434 | A | 9/1993 | Peterson et al. |
| 5,249,932 | A | 10/1993 | Van Bork |
| 5,252,044 | A | 10/1993 | Raines et al. |
| 5,259,352 | A | 11/1993 | Gerhardy et al. |
| 5,267,956 | A | 12/1993 | Beuchat |
| 5,279,556 | A | 1/1994 | Goi et al. |
| 5,302,093 | A | 4/1994 | Owens et al. |
| 5,324,422 | A | 6/1994 | Colleran et al. |
| 5,330,425 | A | 7/1994 | Utterberg |
| 5,342,182 | A | 8/1994 | Montoya et al. |
| 5,344,292 | A | 9/1994 | Rabenau et al. |
| 5,350,357 | A | 9/1994 | Kamen et al. |
| D351,470 | S | 10/1994 | Scherer et al. |
| 5,353,837 | A | 10/1994 | Faust |
| 5,378,126 | A | 1/1995 | Abrahamson et al. |
| 5,395,351 | A | 3/1995 | Munsch |
| 5,413,626 | A | 5/1995 | Bartsch |
| 5,415,528 | A | 5/1995 | Ogden et al. |
| 5,421,208 | A | 6/1995 | Packard et al. |
| 5,421,823 | A | 6/1995 | Kamen et al. |
| 5,427,509 | A | 6/1995 | Chapman et al. |
| 5,431,626 | A | 7/1995 | Bryant et al. |
| 5,431,627 | A | 7/1995 | Pastrone et al. |
| 5,431,634 | A | 7/1995 | Brown |
| 5,438,510 | A | 8/1995 | Bryant et al. |

(56) References Cited

U.S. PATENT DOCUMENTS

| | | |
|---|---|---|
| 5,441,636 A | 8/1995 | Chevallet et al. |
| 5,445,506 A | 8/1995 | Afflerbaugh et al. |
| 5,447,286 A | 9/1995 | Kamen et al. |
| 5,462,416 A | 10/1995 | Dennehey et al. |
| 5,462,417 A | 10/1995 | Chapman |
| 5,474,683 A | 12/1995 | Bryant et al. |
| 5,478,211 A | 12/1995 | Dominiak et al. |
| 5,480,294 A | 1/1996 | Di Perna et al. |
| 5,482,438 A | 1/1996 | Anderson et al. |
| 5,482,440 A | 1/1996 | Dennehey et al. |
| 5,482,446 A | 1/1996 | Williamson et al. |
| 5,484,239 A | 1/1996 | Chapman et al. |
| 5,486,286 A | 1/1996 | Peterson et al. |
| 5,514,069 A | 5/1996 | Brown et al. |
| 5,538,405 A | 7/1996 | Patno et al. |
| 5,540,568 A | 7/1996 | Rosen et al. |
| 5,547,453 A | 8/1996 | Di Perna |
| 5,551,850 A | 9/1996 | Williamson et al. |
| 5,551,941 A | 9/1996 | Howell |
| 5,551,942 A | 9/1996 | Brown et al. |
| 5,554,013 A | 9/1996 | Owens et al. |
| 5,570,716 A | 11/1996 | Kamen et al. |
| 5,573,385 A | 11/1996 | Chevallier |
| 5,578,070 A | 11/1996 | Utterberg |
| 5,586,868 A | 12/1996 | Lawless |
| 5,588,816 A | 12/1996 | Abbott et al. |
| 5,593,290 A | 1/1997 | Greisch et al. |
| 5,599,174 A | 2/1997 | Cook et al. |
| 5,609,572 A | 3/1997 | Lang |
| 5,614,677 A | 3/1997 | Wamsiedler et al. |
| 5,624,409 A | 4/1997 | Seale |
| 5,628,908 A | 5/1997 | Kamen et al. |
| 5,630,710 A | 5/1997 | Tune et al. |
| 5,634,391 A | 6/1997 | Eady |
| 5,634,896 A | 6/1997 | Bryant et al. |
| 5,640,995 A | 6/1997 | Packard et al. |
| 5,641,405 A | 6/1997 | Keshaviah et al. |
| 5,641,892 A | 6/1997 | Larkins et al. |
| 5,643,205 A | 7/1997 | Utterberg |
| 5,645,531 A | 7/1997 | Thompson et al. |
| 5,658,133 A | 8/1997 | Anderson et al. |
| 5,669,764 A | 9/1997 | Behringer et al. |
| 5,690,602 A | 11/1997 | Brown et al. |
| D390,654 S | 2/1998 | Alsberg et al. |
| 5,713,865 A | 2/1998 | Manning et al. |
| 5,713,888 A | 2/1998 | Neuenfeldt et al. |
| 5,718,567 A | 2/1998 | Rapp et al. |
| 5,741,125 A | 4/1998 | Neftel et al. |
| 5,743,169 A | 4/1998 | Yamada |
| 5,746,708 A | 5/1998 | Giesler et al. |
| 5,755,683 A | 5/1998 | Houle et al. |
| 5,764,034 A | 6/1998 | Bowman et al. |
| 5,769,387 A | 6/1998 | Perez |
| 5,771,914 A | 6/1998 | Ling et al. |
| 5,772,635 A | 6/1998 | Dastur et al. |
| 5,772,637 A | 6/1998 | Heinzmann et al. |
| 5,775,371 A | 7/1998 | Pan et al. |
| 5,782,575 A | 7/1998 | Vincent et al. |
| 5,782,805 A | 7/1998 | Meinzer et al. |
| 5,799,207 A | 8/1998 | Wang et al. |
| 5,816,779 A | 10/1998 | Lawless et al. |
| 5,840,151 A | 11/1998 | Munsch |
| 5,842,841 A | 12/1998 | Danby et al. |
| 5,843,035 A | 12/1998 | Bowman et al. |
| 5,868,696 A | 2/1999 | Giesler et al. |
| 5,873,853 A | 2/1999 | Keilman et al. |
| 5,902,096 A | 5/1999 | Behringer et al. |
| 5,906,598 A | 5/1999 | Giesler et al. |
| 5,921,951 A | 7/1999 | Morris |
| 5,925,011 A | 7/1999 | Faict et al. |
| 5,934,885 A | 8/1999 | Farrell et al. |
| 5,935,099 A | 8/1999 | Peterson et al. |
| 5,938,634 A | 8/1999 | Packard |
| 5,984,897 A | 11/1999 | Petersen et al. |
| 5,989,423 A | 11/1999 | Kamen |
| 5,993,174 A | 11/1999 | Konishi |
| 5,996,634 A | 12/1999 | Dennehey et al. |
| 6,013,057 A | 1/2000 | Danby et al. |
| 6,036,668 A | 3/2000 | Mathis |
| 6,036,680 A | 3/2000 | Horne et al. |
| 6,041,801 A | 3/2000 | Gray et al. |
| 6,053,191 A | 4/2000 | Hussey |
| 6,065,389 A | 5/2000 | Riedlinger |
| 6,065,941 A | 5/2000 | Gray et al. |
| 6,068,612 A | 5/2000 | Bowman et al. |
| 6,074,359 A | 6/2000 | Keshaviah et al. |
| 6,079,959 A | 6/2000 | Kingsford et al. |
| 6,099,492 A | 8/2000 | Le Boeuf |
| 6,106,246 A | 8/2000 | Steck et al. |
| 6,110,410 A | 8/2000 | Owens et al. |
| 6,118,207 A | 9/2000 | Ormerod et al. |
| 6,129,517 A | 10/2000 | Danby et al. |
| 6,132,187 A | 10/2000 | Ericson |
| 6,136,565 A | 10/2000 | Best et al. |
| 6,152,705 A | 11/2000 | Kennedy et al. |
| 6,154,605 A | 11/2000 | Aonuma |
| 6,164,621 A | 12/2000 | Bouchard et al. |
| 6,165,154 A | 12/2000 | Gray et al. |
| 6,168,394 B1 | 1/2001 | Forman et al. |
| 6,178,996 B1 | 1/2001 | Suzuki |
| 6,179,801 B1 | 1/2001 | Holmes et al. |
| 6,184,356 B1 | 2/2001 | Anderson et al. |
| 6,189,857 B1 | 2/2001 | Zeger et al. |
| 6,196,987 B1 | 3/2001 | Holmes et al. |
| 6,200,287 B1 | 3/2001 | Keller et al. |
| 6,206,644 B1 | 3/2001 | Pereira et al. |
| 6,208,107 B1 | 3/2001 | Maske et al. |
| 6,208,497 B1 | 3/2001 | Seale et al. |
| 6,210,361 B1 | 4/2001 | Kamen et al. |
| 6,220,295 B1 | 4/2001 | Bouchard et al. |
| 6,223,130 B1 | 4/2001 | Gray et al. |
| 6,227,807 B1 | 5/2001 | Chase |
| 6,227,824 B1 | 5/2001 | Stehr |
| 6,228,047 B1 | 5/2001 | Dadson |
| 6,229,753 B1 | 5/2001 | Kono et al. |
| 6,231,537 B1 | 5/2001 | Holmes et al. |
| 6,234,989 B1 | 5/2001 | Brierton et al. |
| 6,250,502 B1 | 6/2001 | Cote et al. |
| 6,258,078 B1 * | 7/2001 | Thilly ............... A61J 1/2096 206/363 |
| 6,261,065 B1 | 7/2001 | Nayak et al. |
| 6,267,242 B1 | 7/2001 | Nagata et al. |
| 6,270,673 B1 | 8/2001 | Belt et al. |
| 6,280,406 B1 | 8/2001 | Dolecek et al. |
| 6,281,145 B1 | 8/2001 | Deguchi et al. |
| 6,284,142 B1 | 9/2001 | Muller |
| 6,285,155 B1 | 9/2001 | Maske et al. |
| 6,286,566 B1 | 9/2001 | Cline et al. |
| 6,294,094 B1 | 9/2001 | Muller et al. |
| 6,296,450 B1 | 10/2001 | Westberg et al. |
| 6,297,322 B1 | 10/2001 | Ding et al. |
| 6,312,412 B1 | 11/2001 | Saied et al. |
| 6,315,707 B1 | 11/2001 | Smith et al. |
| 6,315,754 B1 | 11/2001 | Daoud et al. |
| 6,316,864 B1 | 11/2001 | Ormerod |
| 6,322,488 B1 | 11/2001 | Westberg et al. |
| 6,325,775 B1 | 12/2001 | Thom et al. |
| 6,337,049 B1 | 1/2002 | Tamari |
| RE37,553 E | 2/2002 | Ciavarini et al. |
| 6,343,614 B1 | 2/2002 | Gray et al. |
| 6,348,156 B1 | 2/2002 | Vishnoi et al. |
| 6,361,518 B1 | 3/2002 | Brierton et al. |
| 6,364,857 B1 | 4/2002 | Gray et al. |
| 6,367,669 B1 | 4/2002 | Au et al. |
| 6,382,923 B1 | 5/2002 | Gray |
| 6,383,158 B1 | 5/2002 | Utterberg |
| 6,402,486 B1 | 6/2002 | Steck et al. |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,419,822 B2 | 7/2002 | Muller et al. |
| 6,455,676 B1 | 9/2002 | Weickert et al. |
| 6,471,855 B1 | 10/2002 | Odak et al. |
| 6,481,980 B1 | 11/2002 | Vandlik et al. |

(56) References Cited

U.S. PATENT DOCUMENTS

| | | | |
|---|---|---|---|
| 6,484,383 B1 | 11/2002 | Herklotz |
| 6,489,896 B1 | 12/2002 | Platt et al. |
| 6,491,656 B1 | 12/2002 | Morris |
| 6,494,694 B2 | 12/2002 | Lawless et al. |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,529,573 B2 | 3/2003 | Olsher et al. |
| 6,537,445 B2 | 3/2003 | Muller |
| 6,542,761 B1 | 4/2003 | Jahn et al. |
| 6,558,343 B1 | 5/2003 | Neftel |
| 6,572,604 B1 | 6/2003 | Platt et al. |
| 6,579,253 B1 | 6/2003 | Burbank et al. |
| 6,582,399 B1 * | 6/2003 | Smith ............ A61M 5/31511 604/152 |
| 6,592,542 B2 | 7/2003 | Childers et al. |
| 6,595,948 B2 | 7/2003 | Suzuki et al. |
| 6,603,229 B1 | 8/2003 | Toye, IV |
| 6,604,908 B1 | 8/2003 | Bryant et al. |
| 6,645,166 B2 | 11/2003 | Scheunert et al. |
| 6,645,177 B1 | 11/2003 | Shearn |
| 6,648,861 B2 | 11/2003 | Platt et al. |
| 6,663,359 B2 | 12/2003 | Gray |
| 6,670,323 B1 | 12/2003 | Looker et al. |
| 6,672,841 B1 | 1/2004 | Herklotz et al. |
| 6,695,593 B1 | 2/2004 | Steck et al. |
| 6,695,803 B1 | 2/2004 | Robinson et al. |
| 6,709,417 B1 | 3/2004 | Houle et al. |
| 6,716,004 B2 | 4/2004 | Vandlik et al. |
| 6,723,062 B1 | 4/2004 | Westberg et al. |
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Doenig et al. |
| 6,746,514 B2 | 6/2004 | Bedingfield et al. |
| 6,746,637 B1 | 6/2004 | Huss et al. |
| 6,749,403 B2 | 6/2004 | Bryant et al. |
| 6,752,172 B2 | 6/2004 | Lauer |
| 6,752,599 B2 | 6/2004 | Park |
| 6,755,801 B2 | 6/2004 | Utterberg et al. |
| 6,758,975 B2 | 7/2004 | Peabody et al. |
| 6,759,007 B1 | 7/2004 | Westberg et al. |
| 6,759,014 B2 | 7/2004 | Dales et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,774,517 B2 | 8/2004 | Kowalski et al. |
| 6,790,014 B2 | 9/2004 | Bowen |
| 6,790,195 B2 | 9/2004 | Steele et al. |
| 6,790,198 B1 | 9/2004 | White et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,828,125 B1 | 12/2004 | Hoffman et al. |
| 6,846,161 B2 | 1/2005 | Kline et al. |
| 6,852,090 B2 | 2/2005 | Burbank et al. |
| 6,869,538 B2 | 3/2005 | Yu et al. |
| 6,905,479 B1 | 6/2005 | Bouchard et al. |
| 6,929,751 B2 | 8/2005 | Bowman, Jr. et al. |
| 6,939,111 B2 | 9/2005 | Huitt et al. |
| 6,949,079 B1 | 9/2005 | Westberg et al. |
| 6,953,323 B2 | 10/2005 | Childers et al. |
| 6,957,952 B1 | 10/2005 | Steck et al. |
| 6,984,218 B2 | 1/2006 | Nayak et al. |
| 7,021,148 B2 | 4/2006 | Kuhn et al. |
| 7,029,245 B2 | 4/2006 | Maianti et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman, Jr. et al. |
| 7,087,036 B2 | 8/2006 | Busby et al. |
| 7,107,837 B2 | 9/2006 | Lauman et al. |
| 7,115,107 B2 | 10/2006 | Delnevo et al. |
| 7,115,228 B2 | 10/2006 | Lundtveit et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman et al. |
| 7,195,607 B2 | 3/2007 | Westberg et al. |
| 7,211,560 B2 | 5/2007 | Looker et al. |
| 7,232,435 B2 | 6/2007 | Hildebrand et al. |
| 7,236,936 B2 | 6/2007 | White et al. |
| 7,238,164 B2 | 7/2007 | Childers et al. |
| 7,255,680 B1 | 8/2007 | Gharib |
| 7,258,534 B2 | 8/2007 | Fathallah et al. |
| 7,261,559 B2 | 8/2007 | Smith et al. |
| 7,267,661 B2 | 9/2007 | Susi |
| 7,273,465 B2 | 9/2007 | Ash |
| 7,306,578 B2 | 12/2007 | Gray et al. |
| 7,331,935 B2 | 2/2008 | Barere |
| 7,338,469 B2 | 3/2008 | Barker et al. |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,461,968 B2 | 12/2008 | Demers et al. |
| 7,490,021 B2 | 2/2009 | Holland et al. |
| 7,500,962 B2 | 3/2009 | Childers et al. |
| 7,517,387 B2 | 4/2009 | Chevallet et al. |
| 7,553,295 B2 | 6/2009 | Susi |
| 7,556,616 B2 | 7/2009 | Fathallah et al. |
| 7,575,564 B2 | 8/2009 | Childers |
| 7,618,948 B2 | 11/2009 | Kaemmerer |
| 7,645,258 B2 | 1/2010 | White et al. |
| 7,648,627 B2 | 1/2010 | Beden et al. |
| 7,654,976 B2 | 2/2010 | Peterson et al. |
| 7,662,133 B2 | 2/2010 | Scarborough et al. |
| 7,662,286 B2 | 2/2010 | Childers et al. |
| 7,699,966 B2 | 4/2010 | Qin et al. |
| 7,717,682 B2 | 5/2010 | Orr |
| 7,789,849 B2 | 9/2010 | Busby et al. |
| 7,815,595 B2 | 10/2010 | Busby et al. |
| 8,038,640 B2 | 10/2011 | Orr |
| 8,142,653 B2 | 3/2012 | Beden et al. |
| 8,192,401 B2 | 6/2012 | Morris et al. |
| 8,197,231 B2 | 6/2012 | Orr |
| 8,197,439 B2 | 6/2012 | Wang et al. |
| 8,206,338 B2 | 6/2012 | Childers et al. |
| 8,292,594 B2 | 10/2012 | Tracey et al. |
| 8,366,921 B2 | 2/2013 | Beden et al. |
| 8,377,293 B2 | 2/2013 | Beden et al. |
| 8,409,441 B2 | 4/2013 | Wilt |
| 8,435,408 B2 | 5/2013 | Beden et al. |
| 8,562,834 B2 | 10/2013 | Kamen et al. |
| 8,721,879 B2 | 5/2014 | van der Merwe et al. |
| 8,721,883 B2 | 5/2014 | Lauer |
| 8,926,835 B2 | 1/2015 | Beden et al. |
| 8,932,032 B2 | 1/2015 | Orr |
| 8,986,254 B2 | 3/2015 | Morris et al. |
| 9,011,114 B2 | 4/2015 | Farrell et al. |
| 9,101,709 B2 | 8/2015 | Beden et al. |
| 9,180,240 B2 | 11/2015 | Farrell et al. |
| 9,421,314 B2 | 8/2016 | Plahey et al. |
| 9,500,188 B2 | 11/2016 | Ly et al. |
| 9,610,392 B2 | 4/2017 | Farrell et al. |
| 9,624,915 B2 | 4/2017 | Medina |
| 2001/0034502 A1 | 10/2001 | Moberg et al. |
| 2001/0037763 A1 | 11/2001 | Deguchi et al. |
| 2001/0043450 A1 | 11/2001 | Seale et al. |
| 2002/0045851 A1 | 4/2002 | Suzuki et al. |
| 2002/0062109 A1 | 5/2002 | Lauer |

(56) References Cited

U.S. PATENT DOCUMENTS

| | | |
|---|---|---|
| 2002/0072718 A1 | 6/2002 | Brugger et al. |
| 2002/0098097 A1 | 7/2002 | Singh |
| 2002/0107474 A1 | 8/2002 | Noack |
| 2002/0147423 A1 | 10/2002 | Burbank et al. |
| 2003/0018395 A1 | 1/2003 | Crnkovich et al. |
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0100882 A1 | 5/2003 | Beden et al. |
| 2003/0136189 A1 | 7/2003 | Lauman et al. |
| 2003/0194332 A1 | 10/2003 | Jahn et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping et al. |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0001766 A1 | 1/2004 | Maianti et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli et al. |
| 2004/0084647 A1 | 5/2004 | Beden et al. |
| 2004/0109769 A1 | 6/2004 | Jahn et al. |
| 2004/0115068 A1 | 6/2004 | Hansen et al. |
| 2004/0135078 A1 | 7/2004 | Mandro et al. |
| 2004/0136843 A1 | 7/2004 | Jahn et al. |
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0054968 A1 | 3/2005 | Giannella |
| 2005/0230292 A1 | 10/2005 | Beden et al. |
| 2006/0002823 A1 | 1/2006 | Feldstein |
| 2006/0079766 A1 | 4/2006 | Neer et al. |
| 2006/0079826 A1 | 4/2006 | Beden et al. |
| 2006/0195064 A1 | 8/2006 | Plahey et al. |
| 2007/0040454 A1 | 2/2007 | Freudenberger et al. |
| 2007/0112297 A1 | 5/2007 | Plahey et al. |
| 2007/0149913 A1 | 6/2007 | Busby, Jr. et al. |
| 2007/0193940 A1 | 8/2007 | Duchamp et al. |
| 2007/0213651 A1 | 9/2007 | Busby, Jr. et al. |
| 2007/0213653 A1 | 9/2007 | Childers et al. |
| 2007/0269340 A1 | 11/2007 | Dannenmaier et al. |
| 2007/0278155 A1 | 12/2007 | Lo et al. |
| 2008/0033346 A1 | 2/2008 | Childers et al. |
| 2008/0077068 A1 | 3/2008 | Orr |
| 2008/0125693 A1 | 5/2008 | Gavin et al. |
| 2008/0208103 A1 | 8/2008 | Demers et al. |
| 2008/0216898 A1 | 9/2008 | Grant et al. |
| 2008/0253912 A1 | 10/2008 | Demers et al. |
| 2009/0004033 A1 | 1/2009 | Demers et al. |
| 2009/0099498 A1 | 4/2009 | Demers et al. |
| 2009/0137940 A1 | 5/2009 | Orr |
| 2009/0169402 A1 | 7/2009 | Stenberg et al. |
| 2009/0212248 A1 | 8/2009 | Kozak |
| 2010/0021313 A1 | 1/2010 | Devan et al. |
| 2010/0133153 A1 | 6/2010 | Beden et al. |
| 2010/0211044 A1 | 8/2010 | Dacquay et al. |
| 2010/0241062 A1* | 9/2010 | Morris .............. A61M 1/14 604/29 |
| 2010/0286614 A1 | 11/2010 | Ring |
| 2011/0015610 A1 | 1/2011 | Plahey et al. |
| 2011/0020156 A1 | 1/2011 | Van et al. |
| 2011/0092895 A1 | 4/2011 | Yardimci et al. |
| 2011/0125085 A1 | 5/2011 | McGill et al. |
| 2011/0137237 A1 | 6/2011 | Prisco et al. |
| 2011/0152785 A1 | 6/2011 | Chattaraj et al. |
| 2011/0274566 A1 | 11/2011 | Amirouche et al. |
| 2011/0293450 A1 | 12/2011 | Grimes et al. |
| 2012/0022354 A1 | 1/2012 | Beyer et al. |
| 2012/0061310 A1 | 3/2012 | Beden et al. |
| 2012/0065581 A1 | 3/2012 | Childers et al. |
| 2012/0073432 A1 | 3/2012 | Ingersoll et al. |
| 2012/0123322 A1 | 5/2012 | Scarpaci et al. |
| 2012/0136298 A1* | 5/2012 | Bendix .............. A61M 5/2448 604/89 |
| 2012/0156097 A1 | 6/2012 | Beden et al. |
| 2012/0181225 A1 | 7/2012 | Weis |
| 2012/0181226 A1 | 7/2012 | Lauer |
| 2012/0181231 A1 | 7/2012 | Beden et al. |
| 2012/0209169 A1 | 8/2012 | Morris et al. |
| 2012/0224984 A1 | 9/2012 | Orr |
| 2012/0230844 A1 | 9/2012 | Farrell et al. |
| 2012/0232469 A1 | 9/2012 | Medina |
| 2012/0271226 A1 | 10/2012 | Farrell et al. |
| 2012/0308412 A1 | 12/2012 | Rochat |
| 2013/0118961 A1 | 5/2013 | Beden et al. |
| 2013/0118970 A1 | 5/2013 | Beden et al. |
| 2013/0183170 A1 | 7/2013 | Laermer |
| 2013/0184638 A1 | 7/2013 | Scarpaci et al. |
| 2013/0330208 A1 | 12/2013 | Ly et al. |
| 2013/0331774 A1 | 12/2013 | Farrell et al. |
| 2015/0098846 A1 | 4/2015 | Orr |
| 2015/0165105 A1 | 8/2015 | Beden et al. |
| 2016/0331883 A1 | 11/2016 | Plahey et al. |
| 2017/0203023 A1 | 7/2017 | Farrell et al. |

FOREIGN PATENT DOCUMENTS

| | | |
|---|---|---|
| DE | 4006785 | 9/1990 |
| DE | 4336336 | 5/1994 |
| DE | 19837667 | 3/2000 |
| DE | 19919572 A1 | 11/2000 |
| DE | 10042324 | 2/2002 |
| DE | 10046651 | 4/2002 |
| DE | 19919572 C2 | 4/2002 |
| DE | 10053441 | 5/2002 |
| DE | 69618766 | 8/2002 |
| DE | 10143137 | 4/2003 |
| DE | 10157924 | 6/2003 |
| DE | 102007059239 | 6/2009 |
| EP | 0257279 | 3/1988 |
| EP | 0314379 | 2/1991 |
| EP | 0410125 B1 | 8/1993 |
| EP | 0728509 | 8/1996 |
| EP | 0848193 | 6/1998 |
| EP | 0856321 | 8/1998 |
| EP | 0947814 | 10/1999 |
| EP | 0956876 | 11/1999 |
| EP | 1529545 | 5/2005 |
| GB | 1483702 | 8/1977 |
| GB | 2101232 | 1/1983 |
| GB | 2331796 | 6/1999 |
| JP | 0396850 A | 4/1991 |
| JP | 04191755 | 7/1992 |
| JP | 06154314 | 6/1994 |
| JP | 06002650 | 11/1994 |
| JP | 08028722 | 2/1996 |
| JP | 1068383 A | 3/1998 |
| JP | 11347115 | 12/1999 |
| JP | 2000070358 | 3/2000 |
| JP | 2000346214 | 12/2000 |
| WO | 8402473 | 7/1984 |
| WO | 8601115 | 2/1986 |
| WO | WO1994015660 A1 | 7/1994 |
| WO | 9420155 | 9/1994 |
| WO | 9625064 | 8/1996 |
| WO | 1997016214 | 5/1997 |
| WO | 9737703 | 10/1997 |
| WO | 9822165 | 5/1998 |
| WO | WO1998022167 A1 | 5/1998 |
| WO | 0023140 | 4/2000 |
| WO | 0033898 | 6/2000 |
| WO | 0117605 | 3/2001 |
| WO | 0225146 | 3/2002 |

(56) References Cited

FOREIGN PATENT DOCUMENTS

| WO | 0225225 | 3/2002 |
|---|---|---|
| WO | WO2007006030 A3 | 6/2007 |
| WO | 2009071069 | 6/2009 |
| WO | WO2010128914 A1 | 11/2010 |
| WO | WO2011045167 A1 | 4/2011 |

OTHER PUBLICATIONS

Gambro®, "Prisma® HF 1000, For Increased Filtration Capacity", © Aug. 2001, Gambro Renal Products, Inc., Lakewood, CO, 2 pp.
Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.
Gambro®, "Prismaflex™ anticipating critical care needs and taking our innovative response . . . to new heights," © 2004, Gambro Inc., Lakewood, CO, 8 pp.
Glenn Avolio, "Principles of Rotary Optical Encoders," Sensors Journal of Machine Perception, vol. 10, No. 4, pp. 10-18, 1993.
Manns, Markus et al., "The acu-men: A new device for continuous renal replacement therapy in acute renal failure," Kidney International, vol. 54, pp. 268-274, 1998.
Liberty Cycler Operator's Manual, 2003-2004.
Newton IQ Cycler Operator Manual, Part No. 470203 Rev. F, 2000-2006.
Operator's Instructions, Fresenius 90/2 Peritoneal Therapy Cycler, Part No. 470016, Rev. B, 1991.
Operator's Manual, Serena, Program Version 3.xx—English, 2002.
Sleep Safe Operating Instructions, Software Version 0.9, Part No. 677 801 1; Aug. 2000.
Sleep Safe Technical Manual, Part No. 677 807 1; Aug. 2000.
Notification Concerning Transmittal of International Preliminary Report on Patentability for corresponding PCT Application No. PCT/US2012/032672, dated Oct. 31, 2013, 9 pages.
Bolegoh, Gordon, "Pumps: Reference Guide", p. 24, 3rd edition, 2001.
Ronco et al., "Evolution of Machines for Automated Peritoneal Dialysis", in Automated Peritoneal Dialysis, Contributions to Nephrology, vol. 129, pp. 142-161, 1999.
Sleep Safe Operating Instructions, Software Version 0.5, Apr. 1999.
Sleep Safe Operating Instructions, Software Version 1.0, Oct. 2000.
Sleep Safe Technical Manual, Dec. 2001.
Sleep Safe Operating Instructions, Jan. 2002.
Sleep Safe Communicating Therapy, Mar. 1998.
Sleep Safe Kommunizierte Therapie, May 1998.
Innovative Technologies in Peritoneal Dialysis, Sleep Safe Concept, Oct. 13, 1999 (4 attachments).
TL™ Pump Brochure, TL Systems Corporation, Apr. 1975.
Google definition for Hall Effect Sensor, accessed Jul. 30, 2015.
Hall Sensor Effect—NPL Wayback Mar. 11, 2011. www.movingmagnet.com, Technologies, Magnetic and Hall effect Position Sensors.
International Search Report and Written Opinion for PCT Application No. PCT/US2012/032672, dated Jun. 13, 2012, 13 pages.
International Search Report and Written Opinion, PCT/US2010/041976, dated Dec. 2, 2010.

\* cited by examiner

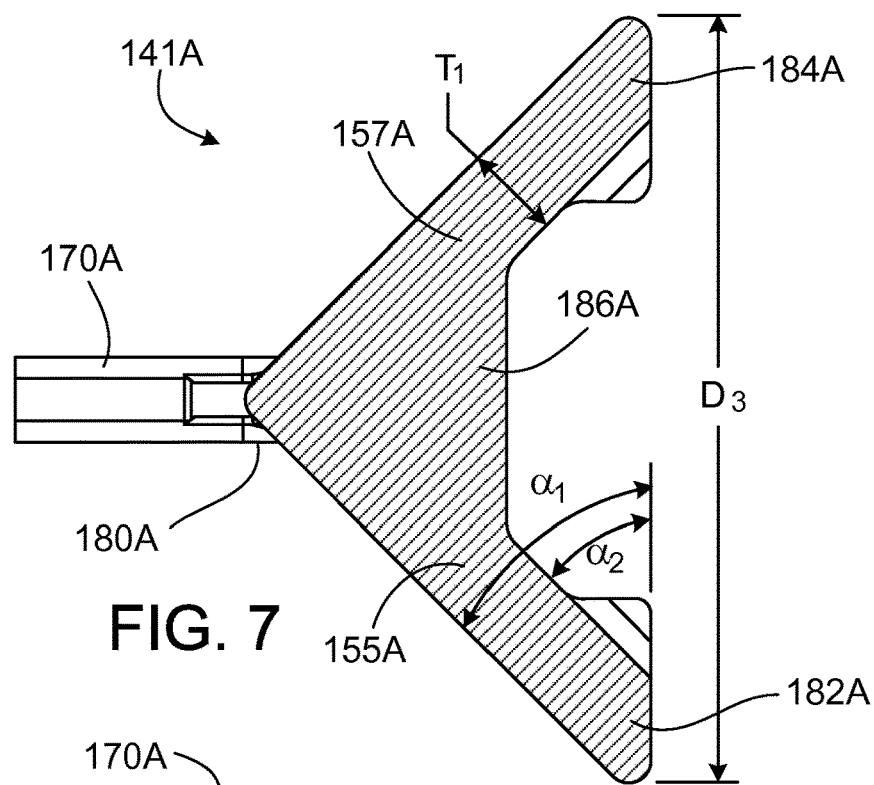
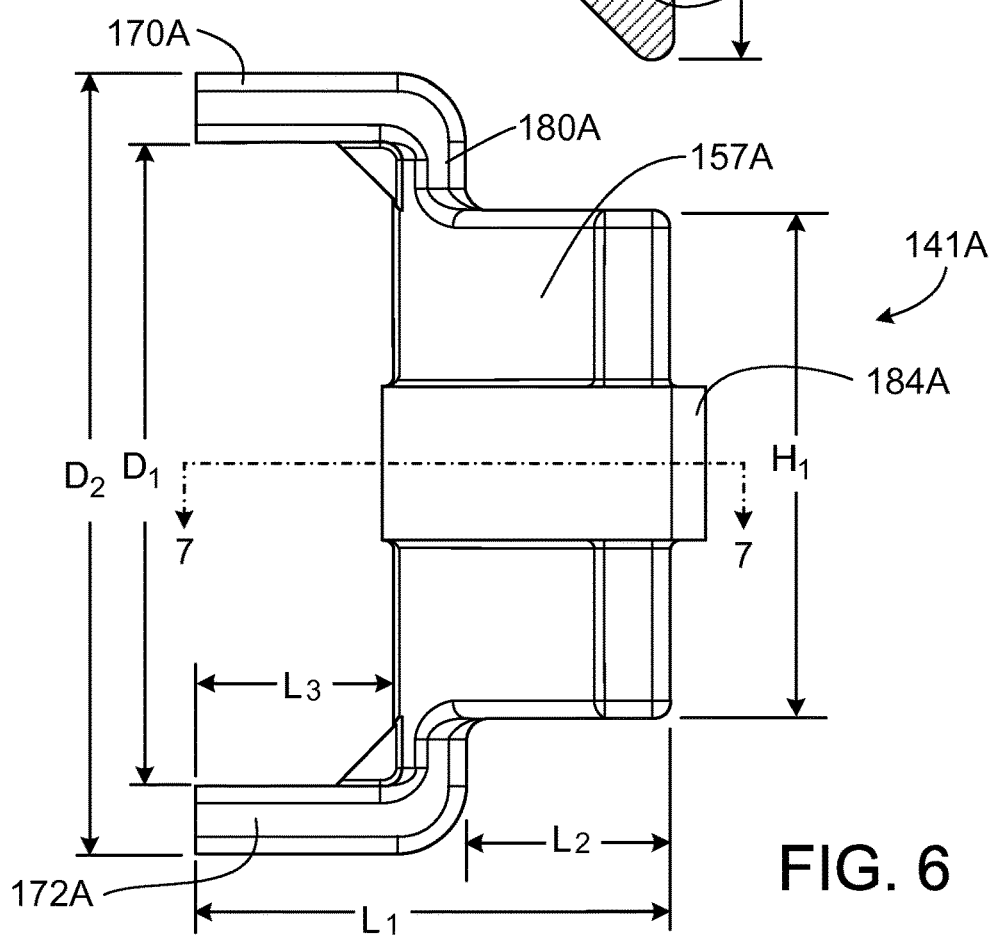

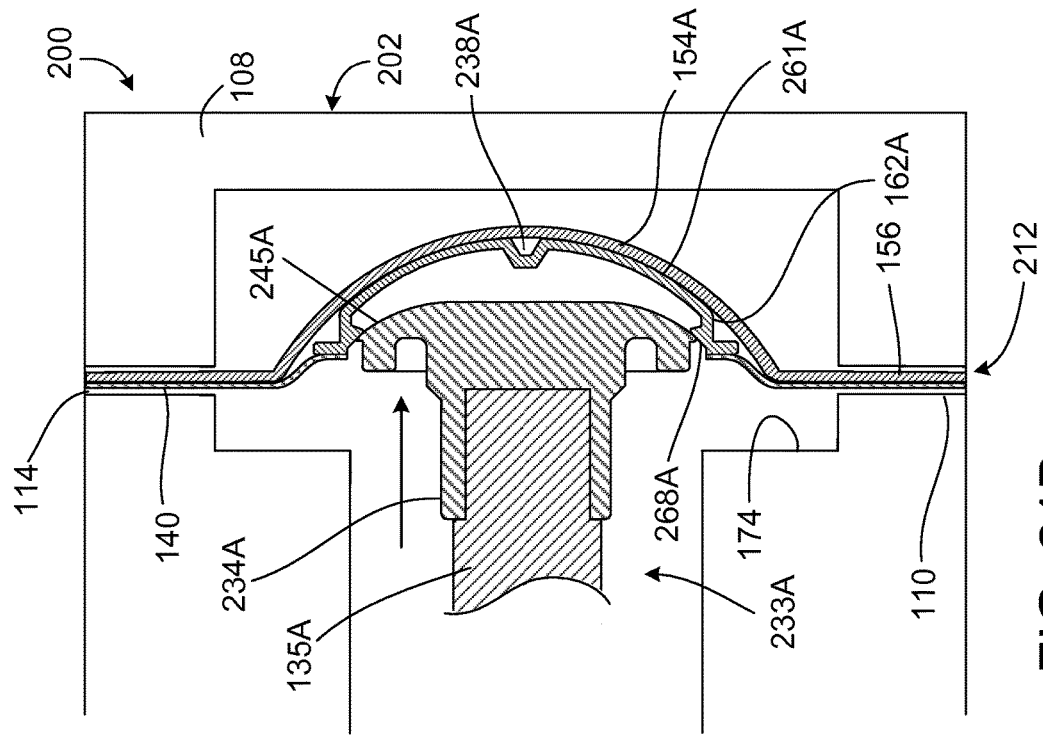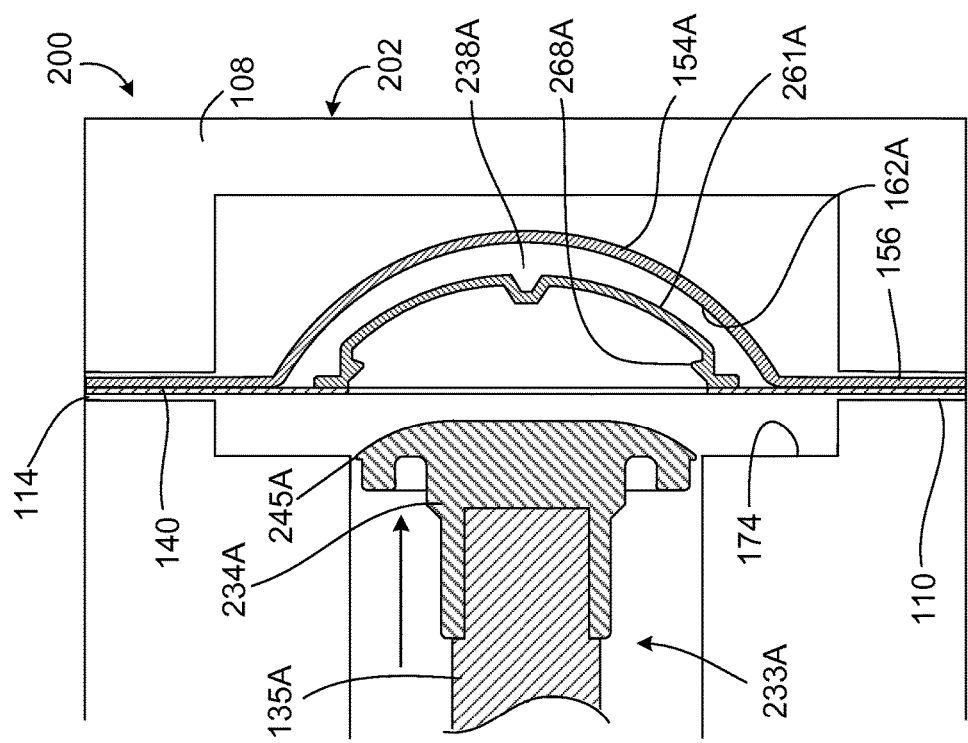

MEDICAL FLUID PUMPING SYSTEMS AND RELATED DEVICES AND METHODS

CROSS-REFERENCE TO RELATED APPLICATIONS

This application is a continuation of U.S. Ser. No. 13/442,184, filed Apr. 9, 2012, which claims the benefit of U.S. Application Ser. No. 61/477,742, filed on Apr. 21, 2011.

TECHNICAL FIELD

This disclosure relates to medical fluid pumping systems and related devices and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain procedure to empty the peritoneal cavity of used or spent dialysate. The sequence then proceeds through the succession of fill, dwell, and drain phases that follow one after the other. Each phase is called a cycle.

SUMMARY

In one aspect of the invention, a medical fluid pumping system includes a medical fluid pumping machine including a piston head that can be linearly displaced and a medical fluid cassette that can be secured to the medical fluid pumping machine. The medical fluid cassette includes a base, a flexible membrane attached to the base in a manner such that the flexible membrane and the base cooperate to at least partially define a fluid pump chamber, and a fastening member attached to the flexible membrane. The fastening member defines a recess configured to receive the piston head of the medical fluid pumping machine, and the fastening member has an engagement surface that engages an engagement surface of the piston head when the piston head is disposed in the recess such that, when the piston head is disposed in the recess and is moved linearly away from the base of the cassette, the engagement surface of the piston head is engaged with the engagement surface of the fastening member and pulls the fastening member and the flexible membrane to which the fastening member is attached away from the base to increase a volume of the fluid pump chamber.

In another aspect of the invention, a medical fluid cassette includes a base, a flexible membrane attached to the base in a manner such that the flexible membrane and the base cooperate to at least partially define a fluid pump chamber, and a fastening member attached to the flexible membrane. The fastening member defines a recess configured to receive a piston head of a medical fluid pumping machine and has an engagement surface that engages the piston head when the piston head is disposed in the recess such that, when the piston head is disposed in the recess and is moved linearly away from the base of the cassette, the piston head engages the engagement surface of the fastening member to pull the fastening member and the flexible membrane to which the fastening member is attached away from the base and increase a volume of the fluid pump chamber.

In a further aspect of the invention, a medical fluid pumping machine includes a piston head that can be linearly displaced and is configured to be disposed within a recess defined by a fastening member of a medical fluid cassette. The piston head has an engagement surface configured to engage an engagement surface of the medical fluid cassette when the piston head is disposed in the recess such that, when the piston head is disposed in the recess and is moved linearly away from a base of the cassette, the engagement surface of the piston head is engaged with the engagement surface of the fastening member and pulls the fastening member and a flexible membrane to which the fastening member is attached away from the base to increase a volume of a fluid pump chamber defined in the cassette between the flexible membrane and the base.

In an additional aspect of the invention, a medical fluid pumping method includes advancing a piston head into a recessed region of a fastening member of a medical fluid cassette to mechanically connect the piston head to the fastening member, and then reciprocating the piston head to cause the fastening member to alternately retract and advance, which causes fluid to alternately be drawn into a fluid pump chamber of the cassette and forced out of the fluid pump chamber of the cassette.

Implementations can include one or more of the following features.

In some implementations, the medical fluid cassette can be secured to the medical fluid pumping machine by disposing the medical fluid cassette within a cassette compartment defined by the medical fluid pumping machine.

In certain implementations, the cassette compartment is defined between a door and a cassette interface of the medical fluid pumping machine.

In some implementations, the fastening member is substantially centered relative to the fluid pump chamber of the medical fluid cassette.

In certain implementations, the fastening member includes a substantially dome-shaped member.

In some implementations, the engagement surface of the fastening member is a surface of a radially inwardly extending projection of the substantially dome-shaped member.

In certain implementations, the projection extends continuously around a perimeter region of the substantially dome-shaped member.

In some implementations, the fastening member includes a peg extending from a surface of the dome-shaped member.

In certain implementations, the engagement surface of the fastening member is a surface of an enlarged head of the peg.

In some implementations, the piston head includes a body portion and a contact surface that extends radially beyond a perimeter of the body portion. The contact surface of the piston head is configured to contact a contact surface of the fastening member of the medical fluid cassette when the piston head is inserted into the recess of the fastening member.

In certain implementations, the contact surfaces are angled at about 30 degrees to about 60 degrees relative to a longitudinal axis of the piston head.

In some implementations, the contact surface of the piston head is configured to move radially inwardly when the piston head is inserted into the recess of the fastening member.

In certain implementations, the contact surface of the piston head is a surface of a latch that is radially moveable relative to a body portion of the piston head.

In some implementations, the contact surface of the fastening member is configured to deflect radially outwardly when the piston head is inserted into the recess of the fastening member.

In certain implementations, the contact surface of the fastening member is a surface of a radially inwardly extending projection of the fastening member.

In some implementations, the piston head includes a latch secured to a body portion of the piston head, the engagement surface of the piston head is a surface of the latch, and the latch has an extended position in which the surface of the latch is positioned radially outward of a perimeter of the body portion.

In certain implementations, the latch has a retracted position in which the surface of the latch is positioned radially inward of the perimeter of the body portion.

In some implementations, the piston head further includes a second latch that is secured to the body portion of the piston head and has an extended position in which an engagement surface of the second latch is positioned radially outward of the perimeter of the body portion and a retracted position in which the engagement surface of the latch is positioned radially inward of the perimeter of the body portion.

In certain implementations, the body portion includes front and rear members, and the latch is positioned in a space defined between the front and rear members.

In some implementations, the piston head further includes a latch lock having a first angled surface that sits adjacent an associated first angled surface of the latch such that radially inward movement of the latch causes axial movement of the latch lock in a first axial direction.

In certain implementations, the first angled surfaces are at an angle of about 30 degrees to about 60 degrees relative to a longitudinal axis of the piston head.

In some implementations, the first angled surface of the latch and the first angled surface of the latch lock are at substantially the same angle relative to a longitudinal axis of the piston head.

In certain implementations, the piston head further includes a spring disposed between the latch lock and the front member to resist the axial movement of the latch lock in the first axial direction.

In some implementations, the latch and the latch lock are configured such that when a force applied to the latch to move the latch radially inwardly and to move the latch lock axially is released, the spring expands and moves the latch lock in a second axial direction opposite the first axial direction and causes the latch to move radially outwardly.

In certain implementations, the latch lock has a second angled surface that sits adjacent an associated second angled surface of the latch such that the axial movement of the latch lock in the second axial direction causes the radially outward movement of the latch.

In some implementations, the latch defines a slot in which a leg of the latch lock is disposed, and the first and second angled surfaces of the latch lock are surfaces of the leg, and the first and second angled surfaces of the latch are surfaces that define the slot.

In certain implementations, the piston head includes a body portion and a flange that extends at least partially around a perimeter of the body portion, and the engagement surface of the piston head is a surface of the flange of the piston head.

In some implementations, the fastening member has a projection that extends at least partially around a perimeter of the recess, and the engagement surface of the fastening member is a surface of the projection of the fastening member.

In certain implementations, the fastening member is a substantially dome-shaped member.

In some implementations, the projection extends continuously around the perimeter of the recess.

In certain implementations, an outer diameter of the flange of the piston head is greater than an inner diameter of the flange of the fastening member, and the piston head and the fastening member are constructed such that at least one of the flanges deflects radially relative to the other of the flanges as the piston head is inserted into the recess of the fastening member to allow the piston head to be disposed within the recess.

In some implementations, the piston head includes a clamp, the fastening member includes a peg configured to be releasably engaged by the clamp, and the engagement surfaces of the piston head and the fastening member are surfaces of the clamp and the peg, respectively.

In certain implementations, the clamp is positioned within a bore defined by a body portion of the piston head.

In some implementations, the clamp includes first and second resilient fingers that are configured to deflect away from one another when the peg is received in the clamp.

In certain implementations, each of the first and second resilient fingers includes a first projection that extends radially inwardly from a base portion of its respective resilient finger.

In some implementations, a front surface of the first projection of each of the resilient fingers is angled relative to a longitudinal axis of the piston head to cause the first and second resilient fingers to deflect away from one another as the peg is received in the clamp and slides along the front surface of each first projection.

In certain implementations, the front surface of the first projection of each of the resilient fingers is angled at about 30 degrees to about 60 degrees relative to the longitudinal axis of the piston head.

In some implementations, a rear surface of the first projection of each of the resilient fingers is angled relative to a longitudinal axis of the piston head to cause the first and second resilient fingers to deflect away from one another as the peg is removed from the clamp and slides along the rear surface of each first projection.

In certain implementations, the rear surface of the first projection of each of the resilient fingers is angled at about 30 degrees to about 60 degrees relative to the longitudinal axis of the piston head.

In some implementations, each of the first and second resilient fingers further includes a second projection that extends radially inwardly from the base portion of its respective resilient finger and is axially offset from the first projection of its respective finger such that the peg rests between the first and second projections of each of the resilient fingers when the peg is disposed in the clamp.

In certain implementations, the piston head further includes a shaft, the clamp and the body portion are axially moveable relative to the shaft, and the shaft is configured to deflect the resilient fingers of the clamp away from one another when the piston head and the clamp are retracted a certain distance relative to the shaft.

In some implementations, a rear surface of the second projection of each of the resilient fingers is positioned to contact the shaft when the body portion of the piston head and the clamp are retracted the certain distance relative to the shaft, and the rear surface of the second projection of each of the resilient fingers is angled relative to a longitudinal axis of the piston head to cause the first and second resilient fingers to deflect away from one another as the body portion of the piston head and the clamp are retracted the certain distance relative to the shaft.

In certain implementations, the rear surface of the second projection of each of the resilient fingers is angled at about 30 degrees to about 60 degrees relative to the longitudinal axis of the piston head.

In some implementations, a front surface of the second projection of each of the resilient fingers is substantially perpendicular to the longitudinal axis of the piston head.

In certain implementations, the piston head and the fastening member are constructed to become mechanically connected when the piston head is moved toward the base of the cassette and to become disconnected when the piston head is moved away from the base of the cassette.

In some implementations, the piston head is disposed within the recess of the fastening member and the engagement surfaces contact one another when the piston head and the fastening member are mechanically connected.

In certain implementations, the piston head and the fastening member are constructed to require an axial force of about 5.0 lbf to about 50 lbf to dispose the piston head within the recess of the fastening member such that the piston head and fastening member become mechanically connected.

In some implementations, the piston head and the fastening member are constructed to require an axial force of at least 50 pounds to remove the piston head from the recess of the fastening member such that the piston head and fastening member become disconnected from one another.

In certain implementations, the medical fluid pumping machine is a dialysis machine.

In some implementations, the dialysis machine is a peritoneal dialysis machine.

In certain implementations, the fastening member is constructed to become mechanically connected to the piston head when the piston head is moved toward the base of the cassette and to become disconnected from the piston head when the piston head is moved away from the base of the cassette.

In some implementations, the medical fluid cassette is a dialysis fluid cassette.

In certain implementations, the dialysis fluid cassette is a peritoneal dialysis fluid cassette.

In some implementations, the piston head is advanced into the recessed region of the fastening member with an axial force of about 5 lbf to about 50 lbf.

In certain implementations, the medical fluid pumping method further includes, after reciprocating the piston head, retracting the piston head a certain distance to disconnect the piston head from the fastening member of the medical fluid cassette.

In some implementations, the piston head is retracted out of the recessed region of the fastening member with an axial force of at least 50 pounds.

In certain implementations, the medical fluid cassette includes a base, a flexible membrane attached to the base in a manner such that the flexible membrane and the base cooperate to at least partially define the fluid pump chamber, and the fastening member attached to the flexible membrane. The fastening member has an engagement surface that engages an engagement surface of the piston head when the piston head is disposed in the recess such that, when the piston head is disposed in the recess and is moved linearly away from the base of the cassette, the engagement surface of the piston head is engaged with the engagement surface of the fastening member and pulls the fastening member and the flexible membrane to which the fastening member is attached away from the base to increase a volume of the fluid pump chamber and draw fluid into the fluid pump chamber.

Implementations can include one or more of the following advantages.

In certain implementations, a relatively simple mechanical connection, such as a snap-fit connection, can be used to connect the piston head of the medical fluid pumping machine to the fastening member of the medical fluid cassette. As a result, the system can be more user-friendly, less expensive, and quieter than certain medical fluid pumping systems that utilize vacuum-based connections between a medical fluid pumping machine and a medical fluid cassette.

In some implementations, the piston head of the medical fluid pump machine can be automatically mechanically connected to the fastening member of the medical fluid cassette by simply advancing the piston head a certain distance relative to the cassette, and the piston head of the medical fluid pump machine can be automatically mechanically disconnected from the fastening member of the medical fluid cassette by simply retracting the piston head a certain distance relative to the cassette. As a result of these automatic connection and disconnection processes, the operator of the machine need not take manual steps to cause the connection or disconnection of the piston head and the fastening member, which makes the system more user-friendly and reduces the risk of human errors that might negatively affect the treatment.

In certain implementations, the piston head includes a retractable latch mechanism that allows the piston head and its associated fastening member on the cassette to be mechanically connected and disconnected while reducing (e.g., minimizing) the amount of force required to be applied to the fastening member by the piston head. This arrangement can reduce (e.g., minimize) deformation of the piston head and the fastening member resulting from the connection and disconnection processes and can thus increase the pumping accuracy of the system. In particular, reducing deformation of the piston head and the fastening member can help to ensure that a tight fit is maintained between the piston head and the fastening member and can thus reduce (e.g., minimize) movement, such as slippage, that occurs between the piston head and the fastening member during the pumping process.

In certain implementations, the engagement surface of the latch is angled relative to the longitudinal axis of the piston (e.g., angled at about 60 to about 70 degrees) relative to the longitudinal axis of the piston). This angled arrangement can enable the piston head to be mechanically connected to fastening members of slightly different sizes (e.g., due to tolerances in the manufacturing process). In particular, the angled engagement surface allows the latch to tightly engage slightly differently sized fastening members by expanding radially outward slightly different distances.

Other aspects, features, and advantages will be apparent from the description and drawings, and from the claims.

DESCRIPTION OF DRAWINGS

FIG. 6 is a side view of a latch lock of one of the piston heads of the PD cycler of FIG. 1.

FIG. 7 is a cross-sectional view of the latch lock, taken along line 7-7 in FIG. 6.

FIGS. 21A-21C are diagrammatic cross-sectional views of a PD cassette in the cassette compartment of the PD cycler of FIG. 20, during different phases of a pumping operation.

DETAILED DESCRIPTION

This disclosure relates generally to medical fluid pumping systems and related devices and methods. In some cases, a medical fluid pumping system (e.g., a peritoneal dialysis ("PD") system) includes a medical fluid pumping machine (e.g., a PD cycler) having a piston with a piston head that can be mechanically connected to a medical fluid cassette (e.g., a PD fluid cassette). Typically, the cassette includes a flexible membrane and a fastening member (e.g., a dome-shaped fastening member) attached to the membrane. The membrane and the fastening member overlie a recessed region of a rigid base of the cassette to form a fluid pump chamber, and the piston of the medical fluid pumping machine is designed to be mechanically connected to the fastening member of the cassette. With the piston of the medical fluid pumping machine mechanically connected to the fastening member of the cassette, reciprocation of the piston causes fluid to be alternately drawn into and forced out of the fluid pump chamber by pulling the fastening member and membrane away from the recessed region of the base and then advancing the fastening member and membrane toward the recessed region of the base. As discussed below, in some cases, the piston can be automatically mechanically connected to the fastening member of the cassette by simply moving the piston toward the base of the cassette and into engagement with the fastening member prior to a medical treatment (e.g., PD treatment) and can be automatically disconnected from the fastening member of the cassette by simply moving the piston away from the base of the cassette and out of engagement with the fastening member after completion of the medical treatment.

Figure 1:
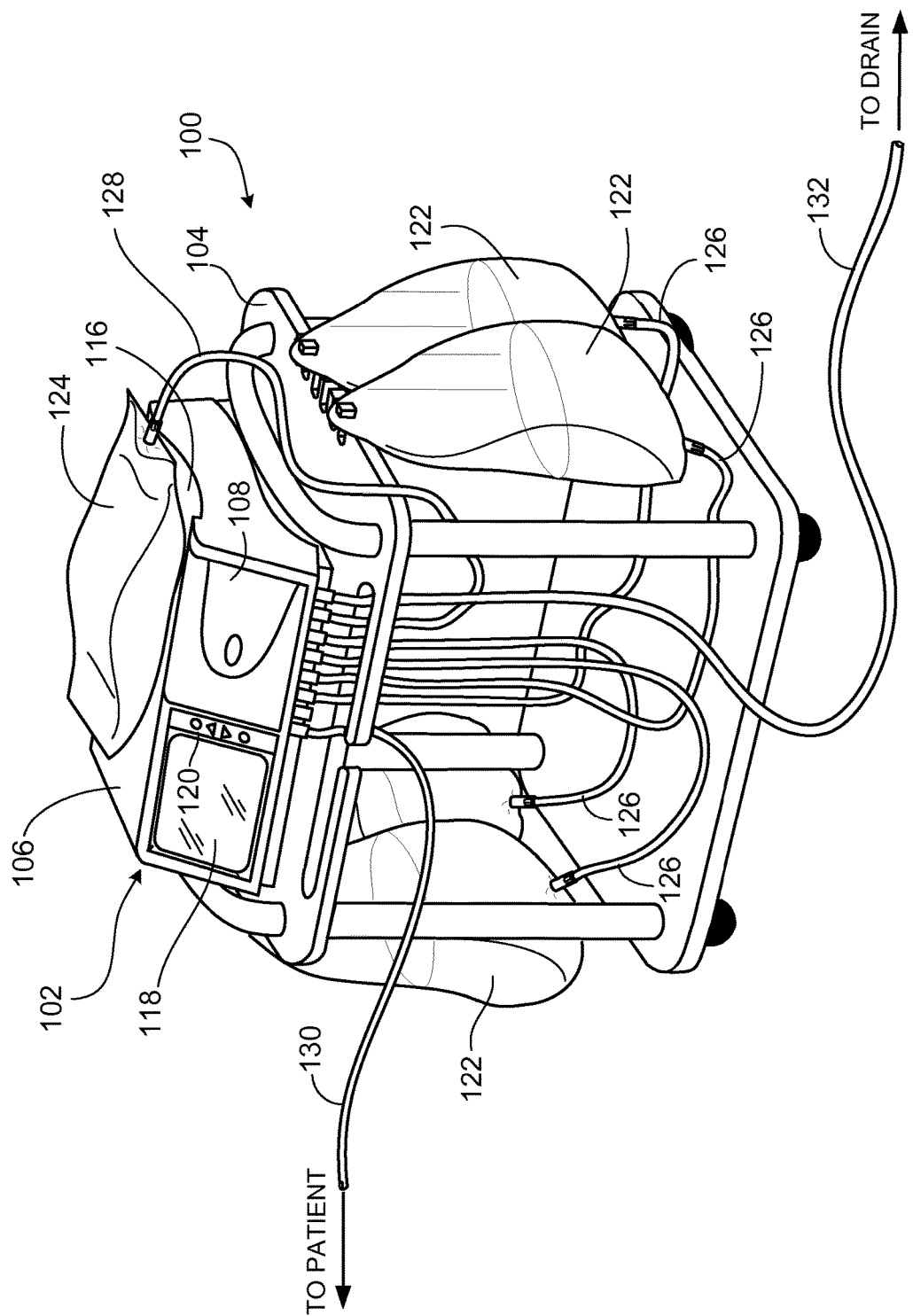
FIG. 1 is a perspective view of a peritoneal dialysis ("PD") system that includes a PD cycler positioned atop a portable cart.
Figure 2:
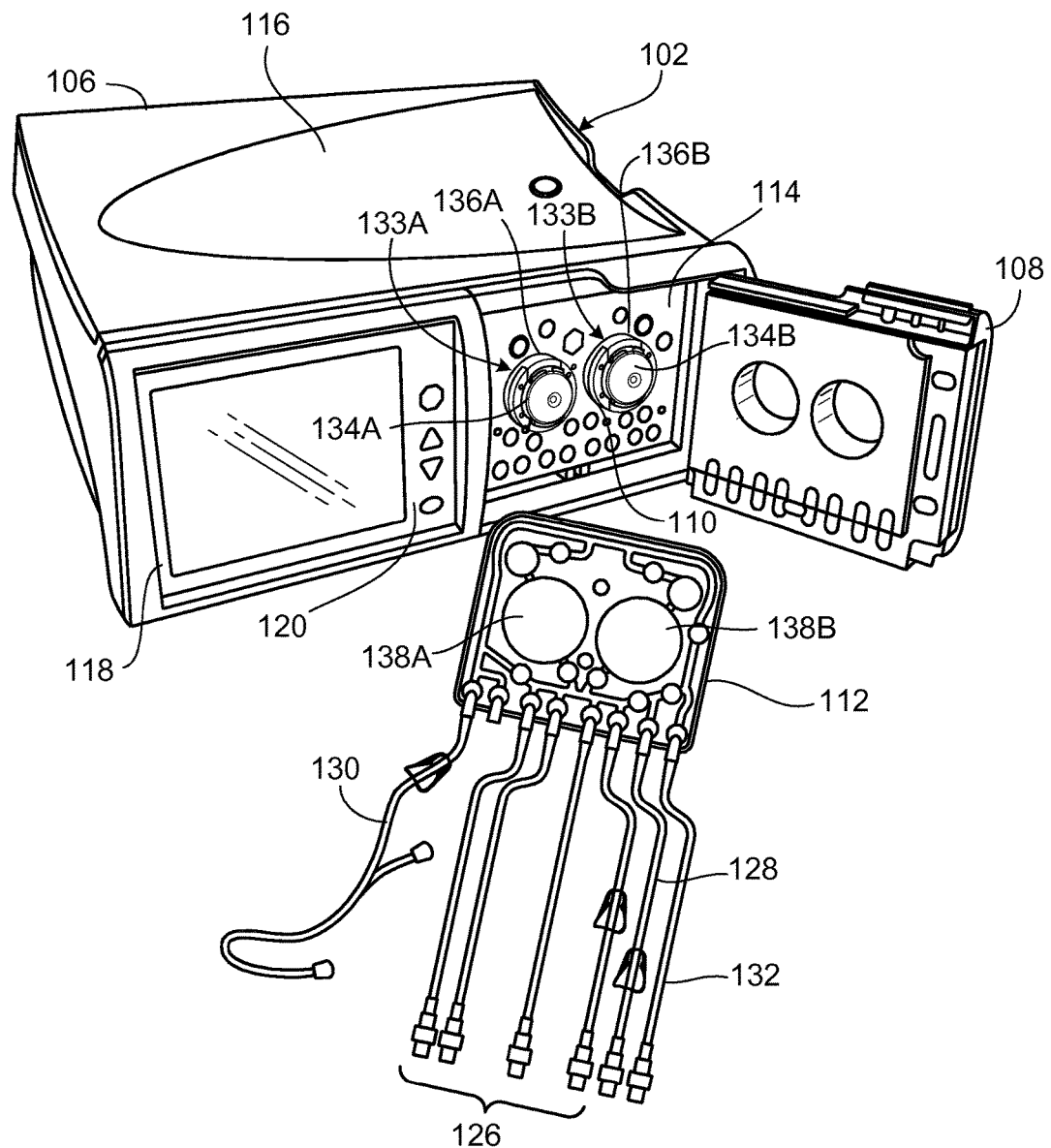
FIG. 2 is a perspective view of the PD cycler and a PD cassette of the PD system of FIG. 1. A door of the PD cycler is in the open position to show the inner surfaces of the PD cycler that interface with the PD cassette during use.

Referring to FIG. 1, a PD system 100 includes a PD cycler (also referred to as a PD machine) 102 seated on a cart 104. Referring also to FIG. 2, the PD cycler 102 includes a housing 106, a door 108, and a cassette interface 110 that abuts a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of dialysis solution (e.g., a 5 liter bag of dialysis solution). The PD cycler 102 also includes a touch screen 118 and additional control buttons 120 that can be operated by a user (e.g., a patient) to allow, for example, set-up, initiation, and/or termination of a PD treatment.

Dialysis solution bags 122 are suspended from fingers on the sides of the cart 104, and a heater bag 124 is positioned on the heater tray 116. The dialysis solution bags 122 and the heater bag 124 are connected to the cassette 112 via dialysis solution bag lines 126 and a heater bag line 128, respectively. The dialysis solution bag lines 126 can be used to pass dialysis solution from dialysis solution bags 122 to the cassette 112 during use, and the heater bag line 128 can be used to pass dialysis solution back and forth between the cassette 112 and the heater bag 124 during use. In addition, a patient line 130 and a drain line 132 are connected to the cassette 112. The patient line 130 can be connected to a patient's abdomen via a catheter and can be used to pass dialysis solution back and forth between the cassette 112 and the patient during use. The drain line 132 can be connected to a drain or drain receptacle and can be used to pass dialysis solution from the cassette 112 to the drain or drain receptacle during use.

Figure 3:
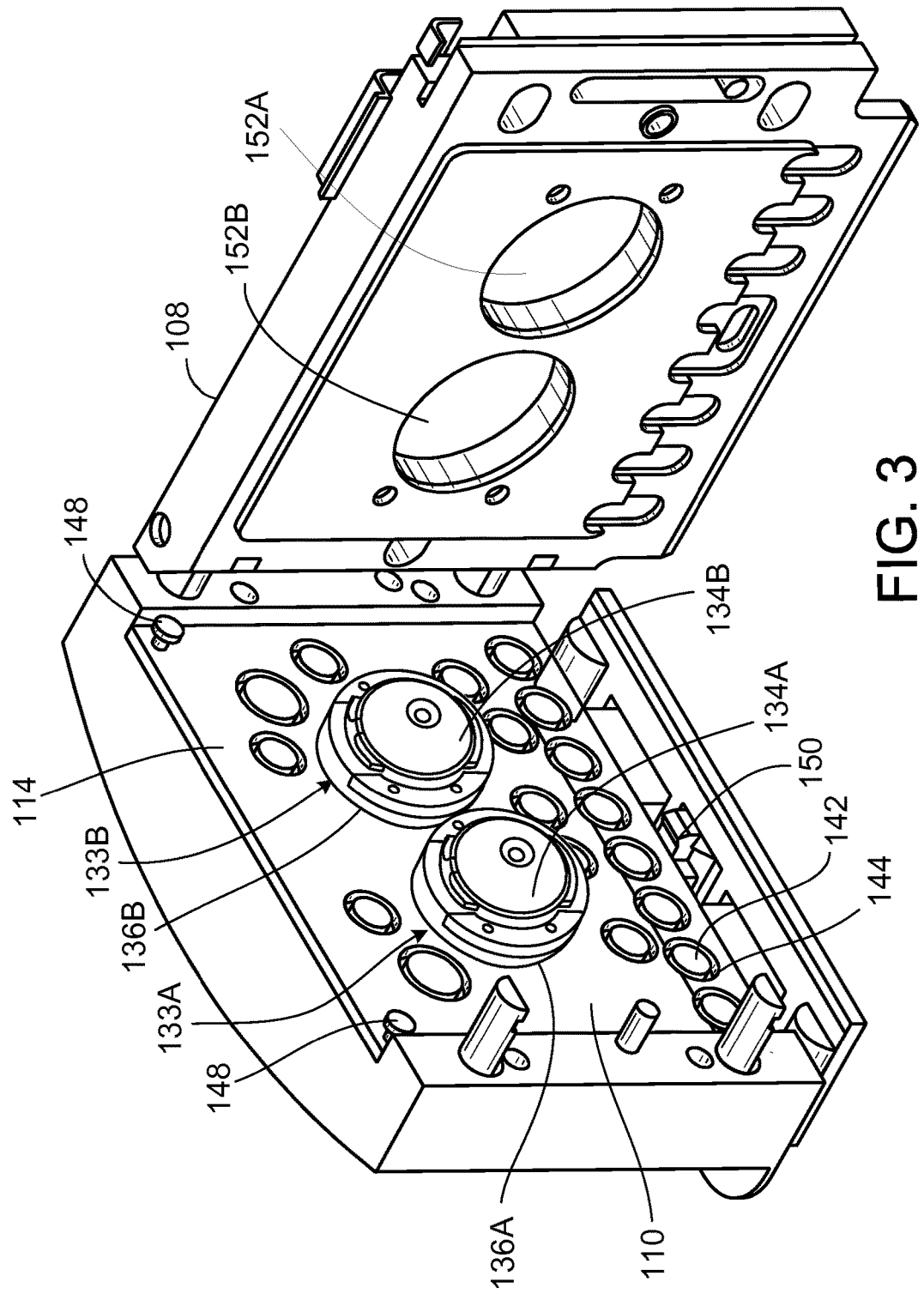
FIG. 3 is a perspective view of an open cassette compartment of the PD cycler of FIG. 1, showing, among other things, pistons having piston heads that include spring loaded latch mechanisms that can be used to mechanically connect the piston heads to associated dome-shaped members of the PD cassette.

FIG. 3 shows a more detailed view of the cassette interface 110 and the door 108 of the PD cycler 102. As shown, the PD cycler 102 includes pistons 133A, 133B with piston heads 134A, 134B attached to piston shafts 135A, 135B (piston shaft 135A shown in FIG. 4) that can be axially moved within piston access ports 136A, 136B formed in the cassette interface 110. The piston shafts 135A, 135B are connected to motors that can be operated to move the piston heads 134A, 134B axially inward and outward within the piston access ports 136A, 136B. As discussed below, when the cassette 112 (shown in FIGS. 2 and 10-13) is positioned within the cassette compartment 114 of the PD cycler 102 with the door 108 closed, the piston heads 134A, 134B of the PD cycler 102 align with pump chambers 138A, 138B of the cassette 112 such that the piston heads 134A, 134B can be mechanically connected to fastening members of the cassette 112 overlying the pump chambers 138A, 138B. As a result of this arrangement, movement of the piston heads 134A, 134B toward the cassette 112 during treatment can decrease the volume of the pump chambers 138A, 138B, and force dialysis solution out of the pump chambers 138A, 138B, while retraction of the piston heads 134A, 134B away from the cassette 112 can increase the volume of the pump chambers 138A, 138B and cause dialysis solution to be drawn into the pump chambers 138A, 138B.

Figure 4:
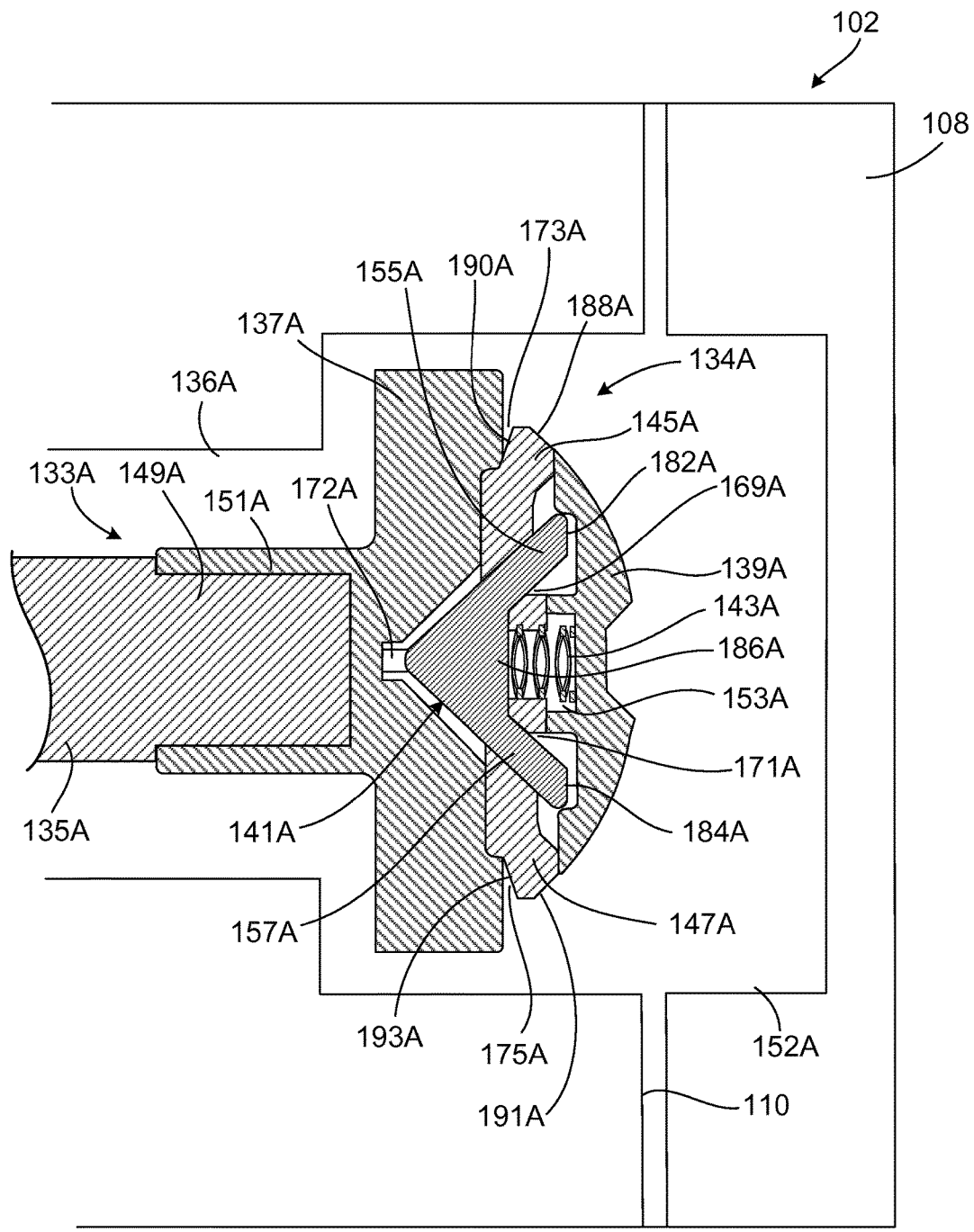
FIG. 4 is a diagrammatic cross-sectional view of the PD cycler of FIG. 1, illustrating the spring loaded latch mechanism of one of its piston heads.
Figure 5:
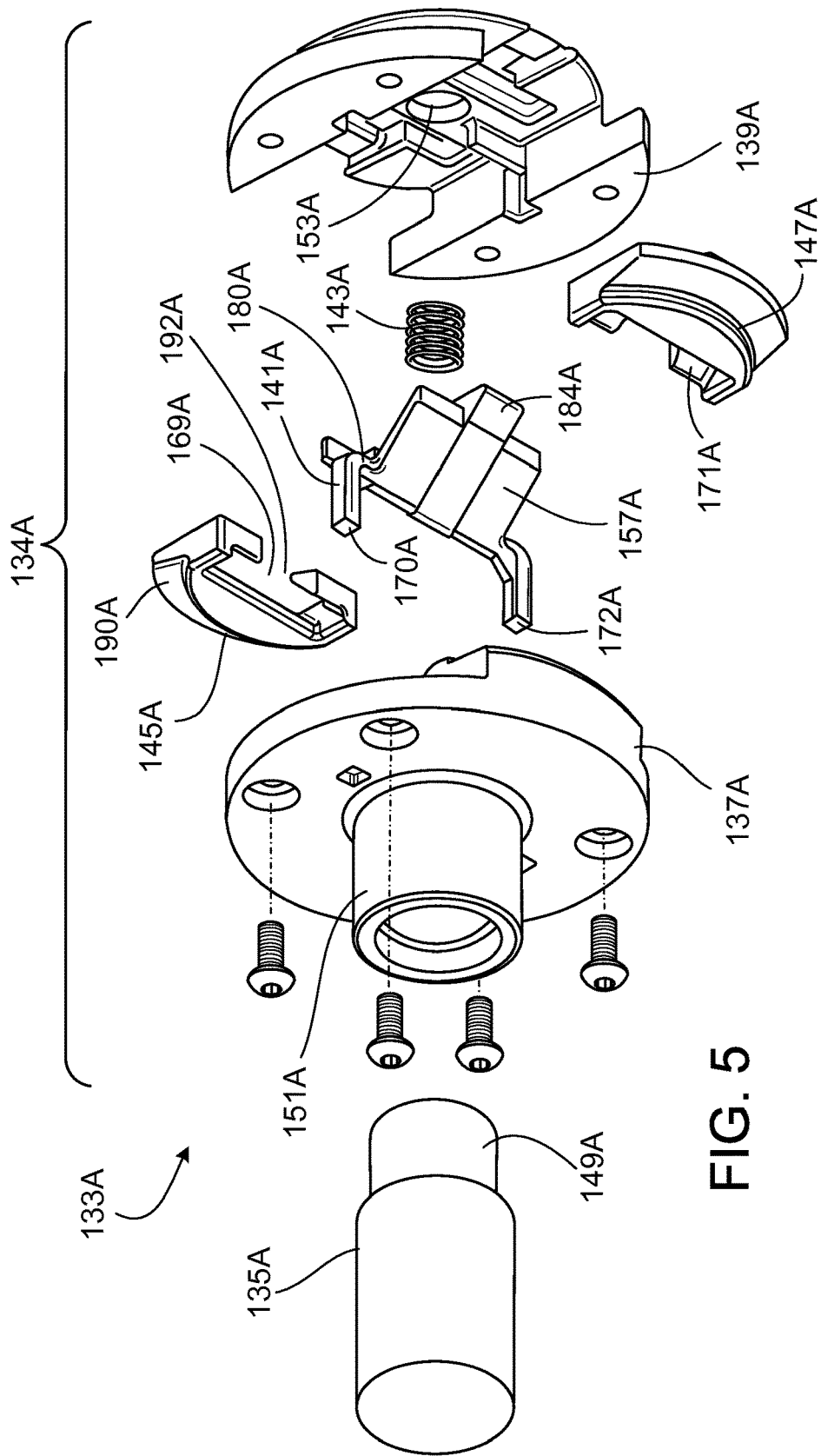
FIG. 5 is an exploded, perspective view of one of the pistons of the PD cycler of FIG. 1.

FIG. 4 is a diagrammatic cross-sectional view of the PD cycler 102, illustrating the piston 133A disposed within the piston access port 136A. FIG. 5 is an exploded, perspective view of the piston 133A. Because the pistons 133A, 133B are structurally and functionally identical, the piston 133B will not be separately described in detail. As shown in FIGS. 4 and 5, the piston 133A includes a piston shaft 135A to which the piston head 134A is attached. The piston head 134A includes a rear member 137A and a front member 139A between which a latch lock 141A, a latch lock spring 143A, and two sliding latches 145A, 147A are positioned. The rear and front members 137A, 139A are secured together to retain the latch lock 141A, the latch lock spring 143A, and the two sliding latches 145A, 147A in a contained position therebetween. Typically, the rear and front members 137A, 139A are secured together using screws. However, any of various other fastening techniques, such as riveting, welding, adhesive, etc., can alternatively or additionally be used.

The piston shaft 135A has a reduced diameter front portion 149A that is sized and shaped to fit within a bore formed in a stem 151A of the rear member 137A of the piston head 134A. Typically, the reduced diameter front portion 149A of the piston shaft 135A and the inner surface of the stem 151A have threads on their outer and inner surfaces, respectively, such that the piston head 134A can be secured to the piston shaft 135A by screwing the stem 151A onto the reduced diameter front portion 149A of the piston shaft 135A. This arrangement allows the piston head 134A to be easily removed from the piston shaft 135A for cleaning, repair, or replacement. Any of various other securement techniques, such as clipping, welding, adhesive bonding, etc., can alternatively or additionally be used to secure the piston head 134A to the piston shaft 135A.

Still referring to FIGS. 4 and 5, a front end region of the latch lock spring 143A sits within a recess 153A formed in the front member 139A of the piston head 134A, while a rear end of the spring 143A contacts a front-facing surface of the latch lock 141A. The latch lock 141A includes legs 155A, 157A that fit within slots 169A, 171A of the sliding latches 145A, 147A. The slots 169A, 171A are formed by inner and outer surfaces of the sliding latches 145A, 147A that sit adjacent to and have substantially the same angular orientation as the inner and outer surfaces, respectively, of the legs 155A, 157A.

The sliding latches 145A, 147A are slidably positioned within spaces 173A, 175A (shown in FIG. 4) formed between the rear and front members 137A, 139A. The spaces 173A, 175A are sized and shaped to allow the sliding latches 145A, 147A to slide radially inward and outward. As described in greater detail below, as the latch lock 141A moves forward relative to the front member 139A and compresses the spring 143A, the inner surfaces of the legs 155A, 157A of the latch lock 141A contact the correspondingly angled adjacent surfaces of the slide latches 145A, 147A. Due to the angles of those adjacent surfaces, the frontward movement of the latch lock 141A causes the sliding latches 145A, 147A to move radially inward. Similarly, upon applying radially inward forces to the sliding latches 145A, 147A, those surfaces of the sliding latches 145A, 147A that lie adjacent to the outer surfaces of the legs 155A, 157A of the latch lock 141A contact and apply radially inward forces to the latch lock 141A. Due to the geometry of those mating surfaces, the radially inward forces applied to the outer surfaces of the legs 155A, 157A of the latch lock 141A cause the latch lock 141A to move forward toward the front member 139A and compress the spring 143A. Upon releasing the radially inward forces being applied to the sliding latches 145A, 147A that cause the latch lock 141A to compress the spring 143A, the spring 143A will expand, causing the latch lock 141A to move rearward and the sliding latches 145A, 147A to move radially outward.

Referring to FIGS. 5-7, the latch lock 141A includes a u-shaped member 180A that forms the rearwardly extending horns 170A, 172A. The legs 155A, 157A extend frontward from the u-shaped member 180A at an acute angle relative to the longitudinal axis of the piston 133A when the piston 133A is fully assembled. Feet 182A, 184A are positioned near the front ends of the legs 155A, 157A, respectively. The feet 182A, 184A have front surfaces that are substantially perpendicular to the longitudinal axis of the piston 133A. The front surfaces of the feet 182A, 184A can contact the rear-facing surfaces of the front member 139A of the piston head 134A when the latch lock 141A is moved to its fully forward position and the spring 143A is fully compressed. The latch lock 141A also includes a projection 186A (shown in FIG. 7) that extends frontward from a central region of the u-shaped member 180A and is attached to or integrally formed with the inner surfaces of the legs 155A, 157A. The projection 186A supports the rear end of the spring 143A.

The dimensions of the piston head 134A and its various components will depend on many factors, including the type of cassette with which it is intended to be used. Referring to FIG. 6, the latch lock 141A has an overall length $L_1$, which is measured from its frontmost point to its rearmost point along the longitudinal axis of the piston 133A. The length $L_1$ can be about 0.5 inch to about 1.0 inch (e.g., 0.75 inch). An axial length $L_2$ of the portion of the latch lock 141A extending forwardly from the frontmost point of the u-shaped member 180A can be about 0.3 inch to about 0.4 inch (e.g., 0.353 inch). A length $L_3$ of the straight segment of each horn 170A, 172A can be about 0.25 inch to about 0.35 inch (e.g., 0.291 inch). A height $H_1$ of the legs 155A, 157A, measured perpendicular to the longitudinal axis of the piston 133A, can be about 0.5 inch to about 1.0 inch (e.g., 0.75 inch). A distance $D_1$ between the bottom surface of the top horn 170A and the top surface of the bottom horn 172A can be about 0.5 inch to about 1.5 inch (e.g., 0.95 inch). A distance $D_2$ between the top surface of the top horn 170A and the bottom surface of the bottom horn 172A can be about 0.75 inch to about 1.25 inch (e.g., 1.15 inch).

Referring to FIG. 7, angles $\alpha_1$ and $\alpha_2$, measured between the front surfaces of the feet 182A, 184A and the outer and inner surfaces, respectively, of the leg 157A are about 15 to about 75 degrees (e.g., about 30 to about 60 degrees, about 45 degrees). The other leg 155A of the latch lock 141A is a mirror image of the leg 157A. As noted above, the front surfaces of the feet 182A, 184A are approximately perpendicular to the longitudinal axis of the piston 133A (i.e., the horizontal axis as viewed in FIGS. 4 and 7). Thus, the outer and inner surfaces of each of the legs 155A, 157A are angled at about 15 to about 75 degrees (e.g., about 30 to about 60 degrees, about 45 degrees) relative to the longitudinal axis of the piston 133A. A distance D3 from the outer surface of the leg 155A to the outer surface of the leg 157A at the front ends of the legs 155A, 157A can be about 0.8 inch to about 1.0 inch (e.g., 0.904 inch). A thickness $T_1$ of the leg 155A, which is substantially the same as the thickness of the leg 157A, is typically slightly smaller (e.g., about 0.01 to about 0.02 inch smaller) than the slots 169A, 171A of the sliding latches 145A, 147A. The thickness $T_1$ of the leg 155A can, for example, be about 0.07 inch to about 0.14 inch (e.g., 0.113 inch).

Figure 8:
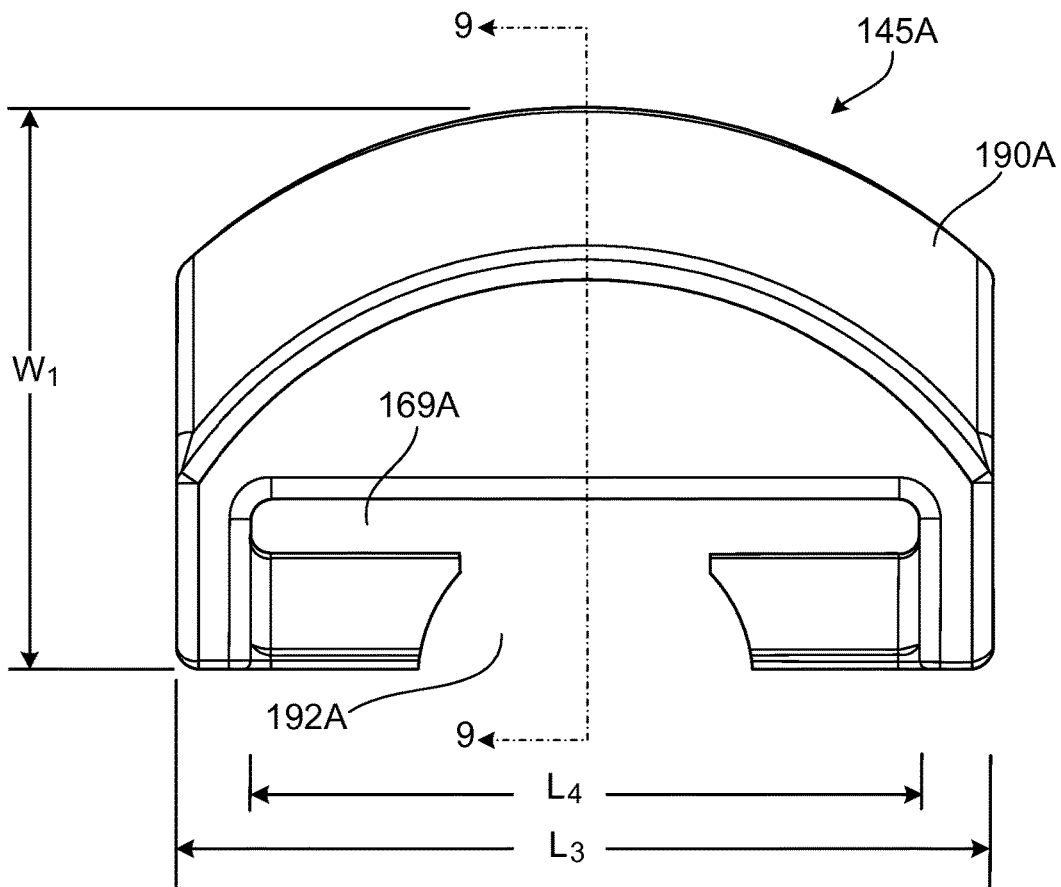
FIG. 8 is a plan view of a sliding latch of one of the piston heads of the PD cycler of FIG. 1.
Figure 9:
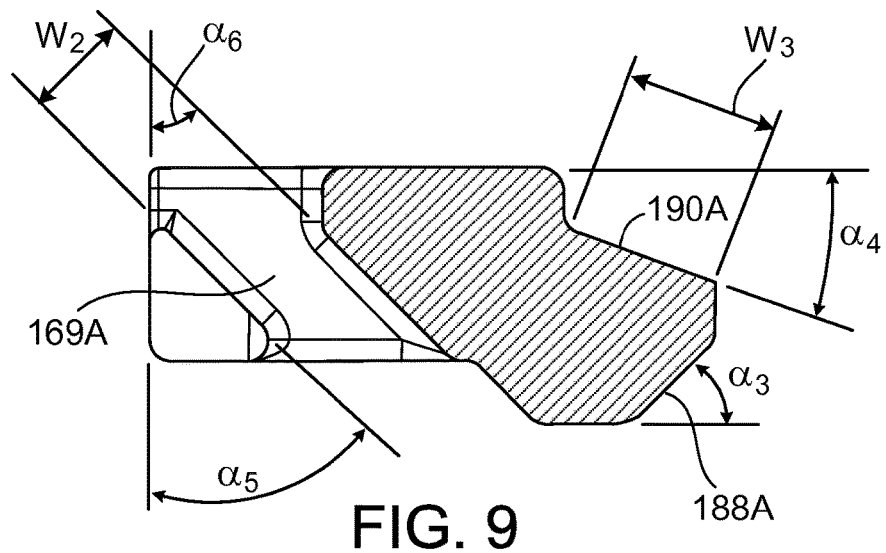
FIG. 9 is a cross-sectional view of the sliding latch, taken along line 9-9 in FIG. 8.

Referring now to FIGS. 5, 8, and 9, the sliding latch 145A includes a lead-in surface or front angled surface 188A that first contacts the dome-shaped member 161A as the piston head 134A is being mechanically connected to the dome-shaped member 161A, as described below. The sliding latch 145A also includes a lead-out surface or rear angled surface 190A that contacts the dome-shaped member 161A as the piston head 134A is being disconnected from the dome-shaped member 161A. The outer edge of the rear angled surface 190A and the outer edge of a central portion of the sliding latch 145A from which the rear angled surface 190A extends are arched. These outer edges can have radii of curvature that approximate the radius of curvature of the inner surface of the dome-shaped member 161A. The sliding latch 145A further includes a cut-out portion 192A that is located adjacent the slot 169A and is sized and shaped to receive a portion of the projection 186A extending from the latch lock 141A when the piston head 134A is fully assembled.

Referring to FIG. 8, in some implementations, the sliding latch 145A has an overall length $L_3$ of about 0.9 inch to about 1.1 inch (e.g., 0.975 inch or 0.985 inch) and/or an overall width $W_1$ of about 0.65 inch to about 0.7 inch (e.g., 0.67 inch). The slot 169A of the sliding latch 145A is typically slightly larger than the leg 155A of the latch lock 141A, which is disposed in the slot 169A when the piston head 134A is fully assembled. The slot 169A can, for example, have a length $L_4$ of about 0.7 inch to about 0.9 inch (e.g., 0.8 inch). As shown in FIG. 9, the slot 169A can have a width $W_2$ of about 0.1 inch to about 0.15 inch (e.g., 0.125 inch or 0.135 inch).

Still referring to FIG. 9, the rear angled surface 190A can have a width $W_3$ of about 0.15 inch to about 0.2 inch (e.g., 0.171 inch). The front angled surface 188A is arranged at an angle $\alpha_3$ of about 15 degrees to about 75 degrees (e.g., about 30 degrees to about 60 degrees, 45 degrees) relative to a plane that is perpendicular to the longitudinal axis of the piston 133A. Thus, the front angled surface 188A is angled at about 15 degrees to about 75 degrees (e.g., about 30 degrees to about 60 degrees, 45 degrees) relative to the longitudinal axis of the piston 133A. The rear angled surface 190A is arranged at an angle $\alpha_4$ of about 15 degrees to about 45 degrees (e.g., 20 degrees, 25 degrees, or 30 degrees) relative to a plane that is perpendicular to the longitudinal axis of the piston 133A. Thus, the rear angled surface 190A is angled at about 45 degrees to about 75 degrees (e.g., 60 degrees, 65 degrees, or 70 degrees) relative to the longitudinal axis of the piston 133A. The inner and outer surfaces of the sliding latch 145A that define the slot 169A are arranged at angles $\alpha_5$, $\alpha_6$, measured relative to the longitudinal axis of the piston 133A, that are typically approximately the same as the angles at which the inner and outer surfaces of the leg 155A of the latch lock 141A are arranged. The angles $\alpha_5$, $\alpha_6$ can, for example, be about 15 degrees to about 75 degrees (e.g., about 30 degrees to about 60 degrees, 45 degrees).

The latch lock spring 143A typically has a spring rate of about 38 pounds per inch to about 67 pounds per inch and typically provides sufficient resistance to prevent radial inward forces of about 1.5 lbf to about 9.5 lbf applied to the sliding latches 145A, 147A from compressing the spring and causing the sliding latches 145A, 147A to move radially inward.

The piston head 134A and piston shaft 135A can be formed of various different polymers, metals, and/or alloys. The rear member 137A, the front member 139A, and the latch lock 141A are typically formed of materials that are relatively rigid, resistance to wear, and have a relatively low coefficient of friction. Examples of suitable materials for these components include polyoxymethylene (e.g., Delrin), aluminum, steel, bronze, brass, and PTFE. However, other metals and plastics having relatively low coefficients of friction can alternatively or additionally be used. The sliding latches 145A, 147A are similarly typically formed of materials that are relatively rigid, resistance to wear, and have a relatively low coefficient of friction. In some implementations, the sliding latches 145A, 147A are formed of a polytetrafluoroethylene-coated 6061 aluminum alloy. Other examples of materials from which the sliding latches 145A, 147A can be formed include steel, bronze, brass, POM, and PTFE. However, it will be appreciated that certain other metals and plastics can alternatively or additionally be used.

The various components of the piston head 134A and the piston shaft 135A can be formed using any of various different techniques, including machining techniques molding techniques, and/or casting techniques.

Referring back to FIG. 3, the PD cycler 102 also includes multiple inflatable members 142 positioned within inflatable member ports 144 in the cassette interface 110. The inflatable members 142 align with depressible dome regions 146 of the cassette 112 (shown in FIGS. 10-13) when the cassette 112 is positioned within the cassette compartment 114 of the PD cycler 102. While only one of the inflatable members 142 is labeled in FIG. 3, it should be understood that the PD cycler 102 includes an inflatable member associated with each of the depressible dome regions 146 of the cassette 112. The inflatable members 142 act as valves to direct dialysis solution through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member ports 144 and out of contact with the cassette 112 when deflated. By inflating certain inflatable members 142 to depress their associated dome regions 146 on the cassette 112, certain fluid flow paths within the cassette 112 can be occluded. Thus, PD solution can be pumped through the cassette 112 by actuating the piston heads 134A, 134B, and can be guided along desired flow paths within the cassette 112 by selectively inflating and deflating the inflatable members 142.

Still referring to FIG. 3, locating pins 148 extend from the cassette interface 110 of the PD cycler 102. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a spring loaded latch 150 extending from the cassette interface 110 to allow the door 108 to be closed over the cassette 112. The locating pins 148 help to ensure that proper alignment of the cassette 112 within the cassette compartment 114 is maintained during use.

The door 108 of the PD cycler 102, as shown in FIG. 3, defines cylindrical recesses 152A, 152B that substantially align with the pistons 133A, 133B when the door 108 is in the closed position. When the cassette 112 (shown in FIGS. 10-13) is positioned within the cassette compartment 114, hollow projections 154A, 154B of the cassette 112, inner surfaces of which partially define the pump chambers 138A, 138B, fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the projections 154A, 154B of the cassette 112 and the planar surface of the door 108 supports the other regions of the cassette 112. The door 108 can counteract the forces applied by the inflatable members 142 and thus allows the inflatable members 142 to actuate the depressible dome regions 146 on the cassette 112. The engagement between the door 108 and the hollow projections 154A, 154B of the cassette 112 can also help to hold the cassette 112 in a desired fixed position within the cassette compartment 114 to further ensure that the pistons 133A, 133B align with the fluid pump chambers 138A, 138B of the cassette 112.

Figure 10:
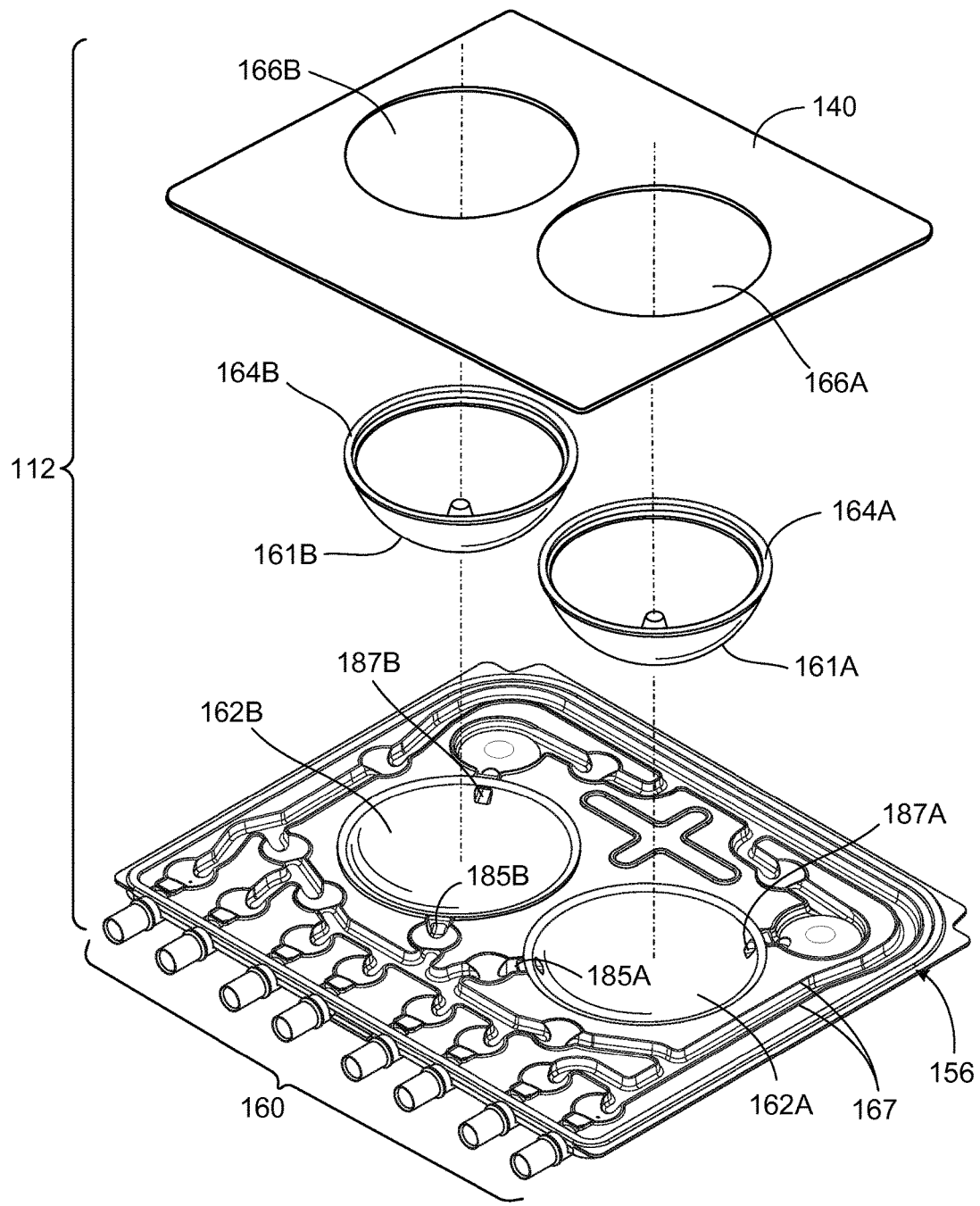
FIG. 10 is an exploded, perspective view of the PD cassette of FIG. 1, which includes dome-shaped fastening members that can be mechanically connected to the piston heads of the PD cycler of FIG. 1.
Figure 11:
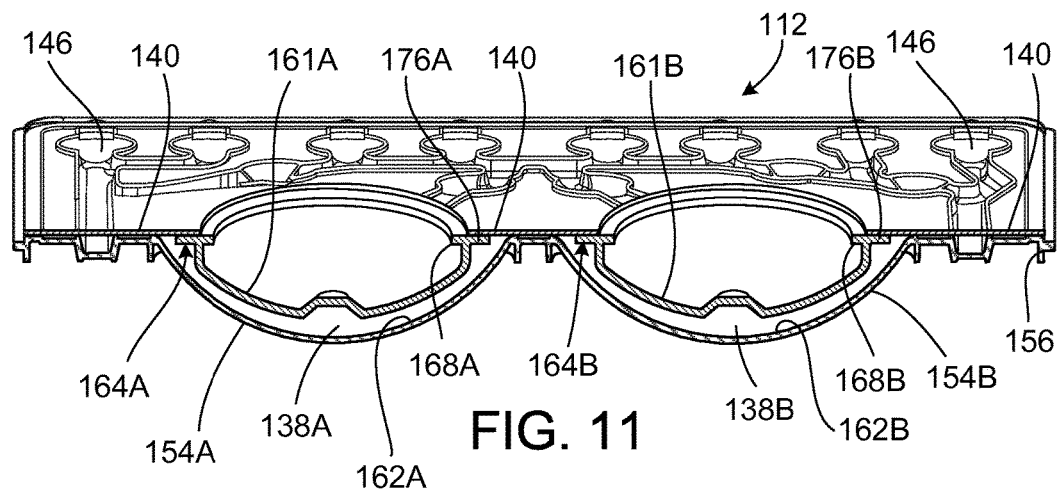
FIG. 11 is a perspective, cross-sectional view of the fully assembled PD cassette of FIG. 10.
Figure 12:
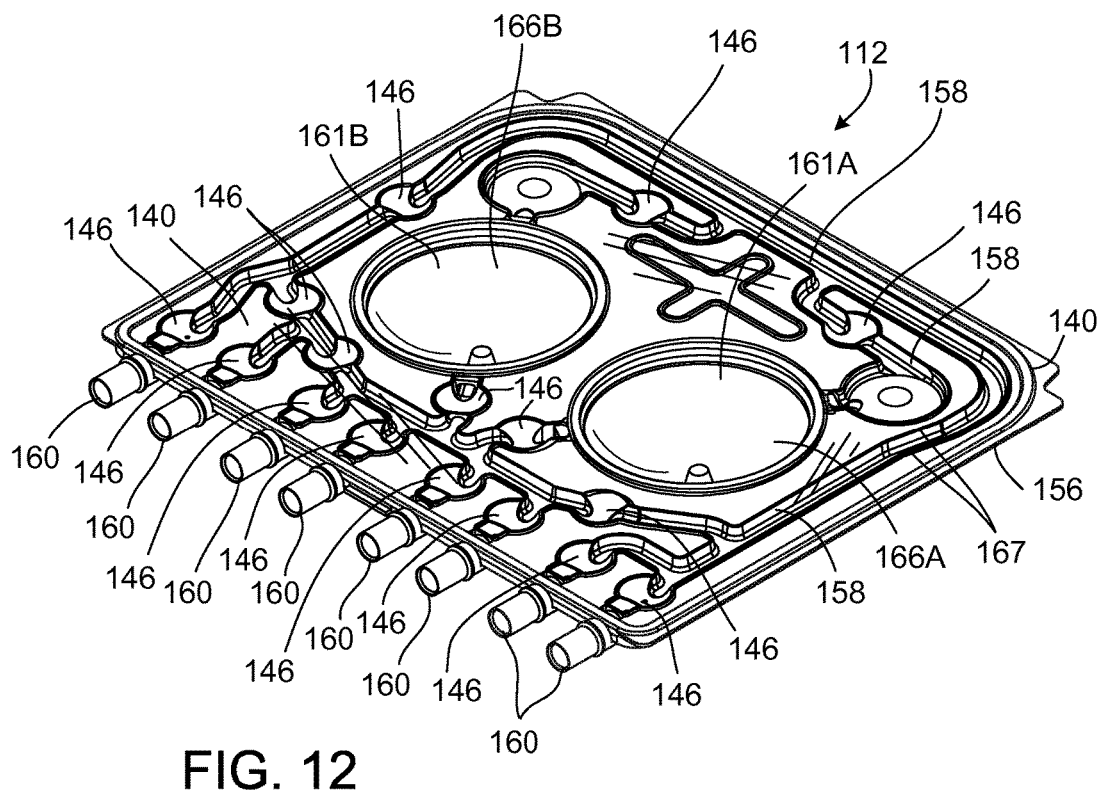
FIG. 12 is a perspective view of the fully assembled PD cassette of FIG. 10, from a flexible membrane and dome-shaped fastening member side of the PD cassette.
Figure 13:
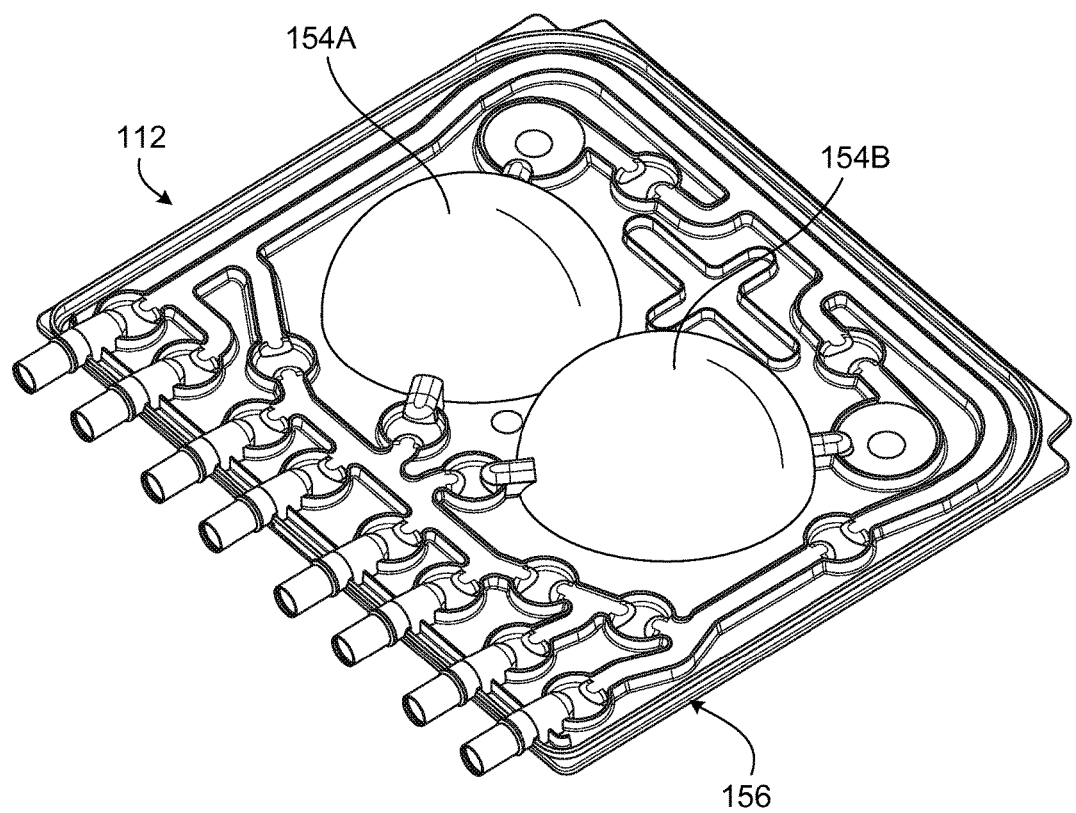
FIG. 13 is a perspective view of the fully assembled PD cassette of FIG. 10, from a rigid base side of the PD cassette.

FIG. 10 is an exploded, perspective view of the cassette 112, FIG. 11 is a perspective, cross-sectional view of the fully assembled cassette 112, and FIGS. 12 and 13 are perspective views of the assembled cassette 112, from the membrane side and from the rigid base side, respectively. Referring to FIGS. 10-12, the cassette 112 includes a flexible membrane 140 attached to a periphery of the tray-like rigid base 156. Rigid dome-shaped fastening members 161A, 161B are positioned within recessed regions 162A, 162B of the base 156. The dome-shaped members 161A, 161B are sized and shaped to receive the piston heads 134A, 134B of the PD cycler 102. In certain implementations, the dome-shaped members 161A, 161B have a diameter, measured from the outer edges of flanges 164A, 164B, of about 1.5 inches to about 2.5 inches (e.g., about 2.0 inches) and take up about two-thirds to about three-fourths of the area of the recessed regions 162A, 162B. The annular flanges 164A, 164B of the rigid dome-shaped members 161A, 161B are attached in a liquid-tight manner to portions of the inner surface of the membrane 140 surrounding substantially circular apertures 166A, 166B formed in the membrane 140. The apertures 166A, 166B expose the rigid dome-shaped members 161A, 161B such that the piston heads 134A, 134B are able to directly contact and mechanically connect to the dome-shaped members 161A, 161B during use.

The annular flanges 164A, 164B of the dome-shaped members 161A, 161B, as shown in FIG. 11, form annular projections 168A, 168B that extend radially inward and annular projections 176A, 176B that extend radially outward from the side walls of the dome-shaped members 161A, 161B. When the piston heads 134A, 134B are mechanically connected to the dome-shaped members 161A, 161B, the radially inward projections 168A, 168B engage the rear angled surfaces of the sliding latches 145A, 147A of the piston heads 134A, 134B to firmly secure the dome-shaped members 161A, 161B to the piston heads 134A, 134B. Because the membrane 140 is attached to the dome-shaped members 161A, 161B, movement of the dome-shaped members 161A, 161B into and out of the recessed regions 162A, 162B of the base 156 (e.g., due to reciprocating motion of the pistons 133A, 133B) causes the flexible membrane 140 to similarly be moved into and out of the recessed regions 162A, 162B of the base 156. This movement allows fluid to be forced out of and drawn into the fluid pump chambers 138A, 138B, which are formed between the recessed regions 162A, 162B of the base 156 and the portions of the dome-shaped members 161A, 161B and membrane 140 that overlie those recessed regions 162A, 162B.

Referring to FIGS. 10 and 12, raised ridges 167 extend from the substantially planar surface of the base 156 towards and into contact with the inner surface of the flexible membrane 140 when the cassette 112 is compressed between the door 108 and the cassette interface 110 of the PD cycler 102 to form a series of fluid passageways 158 and to form the multiple, depressible dome regions 146, which are widened portions (e.g., substantially circular widened portions) of the fluid pathways 158, as shown in FIG. 12. The fluid passageways 158 fluidly connect the fluid line connectors 160 of the cassette 112, which act as inlet/outlet ports of the cassette 112, to the fluid pump chambers 138A, 138B. As noted above, the various inflatable valve members 142 of the PD cycler 102 act on the cassette 112 during use. During use, the dialysis solution flows to and from the pump chambers 138A, 138B through the fluid pathways 158 and dome regions 146. At each depressible dome region 146, the membrane 140 can be deflected to contact the planar surface of the base 156 from which the raised ridges 167 extend. Such contact can substantially impede (e.g., prevent) the flow of dialysis solution along the region of the pathway 158 associated with that dome region 146. Thus, the flow of dialysis solution through the cassette 112 can be controlled through the selective depression of the depressible dome regions 146 by selectively inflating the inflatable members 142 of the PD cycler 102.

Still referring to FIGS. 10 and 12, the fluid line connectors 160 are positioned along the bottom edge of the cassette 112. As noted above, the fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysis solution bag lines 126, the heater bag line 128, the patient line 130, and the drain line 132. One end of the fitting can be inserted into and bonded to its respective line and the other end can be inserted into and bonded to its associated connector 160. By permitting the dialysis solution bag lines 126, the heater bag line 128, the patient line 130, and the drain line 132 to be connected to the cassette, as shown in FIGS. 1 and 2, the connectors 160 allow dialysis solution to flow into and out of the cassette 112 during use.

The rigidity of the base 156 helps to hold the cassette 112 in place within the cassette compartment 114 of the PD cycler 102 and to prevent the base 156 from flexing and deforming in response to forces applied to the projections 154A, 154B by the dome-shaped members 161A, 161B and in response to forces applied to the planar surface of the base 156 by the inflatable members 142.

The base 156 and the dome-shaped members 161A, 161B of the cassette 112 can be formed of any of various relatively rigid materials. In some implementations, these components of the cassette 112 are formed of one or more polymers, such as polypropylene, polyvinyl chloride, polycarbonate, polysulfone, and other medical grade plastic materials. In certain implementations, these components can be formed of one or more metals or alloys, such as stainless steel. These components of can alternatively be formed of various different combinations of the above-noted polymers and metals. These components of the cassette 112 can be formed using any of various different techniques, including machining, molding, and casting techniques.

As noted above, the membrane 140 is attached to the periphery of the base 156 and to the annular flanges 164A, 164B of the dome-shaped members 161A, 161B. The portion of the membrane 140 overlying the remaining portions of the base 156 are typically not attached to the base 156. Rather, these portions of the membrane 140 sit loosely atop the raised ridges 165A, 165B, and 167 extending from the planar surface of the base 156. Any of various attachment techniques, such as adhesive bonding and thermal bonding, can be used to attach the membrane 140 to the periphery of the base 156 and to the dome-shaped members. The thickness and material(s) of the membrane 140 are selected so that the membrane 140 has sufficient flexibility to flex toward the base 156 in response to the force applied to the membrane 140 by the inflatable members 142. In certain implementations, the membrane 140 is about 0.100 micron to about 0.150 micron in thickness. However, various other thicknesses may be sufficient depending on the type of material used to form the membrane 140.

Any of various different materials that permit the membrane 140 to deflect in response to movement of the inflatable members 142 without tearing can be used to form the membrane 140. In some implementations, the membrane 140 includes a three-layer laminate. In certain implementations, for example, inner and outer layers of the laminate are formed of a compound that is made up of 60 percent Septon® 8004 thermoplastic rubber (i.e., hydrogenated styrenic block copolymer) and 40 percent ethylene, and a middle layer is formed of a compound that is made up of 25 percent Tuftec® H1062 (SEBS: hydrogenated styrenic thermoplastic elastomer), 40 percent Engage® 8003 polyolefin elastomer (ethylene octene copolymer), and 35 percent Septon® 8004 thermoplastic rubber (i.e., hydrogenated styrenic block copolymer). The membrane can alternatively include more or fewer layers and/or can be formed of different materials.

Figure 14:
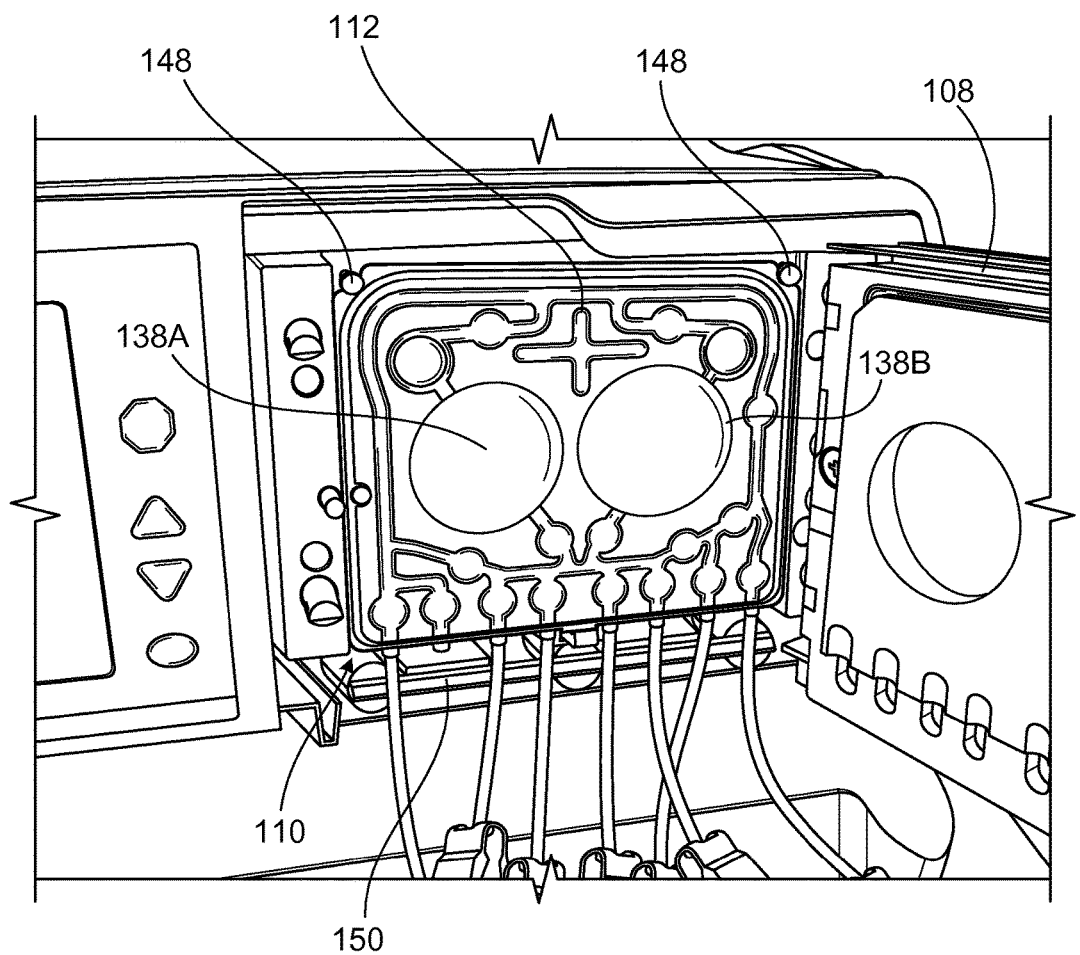
FIG. 14 is a partial perspective view of the PD cassette in the cassette compartment of the PD cycler of the PD system of FIG. 1.

As shown in FIG. 14, before treatment, the door 108 of the PD cycler 102 is opened to expose the cassette interface 110, and the cassette 112 is positioned with its dome-shaped members 161A, 161B aligned with the pistons 133A, 133B of the PD cycler 102 and with its membrane 140 adjacent to the cassette interface 110. In order to ensure that the dome-shaped members 161A, 161B align with the pistons 133A, 133B, the cassette 112 is positioned between the locating pins 148 and the spring loaded latch 150 extending from the cassette interface 110. The asymmetrically positioned connectors 160 of the cassette act as a keying feature that reduces the likelihood that the cassette 112 will be installed with the membrane 140 and dome-shaped members 161A, 161B facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward toward the door 108. The pistons 133A, 133B are typically retracted into the piston access ports 136A, 136B during installation of the cassette 112 to avoid interference between pistons 133A, 133B and the dome-shaped members 161A, 161B and thus increase the ease with which the cassette 112 can be positioned within the cassette compartment 114.

FIGS. 15A-15F are diagrammatic cross-sectional views of the PD system 100 with the PD cassette 112 disposed in the cassette compartment 114 of the PD cycler 102, during different phases of a pumping operation used to draw dialysis solution into the pump chamber 138A and to force dialysis solution out of the pump chamber 138A. The technique for pumping solution to and from the other pump chamber 138B is identical and thus is not separately described in detail.

Figure 15A:
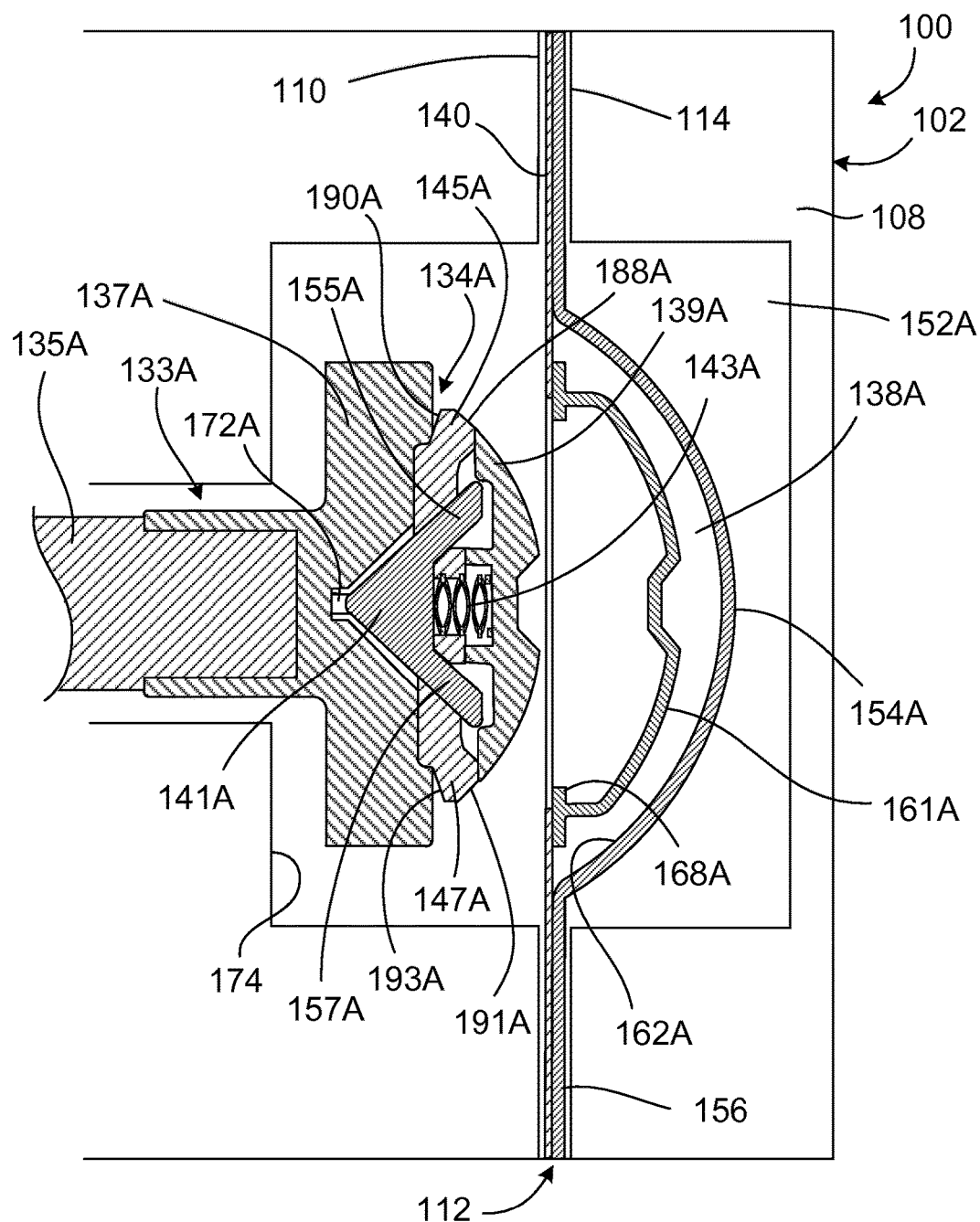
FIGS. 15A-15F are diagrammatic cross-sectional views of the PD system of FIG. 1 with the PD cassette disposed in the cassette compartment of the PD cycler, during different phases of a pumping operation.

FIG. 15A shows the cassette 112 positioned within the cassette compartment 114 shortly after installation. As shown, the cassette 112 is positioned adjacent to the cassette interface 110 and the door 108 is closed over the cassette 112 such that the cassette 112 is contained within the cassette compartment 114 between the door 108 and the cassette interface 110. The piston head 134A is retracted into the piston access port 136A such that the piston head 134A does not interfere with the cassette 112 during its installation. With the cassette 112 positioned in the cassette compartment 114, the inflatable pad within the door 108 is inflated to compress the cassette 112 between the door 108 and the cassette interface 110. This compression of the cassette 112 holds the projection 154A of the cassette 112 in the recess 152A of the door 108 and presses the membrane 140 tightly against the raised ridges 167 extending from the planar surface of the rigid base 156 to form the enclosed fluid pathways 158 and dome regions 146 (shown in FIG. 12).

Figure 15B:
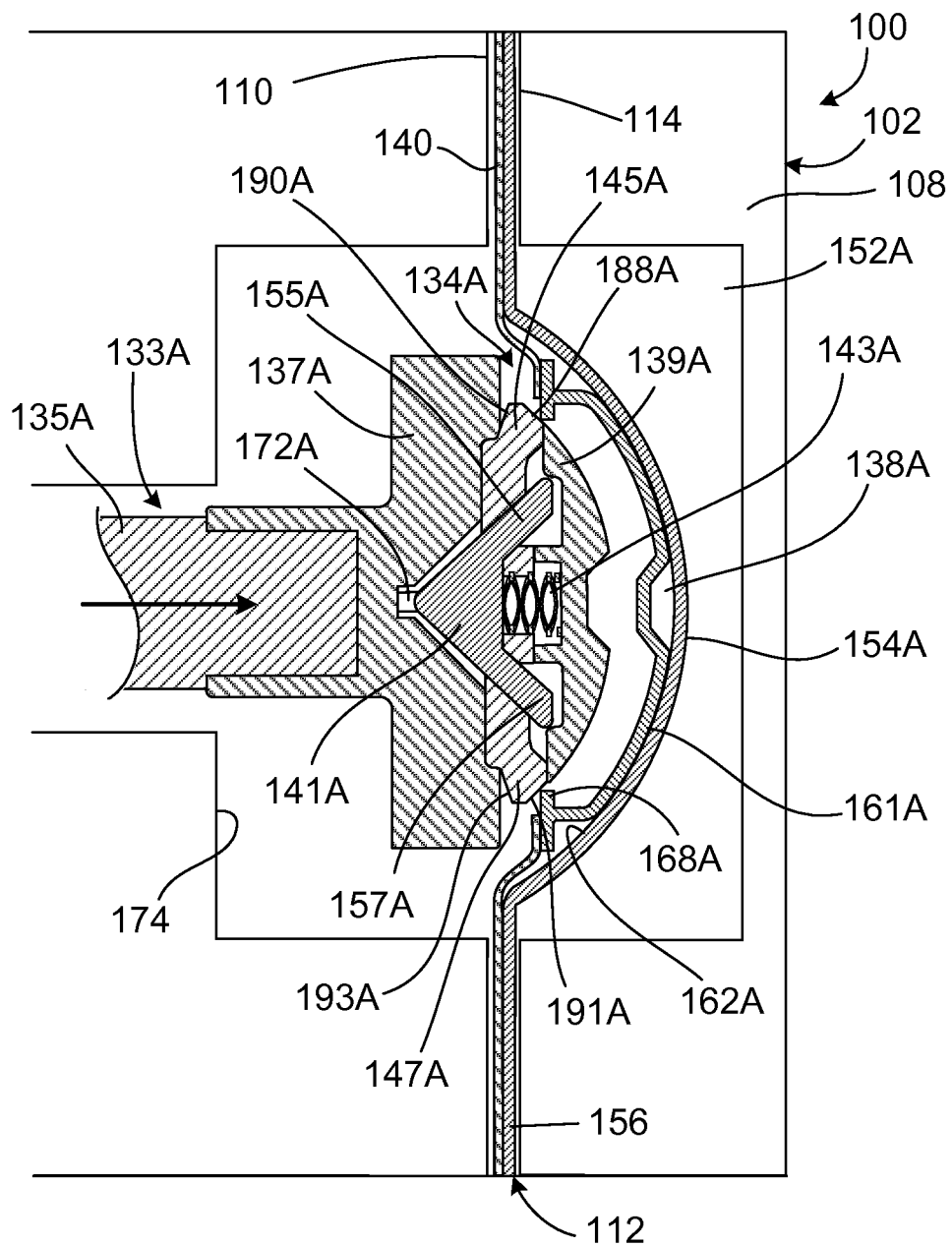

As shown in FIG. 15B, once the cassette 112 has been installed within the cassette compartment 114 of the PD cycler 102, the piston 133A is advanced to initiate the process of mechanically connecting the piston head 134A of the PD cycler 102 to the dome-shaped member 161A of the cassette 112. The piston 133A can be advanced at a rate of about 0.8 inch/minute to about 11 inches/minute and with an axial force of about 5.0 lbf to about 50 lbf. As the piston 133A is advanced, the front angled surface 188A of the sliding latch 145A and a front angled surface 191A of the sliding latch 147A contact a rear surface of the annular projection 168A, which extends radially inward from the dome-shaped member 161A. The rear surface of the annular projection 168A is approximately perpendicular to the longitudinal axis of the piston 133A.

As the piston 133A continues to advance, the dome-shaped member 161A contacts the inner surface of the portion of the rigid base 156 that forms the recessed region 162A, as shown in FIG. 15B. The rigid base 156 prevents further forward movement of the dome-shaped member 161A. The membrane 140, which is attached to the peripheral flange 164A of the dome-shaped member 161A, also stretches and moves into the recessed region 162A due to the advancing piston 133A. Due to the angled geometries of the front angled surfaces 188A, 191A of the sliding latches 145A, 147A and the resistance provided by the rigid base 156 to the forward motion of the dome-shaped member 161A, the sliding latches 145A, 147A are caused to move radially inward (i.e., toward the longitudinal axis of the piston 133A) as the piston head 134A continues to be advanced relative to the dome-shaped member 161A. More specifically, the forward motion of the sliding latches 145A, 147A is converted into a combined forward and radially inward motion due to the sliding motion of the front angled surfaces 188A, 191A of the sliding latches 145A, 147A against the rear surface of the annular projection 168A of the dome-shaped member 161A. The radial inward movement of each of the sliding latches 145A, 147A in turn causes a forward movement of the latch lock 141A due to the mated geometries of the outer surfaces of the legs 155A, 157A of the latch lock 141A and the surfaces of the sliding latches 145A, 147A that are positioned adjacent to and brought into contact with those outer surfaces of the legs 155A, 157A. This forward movement of the latch lock 141A is resisted by the spring 143A.

Figure 15C:
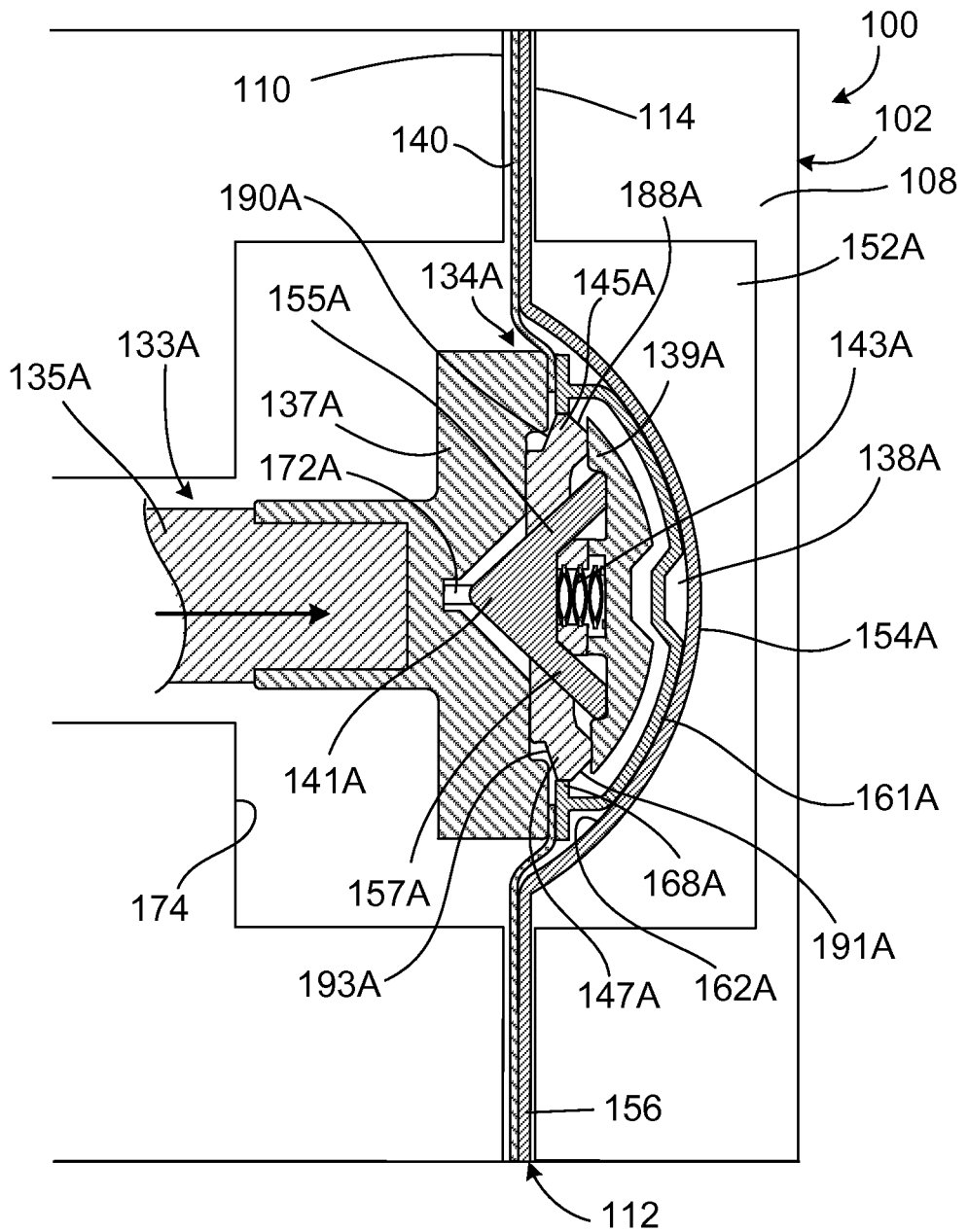

FIG. 15C shows the piston head 134A at a point during the connection process at which the sliding latches 145A, 147A have been deflected radially inward a sufficient distance to allow the sliding latches 145A, 147A to pass beyond the annular projection 168A that extends radially inward from the dome-shaped member 161A. In this position, outer peripheral surfaces of the sliding latches 145A, 147A, which are substantially parallel to the longitudinal axis of the piston 133A, contact and slide along an inner surface of the projection 168A of the dome-shaped member 161A, which is also substantially parallel to the longitudinal axis of the piston 133A. The spring 143A is further compressed due to the radially inwardly deflected positions of the sliding latches 145A, 147A.

Figure 15D:
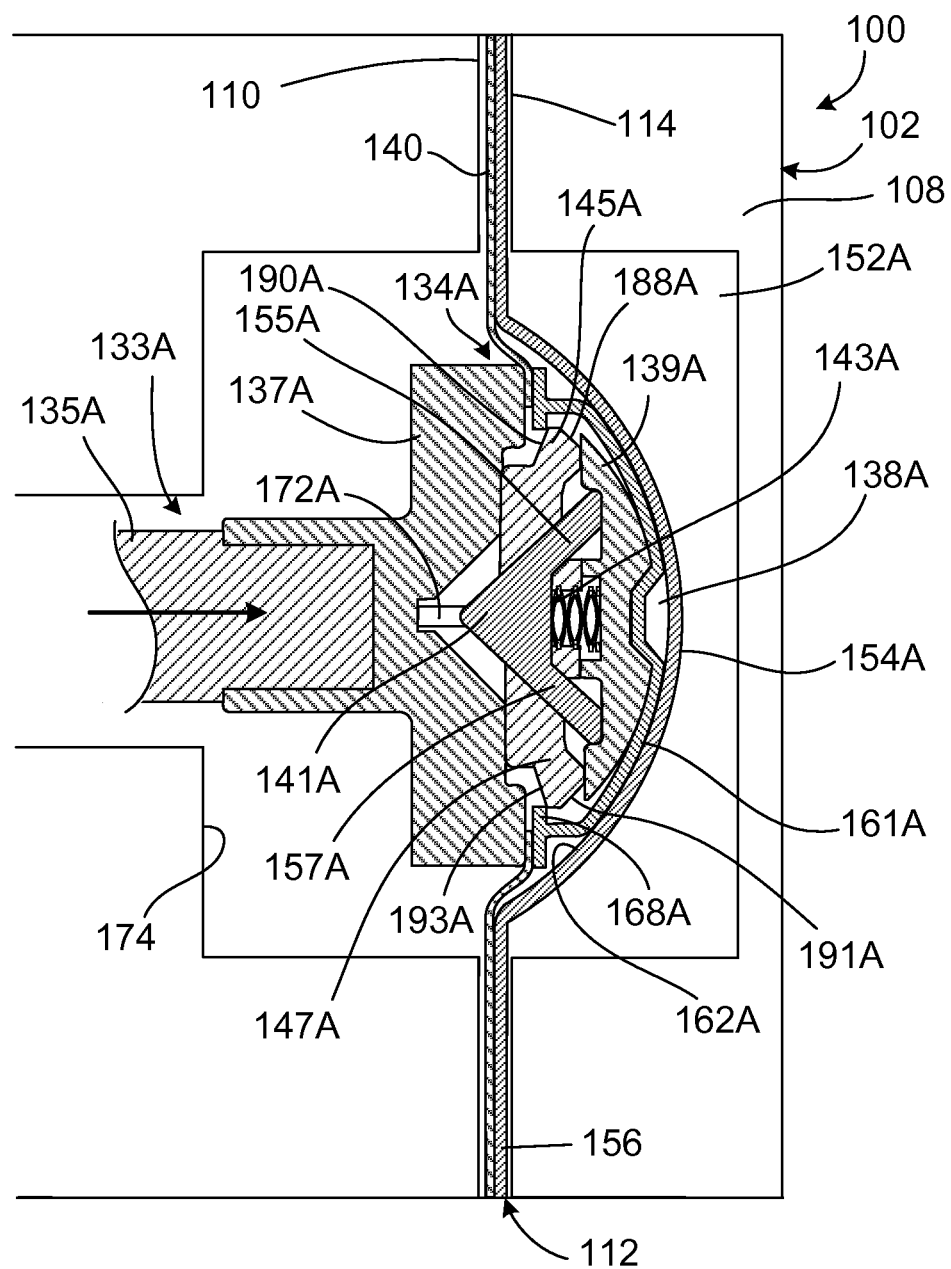

Referring to FIG. 15D, as the sliding latches 145A, 147A pass beyond the projection 168A, the spring 143A is allowed to expand. The expansion of the spring 143A causes the latch lock 141A to move rearward. As a result, the outer surfaces of the legs 155A, 157A of the latch lock 141A contact the correspondingly angled adjacent surfaces of the sliding latches 145A, 147A, causing the sliding latches 145A, 147A to move radially outward underneath the projection 168A of the dome-shaped member 161A. The rear angled surfaces 190A, 193A of the sliding latches 145A, 147A ride along the front surface of the projection 168A of the dome-shaped member 161A, which is slightly angled toward the rear of the dome-shaped member 161A (e.g., angled at about 88 degrees relative to the longitudinal axis of the piston head 133A), as the sliding latches 145A, 147A move radially outward. The sliding latches 145A, 147A become wedged beneath the projection 168A as the sliding latches 145A, 147A move radially outward.

The rear angled surfaces 190A, 193A of the sliding latches 145A, 147A permit the piston head 134A to be firmly locked within dome-shaped members of slightly different sizes. For example, due to imperfect manufacturing techniques, the thickness of the annular projection 168A along the longitudinal axis of the piston 133A may differ slightly (e.g., by about 0.003 to about 0.005 inch) amongst different molded dome-shaped members. The rear angled surfaces of the sliding latches 145A, 147A can help to ensure that a tight fit is achieved with any of those dome-shaped members.

Figure 15E:
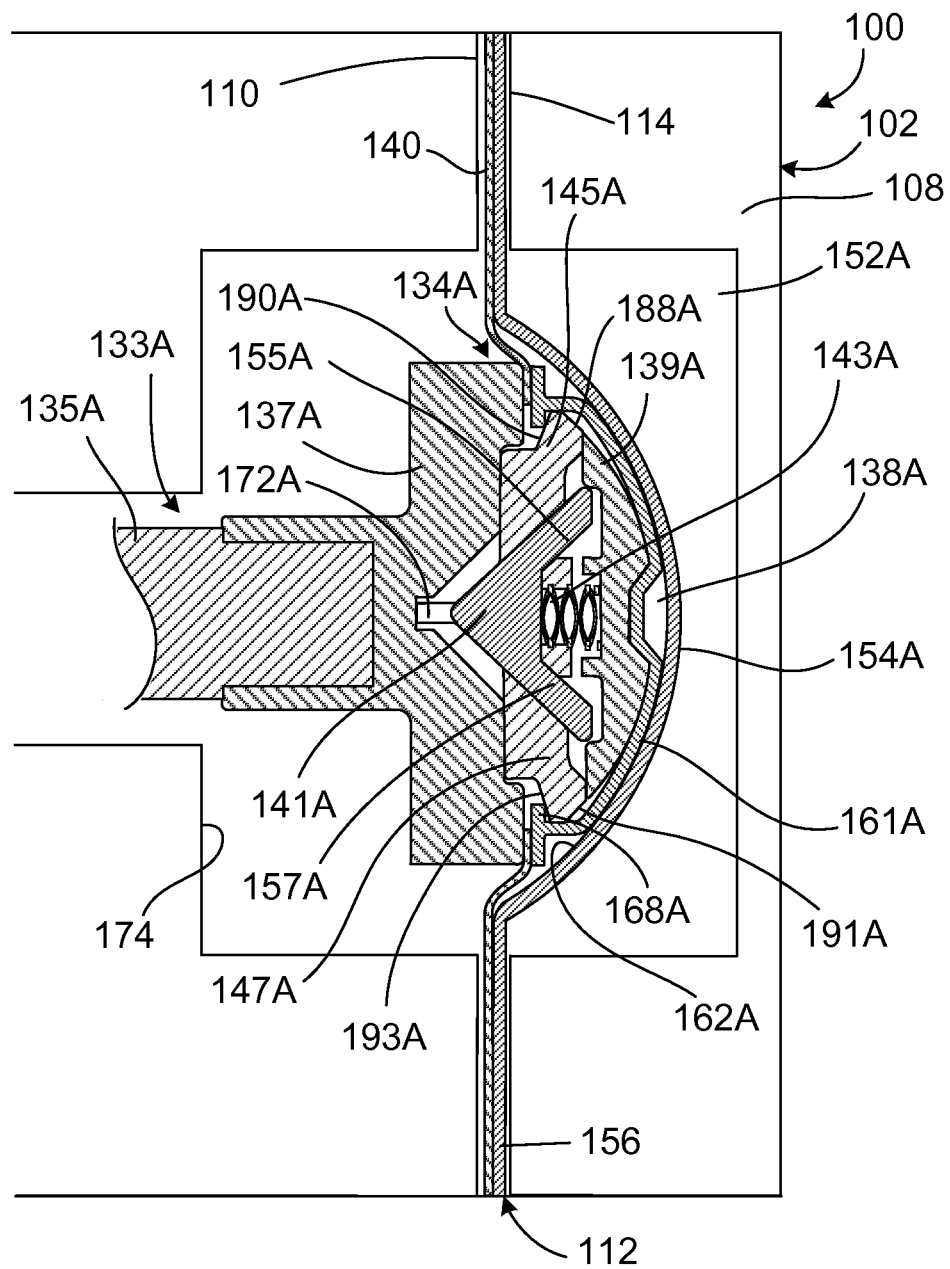

FIG. 15E illustrates the complete mechanical connection between the piston head 134A and the dome-shaped member 161A in which the sliding latches 145A, 147A have moved to maximum outwardly displaced positions within the dome-shaped member 161A. In this configuration, the projection 168A of the dome-shaped member 161A is effectively pinched between the rear member 137A of the piston head 134A and the sliding latches 145A, 147A, resulting in a secure engagement between the piston head 134A and the dome-shaped member 161A. As a result of the secure engagement of the piston head 134A to the dome-shaped member 161A, the amount of slippage of the piston head 134A relative to the dome-shaped member 161A can be reduced (e.g., minimized) and thus precise pumping can be achieved.

As discussed above, as the piston 133A is being mechanically connected to the dome-shaped member 161A, the dome-shaped member 161A is advanced into the recessed region 162A of the rigid base 156 until the dome-shaped member 161A contacts the inner surface of the recessed region 162A of the base 156 of the cassette 112. This movement decreases the volume of the pump chamber 138A formed between the dome-shaped member 161A, the membrane 140, and the recessed region of the base 156, and thus causes any fluid (e.g., priming fluid) within the pump chamber 138A to be forced out of the pump chamber 138A from the fluid pathways 158 of the cassette via the inlet port 185A (shown in FIG. 10).

Figure 15F:
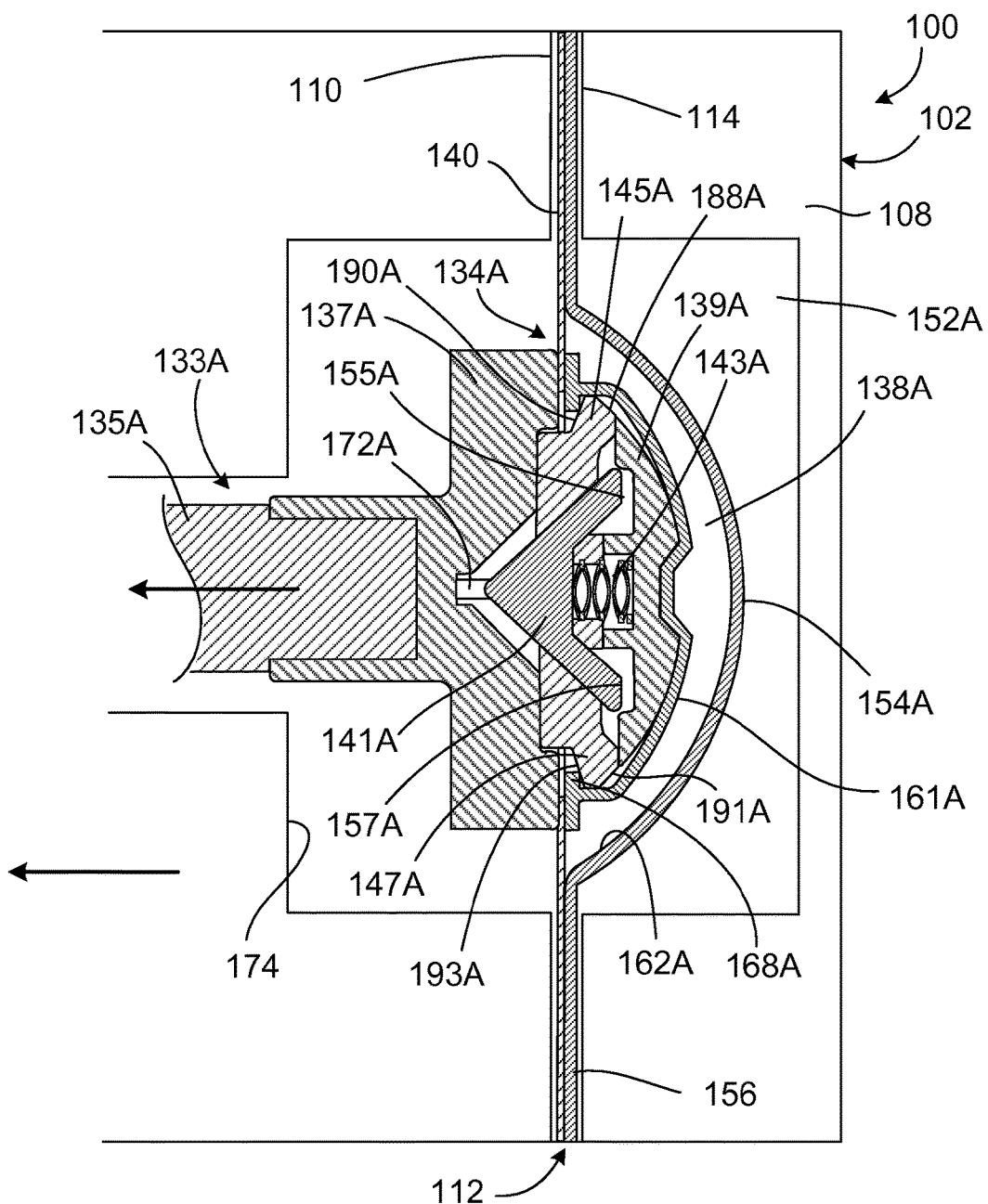

Referring to FIG. 15F, after the piston 133A has been mechanically connected to the dome-shaped member 161A, the piston 133A is retracted to draw dialysis solution into the pump chamber 138A. Because the piston head 134A is mechanically connected to the dome-shaped member 161A and the dome-shaped member 161A is attached to the membrane 140 of the cassette 112, the retraction of the piston 133A causes the dome-shaped member 161A and the portion of the membrane 140 attached to the dome-shaped member 161A to move rearwardly. As a result, the volume of the pump chamber 138A is increased and fluid is drawn into the pump chamber 138A.

Because the volumes of the fluid pump chamber 138A and the piston head 134A are known, the linear distance travelled by the piston 133A can be used to determine the volume of dialysis solution drawn into the fluid pump chamber 138A. The linear distance travelled by the piston 133A can be determined based on the number of revolutions or steps of the motor (e.g., stepper motor) used to drive the piston 133A. Thus, the volume of solution drawn into the fluid pump chamber 138A can be determined based on the number of revolutions or steps of the motor. The tight fit between the piston head 134A and the dome-shaped member 161A ensure the accuracy of the volume of solution determined in this manner.

After drawing the dialysis solution into the pump chamber 138A, the dialysis solution is forced out of the pump chamber 138A by again advancing the piston 133A and decreasing the volume of the pump chamber 138A. The piston 133A is typically advanced until the dome-shaped member 161A contacts or nearly contacts the inner surface of the recessed region of the base 156 so that substantially all of the dialysis solution is forced out of the fluid pump chamber 138A via the outlet port 187A (shown in FIG. 10).

This process of drawing dialysis solution into the fluid pump chamber 138A and then forcing the dialysis solution out of the fluid pump chamber 138A is repeated until a desired volume of dialysis solution has been pumped to or from a location (e.g., to or from the patient).

As noted above, while forcing dialysis solution into and out of the pump chambers 138A, 138B, certain inflatable members 142 of the PD cycler 102 can be selectively inflated to direct the pumped dialysis solution along desired pathways in the cassette 112.

Referring back to FIGS. 1 and 2, during PD treatment, the patient line 130 is connected to a patient's abdomen via a catheter, and the drain line 132 is connected to a drain or drain receptacle. The PD treatment typically begins by emptying the patient of spent dialysis solution that remains in the patient's abdomen from the previous treatment. To do this, the pump of the PD cycler 102 is activated to cause the pistons 133A, 133B to reciprocate and selected inflatable members 142 are inflated to cause the spent dialysis solution to be drawn into the fluid pump chambers 138A, 138B of the cassette 112 from the patient. The spent dialysis solution is then pumped from the fluid pump chambers 138A, 138B to the drain via the drain line 132.

After draining the spent dialysis solution from the patient, heated dialysis solution is transferred from the heater bag 124 to the patient. To do this, the motor or motors of the PD cycler 102 is/are activated to cause the pistons 133A, 133B to reciprocate and certain inflatable members 142 of the PD cycler 102 are inflated to cause the warmed dialysis solution to be drawn into the fluid pump chambers 138A, 138B of the cassette 112 from the heater bag 124 via the heater bag line 128. The warmed dialysis solution is then pumped from the fluid pump chambers 138A, 138B to the patient via the patient line 130.

Once the dialysis solution has been pumped from the heater bag 124 to the patient, the dialysis solution is allowed to dwell within the patient for a period of time. During this dwell period, toxins cross the peritoneum of the patient into the dialysis solution from the patient's blood. As the dialysis solution dwells within the patient, the PD cycler 102 prepares fresh dialysate for delivery to the patient in a subsequent cycle. In particular, the PD cycler 102 pumps fresh dialysis solution from one of the four full dialysis solution bags 122 into the heater bag 124 for heating. To do this, the pump of the PD cycler 102 is activated to cause the pistons 133A, 133B to reciprocate and certain inflatable members 142 of the PD cycler 102 are inflated to cause the dialysis solution to be drawn into the fluid pump chambers 138A, 138B of the cassette 112 from the selected dialysis solution bag 122 via its associated line 126. The dialysis solution is then pumped from the fluid pump chambers 138A, 138B to the heater bag 124 via the heater bag line 128.

After the dialysis solution has dwelled within the patient for the desired period of time, the spent dialysis solution is pumped from the patient to the drain. The heated dialysis solution is then pumped from the heater bag 124 to the patient where it dwells for a desired period of time. These steps are repeated with the dialysis solution from two of the three remaining dialysis solution bags 122. The dialysis solution from the last dialysis solution bag 122 is typically delivered to the patient and left in the patient until the subsequent PD treatment.

While the dialysis solution has been described as being pumped into the heater bag 124 from a single dialysis solution bag 122, dialysis solution can alternatively be pumped into the heater bag 124 from multiple dialysis solution bags 122. Such a technique may be advantageous, for example, where the dialysis solutions in the bags 122 have different concentrations (e.g., different dextrose concentrations) and a desired concentration for treatment is intermediate to the concentrations of the dialysis solution in two or more of the bags 122.

Figure 16:
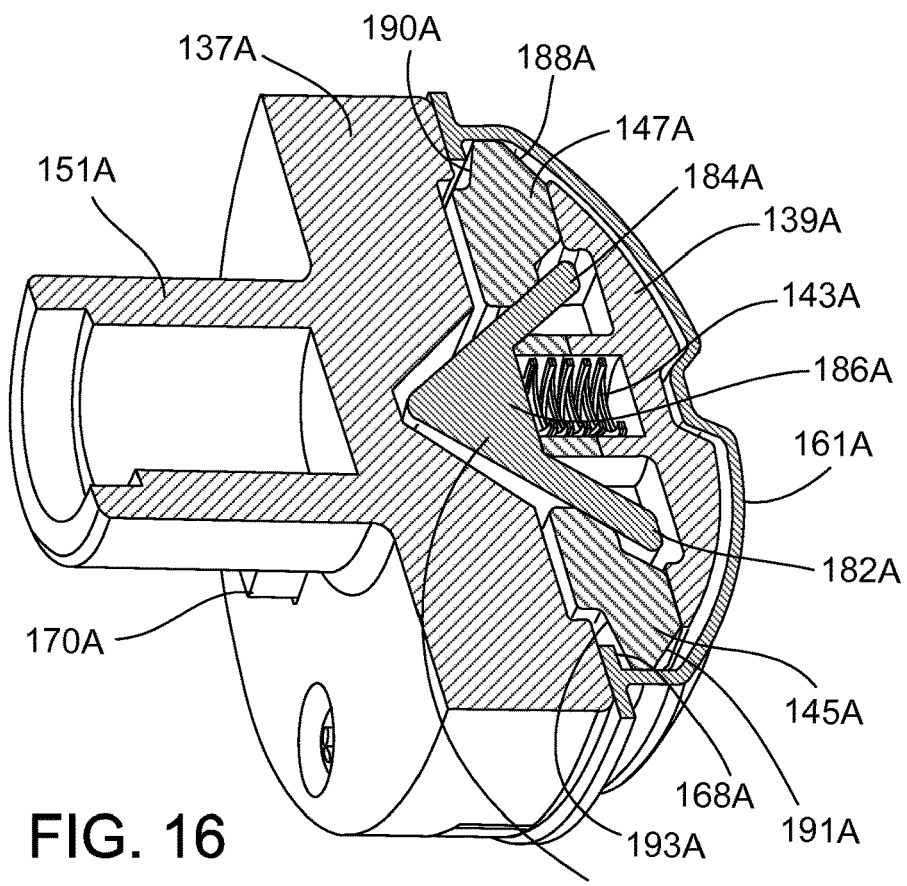
FIGS. 16 and 17 are cross-sectional views of one of the piston heads of the PD cycler of the PD system of FIG. 1 mechanically connected to one of the dome-shaped fastening members of the PD cassette of the PD system of FIG. 1, illustrating horns or projections that extend from a rear surface of the piston head to allow the piston head to be automatically disconnected from the dome-shaped fastening member of the PD cassette.
Figure 17:
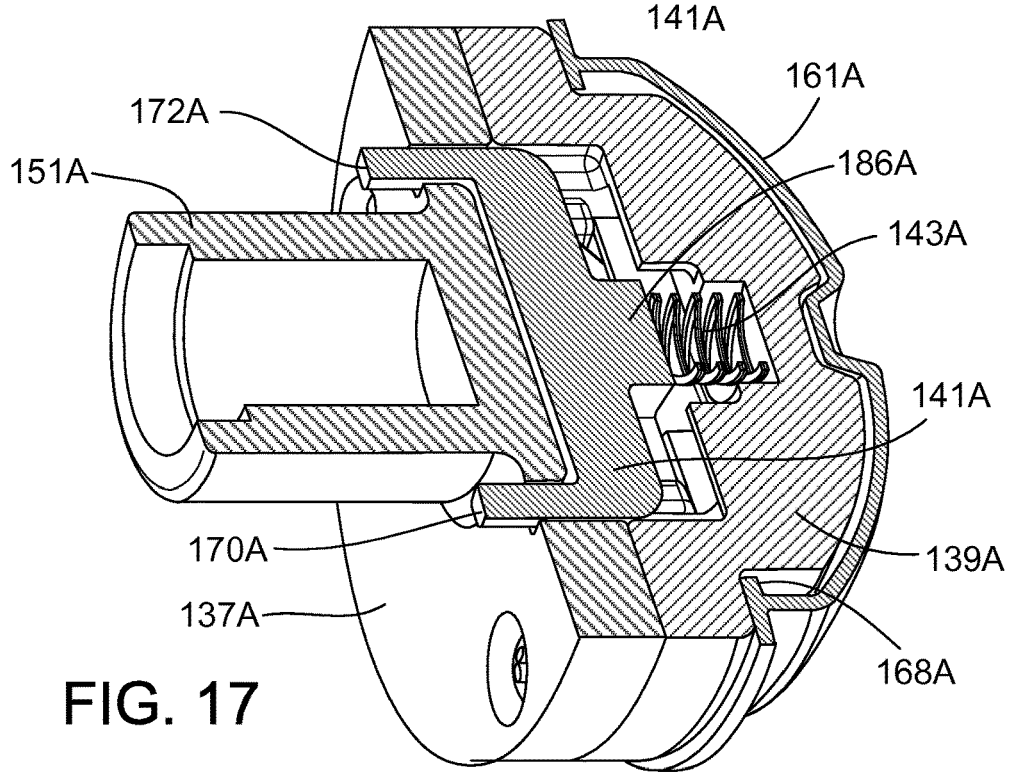

After completion of the PD treatment, the pistons 133A, 133B are retracted in a manner to disconnect the piston heads 134A, 134B from the dome-shaped members 161A, 161B of the cassette. This process will be described with reference to FIGS. 16-19. Because the piston heads 134A, 134B are substantially identical, the disconnection process will only be described in detail with respect to the piston head 134A. As shown in FIGS. 16 and 17, which are different cross-sectional views of the piston head 134A connected to the dome-shaped member 161A, the horns or projections 170A, 172A of the latch lock 141A extend rearwardly through apertures formed in the rear member 137A of the piston head 134A. The horns 170A,172A have a length such that the horns 170A, 172A extend slightly from the rear surface of the rear member 137A or are flush with the rear surface of the rear member 137A when the latch lock 141A is advanced to its fully forward position and the spring 143A is compressed.

Figure 18:
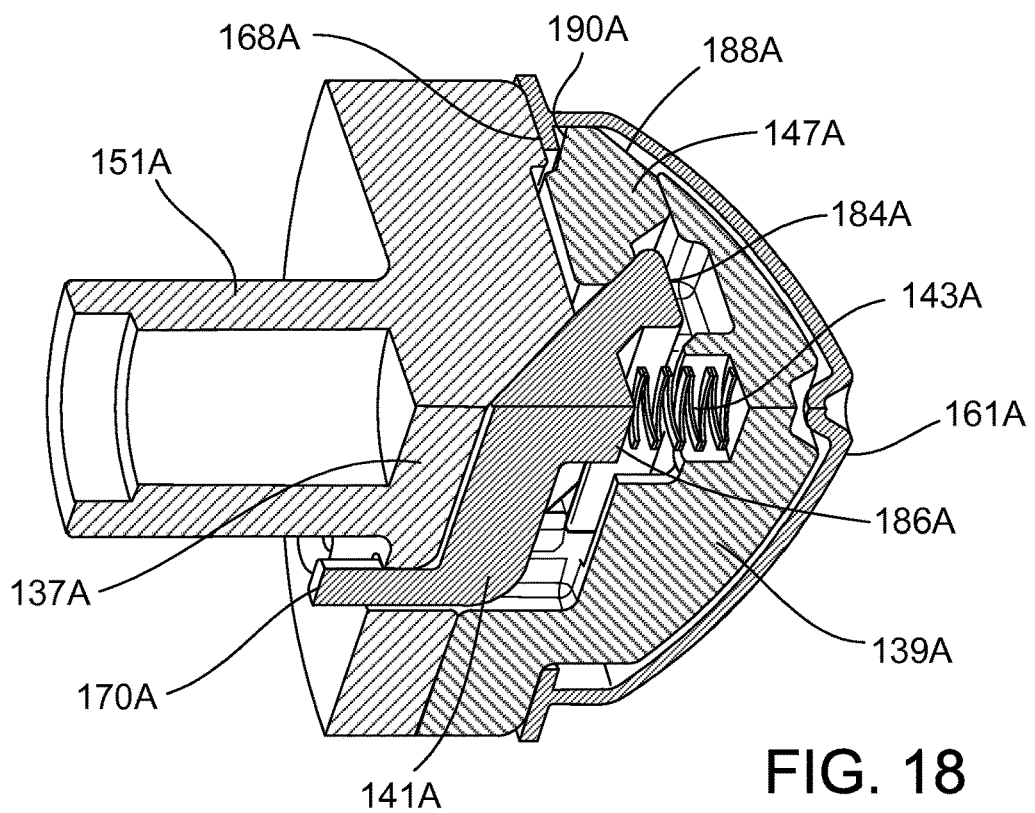
FIGS. 18 and 19 are double cross-sectional views of one of the piston heads of the PD cycler the PD system of FIG. 1 mechanically connected to one of the dome-shaped fastening members of the PD cassette of the PD system of FIG. 1, diagrammatically illustrating a process of automatically disconnecting the piston head from the dome-shaped fastening member of the PD cassette.

The horns 170A, 172A can be used to draw the sliding latches 145A, 147A radially inward to allow the piston head 134A to be disconnected from the dome-shaped member 161A of the cassette 112. FIG. 18 is a double cross-sectional view of the piston head 134A mechanically connected to the dome-shaped member 161A. As shown in FIG. 18, when the piston head 134A and the dome-shaped member 161A are mechanically connected, the horns 170A, 172A extend through the apertures of the rear member 137A and rearwardly beyond the rear surface of that member. In this position, the spring 143A of the piston head 134A is expanded and holds the latch lock 141 in its rearmost position, causing the horns 170A, 172A to protrude from the apertures of the rear member 137A.

Figure 19:
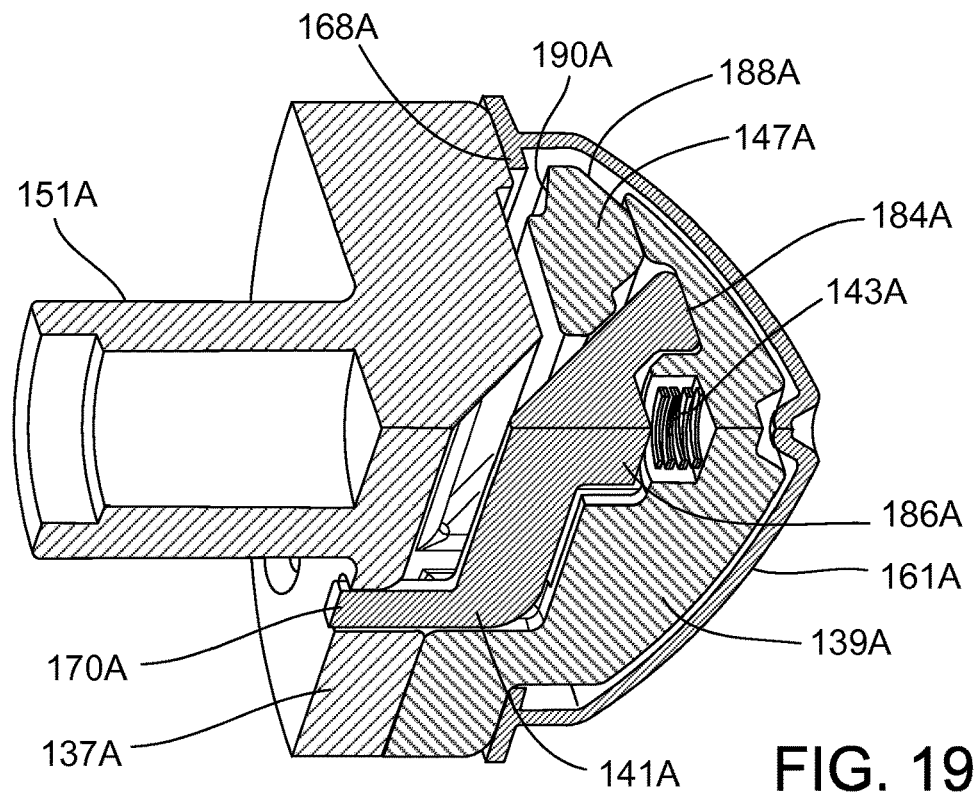

FIG. 19 is a double cross-sectional view of the piston head 134A in a configuration to be mechanically disconnected from the dome-shaped member 161A. In this configuration, the horns 170A, 172A are pushed into the apertures of the rear member 137A. As a result, the latch lock 141A is moved to its forward most position and the spring 143A is compressed.

As the piston 133A is reciprocated during treatment, the horns 170A, 172A are forwardly spaced from a vertically oriented stop or surface 174 (shown in FIGS. 15A-15F) of the PD cycler 102. As a result, the horns 170A, 172A remain in their fully rearwardly extended position throughout the pump process. However, after the treatment has been completed, the piston 133A is retracted a sufficient distance so that the horns 170A, 172A are backed into the stop or surface 174 of the PD cycler 102. Continued retraction of the piston 133A pushes the horns 170A, 172A into the apertures of the rear member 137A and causes the latch lock 141A to move forward relative to the front member 139A, thereby compressing the spring 143A, as shown in FIG. 19. As a result, the inner angled surfaces of the legs 155A, 157A of the latch lock 141A press against the adjacent, similarly angled surfaces of the sliding latches 145A, 147A, causing the sliding latches 145A, 147A to be drawn radially inwardly and disengaging the sliding latches 145A, 147A from the projection 168A (shown in FIGS. 15A-15F) of the dome-shaped member 161A. Further retraction of the piston 133A causes the piston head 134A to be backed out of the dome-shaped member 161A of the cassette 112. Alternatively or additionally, the resilience of the stretched membrane 140 can cause the membrane 140 and the dome-shaped member 161A to snap forward and out of contact with the piston head 134A as the sliding latches 145A, 147A become disengaged from the projection 168A of the dome-shaped member 161A.

After the pistons 133A, 133B have been disconnected from and backed out of the dome-shaped members 161A, 161B of the cassette 112 in the manner described above, the door 108 of the PD cycler is opened and the cassette 112 is removed from the cassette compartment 114 and discarded.

Because the PD system 100 does not require a vacuum system to draw liquid into the fluid pump chambers 138A, 138B, a substantially airtight seal between the door 108 and the cassette interface 110 is typically not required. Thus, as compared to systems including a vacuum system adapted to retract portions of the cassette membrane overlying pump chambers, the door sealing mechanism of the PD cycler 102 can be simpler and more cost effective. In addition, the reduced use of vacuum pressure relative to certain conventional cyclers can result in quieter operation.

While certain implementations have been described, other implementations are possible.

Figure 20:
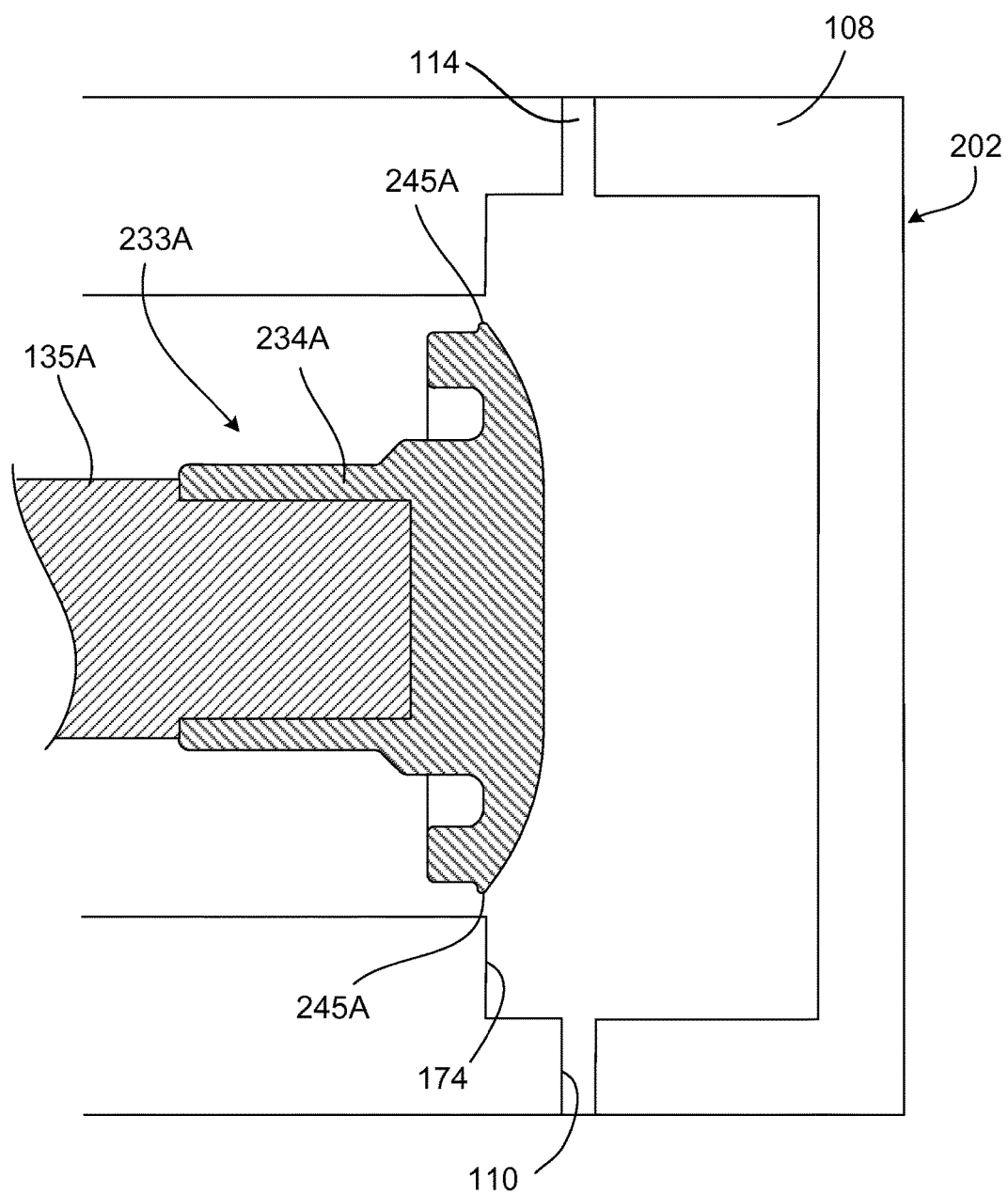
FIG. 20 is a diagrammatic cross-sectional view of another PD cycler that includes a translatable piston head with a peripheral flange that allows the piston head to be mechanically connected to a dome-shaped fastening member of a PD cassette.

While the piston heads 134A, 134B have been described as including spring-loaded latch mechanisms with sliding latches 145A, 145B that can be move radially inward and outward to allow those piston heads 134A, 134B to be mechanically connected to the dome-shaped members 161A, 161B of the cassette 112, piston heads of simpler construction that include no such sliding latches can alternatively be used in some cases. FIG. 20 illustrates a PD cycler 202 including a piston 233A that has one such type of piston head 234A connected to its piston shaft 135A. The PD cycler 202 is essentially the same as the PD cycler 102 described above except the pistons include different types of piston heads than the pistons in the PD cycler 102 described above. Like the PD cycler 102, the PD cycler 202 also includes a second piston that has a substantially identical structure and function to the piston 233A illustrated in FIG. 20 and thus will not be separately described in detail.

Still referring to FIG. 20, the piston head 234A is a unitary structure that includes a peripheral flange 245A that can be engaged with an annular projection of a dome-shaped member of a cassette in order to mechanically connect the piston head 234A to the cassette and enable a fluid pumping process of the type described above to be carried out. The rear surface of the flange 245A can be arranged at an angle of about 45 degrees to about 75 degrees (e.g., about 60 degrees) relative to the longitudinal axis of the piston. The piston head 234A can be formed using any of the materials and techniques described above with respect to the piston head 134A. Similarly, the piston head 234A can be secured to the piston shaft 135A using any of the attachment techniques discussed above for attaching the piston head 134A to the piston shaft 135A.

Figure 21C:
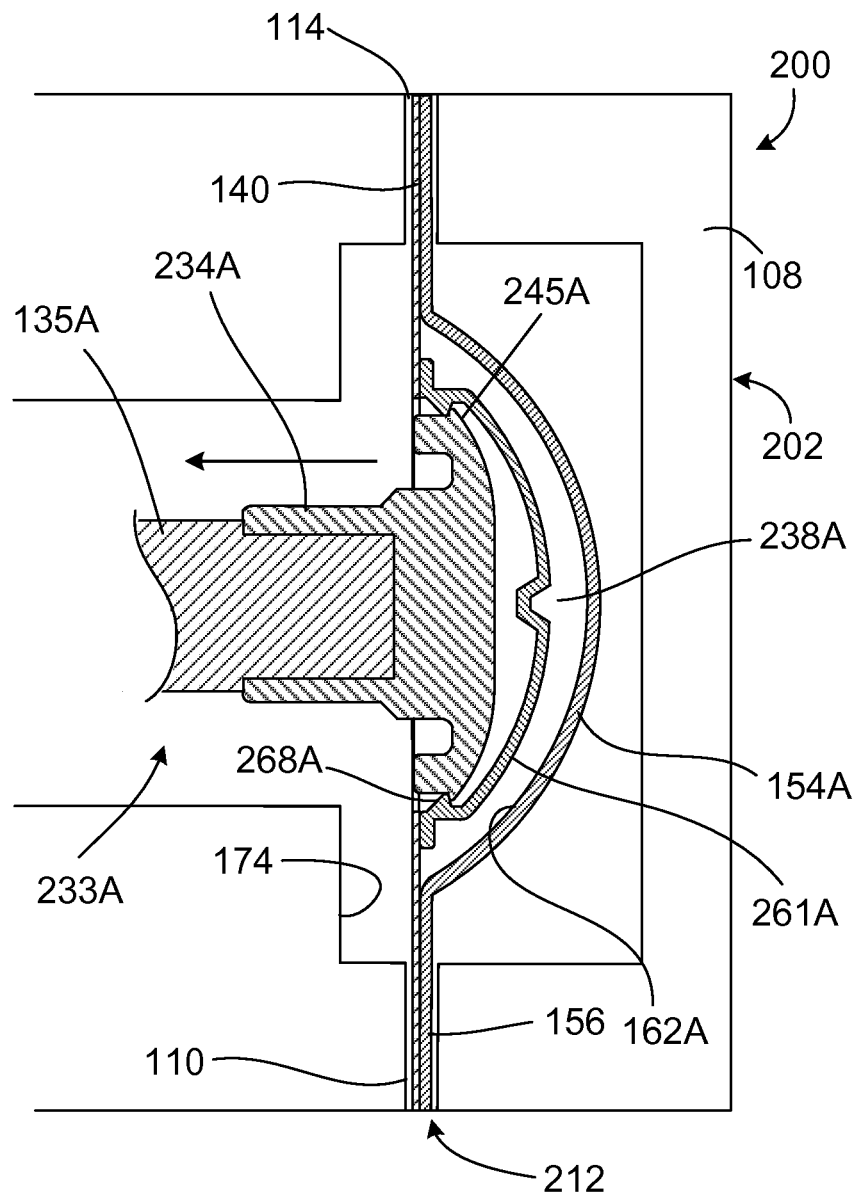

FIGS. 21A-21C are diagrammatic cross-sectional views of a PD system 200 that includes a PD cassette 212 disposed in the cassette compartment 114 of the PD cycler 202, during different phases of a pumping operation used to draw dialysis solution into a pump chamber 238A of the cassette 212 and to force dialysis solution out of the pump chamber 238A of the cassette 212. The cassette 212 is very similar to the cassette 112 described above. However, the cassette 212 includes a rigid dome-shaped member 261A that is shaped slightly differently than the dome-shaped member 161A described above. The technique for pumping solution to and from the other pump chamber of the cassette 212 is identical and thus is not separately described in detail.

As shown in FIG. 21A, once the cassette 212 has been installed within the cassette compartment 114 of the PD cycler 202, the piston 233A is advanced to initiate the process of connecting the piston head 234A of the PD cycler 202 to the dome-shaped member 261A of the cassette 212. As the piston 233A is advanced, the flange 245A of the piston head 234A contacts the lead-in chamfer or rear surface of an annular projection 268A that extends radially inward from the dome-shaped member 261A and pushes the dome-shaped member 261A into contact with the rigid base 156 of the cassette 212. The front surface of the flange 245A of the piston head 234A and the rear surface of the annular projection 268A of the dome-shaped member 261A are generally arranged to approximately mate with one another. The leading front surface of the flange 245A of the piston head 234A is typically angled rearwardly at about 45 to about 75 degrees (e.g., about 60 degrees) relative to the longitudinal axis of the piston 233A. The rear surface of the annular projection is typically angled frontwardly at about 45 to about 75 degrees (e.g., about 60 degrees) relative to the longitudinal axis of the piston 233A. Due to the geometry and rigidity of the flange 245A of the piston head 234A, advancing the piston head 234A into the dome-shaped member 261A of the cassette 212 causes the peripheral side wall of the cassette 212 from which the projection 268A extends to deflect radially outwardly, allowing the flange 245A to slide past the projection 268A. The dome-shaped member 261A of the cassette 212 is resilient so that the projection 268A snaps back into place behind the flange 245 after the flange 245 slides past the projection 268A. The engagement between the flange 245A and the projection 268A holds the piston head 234A secured to the dome-shaped member 261A of the cassette 212 to permit pumping action to be applied to the cassette 212 by the piston 233A.

As the piston head 234A is mechanically connected to the dome-shaped member 261A in the manner described above, the volume of the pump chamber 238A formed between the dome-shaped member 261A, the membrane 140 decreases due to the forward movement of the dome-shaped member 261A into the recessed region 162A of the base 156, and thus causes any fluid (e.g., priming fluid) within the pump chamber 238A to be forced out of the pump chamber 238A.

Referring to FIG. 21C, the piston 233A is then retracted to draw dialysis solution into the pump chamber 238A. Because the piston head 234A is mechanically connected to the dome-shaped member 261A and the dome-shaped member 261A is attached to the membrane 140 of the cassette 212, the retraction of the piston 233A causes the dome-shaped member 261A and the portion of the membrane 140 attached to the dome-shaped member 261A to move rearwardly. As a result, the volume of the pump chamber 238A is increased and fluid is drawn into the pump chamber 238A.

After drawing the dialysis solution into the pump chamber 238A, the dialysis solution is forced out of the pump chamber 238A by again advancing the piston 233A and decreasing the volume of the pump chamber 238A. As discussed above, this process of drawing dialysis solution into the fluid pump chamber 238A and then forcing the dialysis solution out of the fluid pump chamber 238A can be repeated until a desired volume of dialysis solution has been pumped to or from a location (e.g., to or from the patient) during a PD treatment.

To mechanically disconnect the piston head 234A from the dome-shaped member 261A after treatment, the piston 233A is retracted farther than it is retracted during treatment. This retraction causes the rear surface of the peripheral flange of the dome-shaped member 261A to contact the surface 174 of the PD cycler 202 such that the dome-shaped member 261A is prevented from moving any further in the rearward direction. The piston 233A continues to retract such that the piston head 234A slides rearwardly relative to the dome-shaped member 261A. The rear surface of the flange 245A of the piston head 234A is typically angled frontwardly at about 60 to about 80 degrees (e.g., about 70 degrees) relative to the longitudinal axis of the piston 233A. The front surface of the annular projection 268A is typically angled rearwardly at about 60 to about 80 degrees (e.g., about 70 degrees) relative to the longitudinal axis of the piston 233A. As a result of the orientation of these surfaces and the inability of the dome-shaped member 261A to move further rearwardly, the rearward motion of the piston head 234A causes the portions of the dome-shaped member 261A from which the annular projection 268A extends to deflect radially outwardly. This allows the flange 245A of the piston head 234A to slide past the annular projection 268A resulting in the piston head 234A being mechanically disconnected from the dome-shaped member 261A.

While the piston head 234A and cassette 212 have been described as being constructed so that the peripheral side walls of the cassette 212 deflect outwardly as the piston head 234A is advanced into and retracted out of the dome-shaped member 261A, they can alternatively or additionally be designed so that wall of the piston head 234A from which the flange 245A extends deflects radially inwardly to allow the flange 245A of the piston head 234A to slide past the projection 268A of the cassette 212.

While the cassette 212 and the PD cycler 202 described above are designed so that the rear surface of the peripheral flange of the dome-shaped member 261 contacts the surface 174 of the PD cycler 202 during the disconnection process, in certain implementations, the membrane 140 itself may provide sufficient resistance to rearward movement of the dome-shaped member 261A to allow the piston head 234A to be disconnected from the dome-shaped member 261A.

Figure 22:
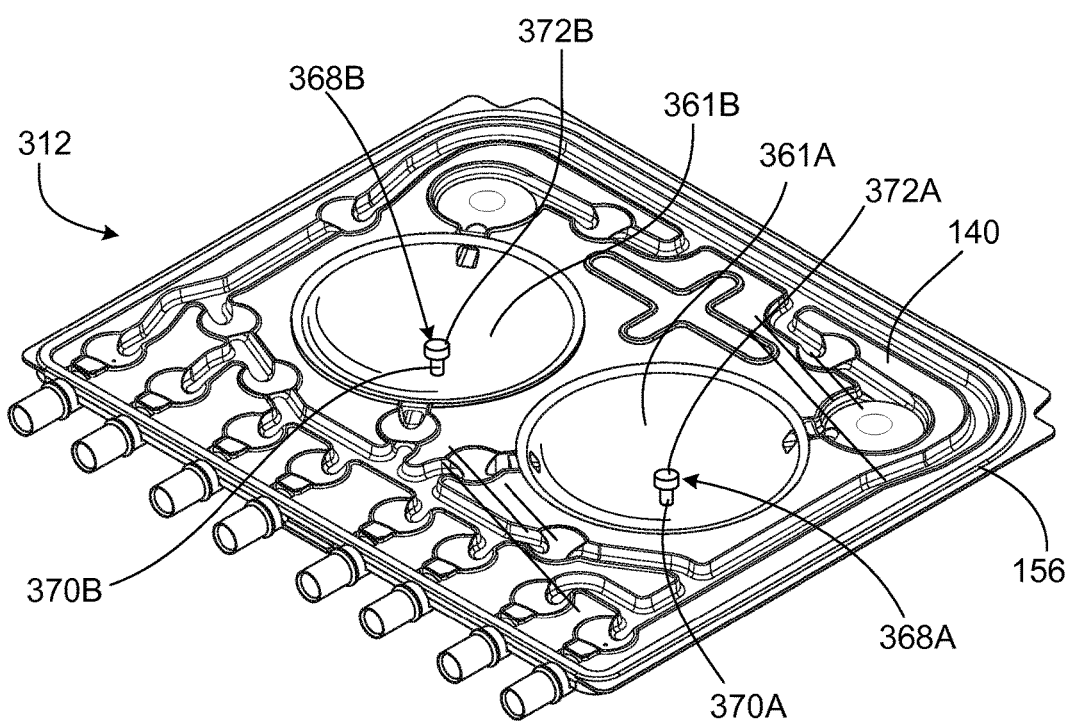
FIG. 22 is a perspective view of a PD cassette that includes dome-shaped fastening members having pegs that allow the dome-shaped fastening members to be mechanically connected to translatable piston heads of a PD cycler.

Other structures for enabling a mechanical connection between piston heads and a cassette can also be used. As shown in FIG. 22, for example, a cassette 312, which is structurally very similar to the cassette 112 described above, includes pegs 368A, 368B that extend from rigid, dome-shaped members 361A, 361B, which are disposed within the recessed regions 162A, 162B of the base 156 of the cassette 112 and are attached to the membrane 140 of the cassette 312 in the same way as the dome-shaped members 161A, 161B of the cassette 112 discussed above. Each of the pegs 368A, 368B includes a stem 370A, 370B attached to the associated dome-shaped member 361A, 361B of the cassette 312 and an enlarged head 372A, 372B attached to or integrally formed with an end of the stem 370A, 370B opposite the dome-shaped members 361A, 361B. As discussed below, the pegs 368A, 368B can engage piston heads of a PD cycler in a manner to mechanically connect the dome-shaped members 361A, 361B to the piston heads.

Figure 23:
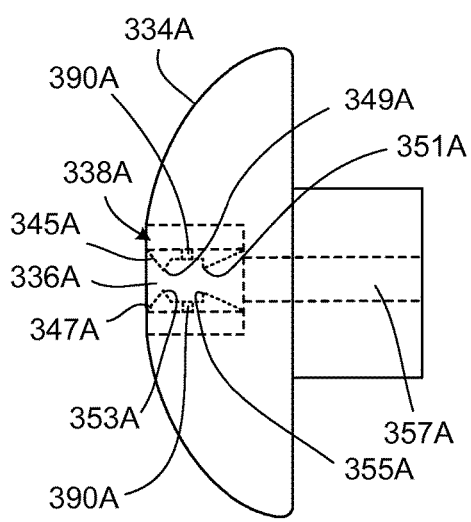
FIG. 23 is a diagrammatic side view of a translatable piston head that has a recess containing a clamp with resilient fingers that can engage the peg of one of the dome-shaped fastening members of the PD cassette of FIG. 22 to mechanically connect the piston head to the dome-shaped fastening member of the PD cassette. Internal features of the piston head are shown in dashed lines.
Figure 24:
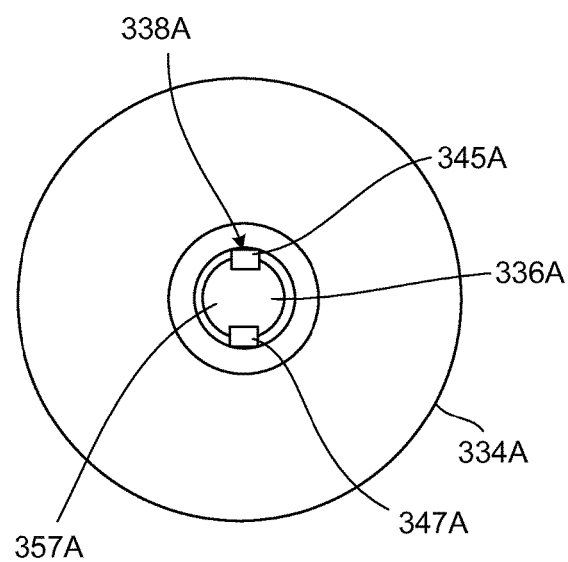
FIG. 24 is a front view of the piston head of FIG. 23.

FIGS. 23 and 24 illustrate a piston head 334A that can be secured to the piston shaft 135A of one of the PD cyclers described above and can engage the peg 368A of the cassette 312 to allow a pumping action to be produced in a pump chamber formed between a recessed region of the base 156 of the cassette 312 and the dome-shaped member 361A and membrane 140 when the piston is reciprocated. It will be appreciated that an identical piston head could be secured to the other piston shaft 135B of the PD cycler to enable a similar pumping action to be produced within the pump chamber adjacent the other dome-shaped member 361B. As shown in FIGS. 23 and 24, the piston head 334A includes a bore 336A in which a clamp mechanism 338A including two resilient spring fingers 345A, 347A is contained. Central portions of the spring fingers 345A, 347A can, for example, be attached to a radially inwardly extending annular projection 390A of the piston head 334A. Any of various attachment techniques, such as adhesive bonding, thermal welding, and/or mechanical fastening techniques, can be used to attach the spring fingers 345A, 347A to the annular projection 390A.

Still referring to FIGS. 23 and 24, the spring finger 345A includes front and rear projections 349A and 351A, respectively, that extend radially inward from a base portion of the finger 345A, and the spring finger 347A includes front and rear projections 353A and 355A, respectively, that extend radially inward from a base portion of the finger 347A. The front projections 349A, 353A have chamfers at their leading, front ends that are angled by about 15 degrees to about 75 degrees (e.g., about 30 degrees to about 60 degrees, about 45 degrees) relative to the longitudinal axis of the piston. To mechanically connect the piston head 334A to the peg 368A the piston head 334A is advanced into the dome-shaped member 361A such that front surfaces of the projections 349A, 353A of the spring fingers 345A, 347A contact the enlarged head 372A of the peg 368A. Due to the angled orientation of the font surfaces of the projections 349A, 353A, continued advancement of the piston head 334A causes the spring fingers 345A, 347A to deflect radially outward and thus spread apart as the projections 349A, 353A slide along the enlarged head 372A of the peg 368A. The spring fingers 345A, 347A spread apart a sufficient distance to allow the enlarged head 372A of the peg 368A to slide forward past the projections 349A, 353A and allow the enlarged head 372A to become fixed within a space formed between the front and rear projections of the spring fingers 345A, 347A.

The front surface of each of the rear projections 351A, 355A is substantially perpendicular to the longitudinal axis of the piston such that further advanced of the piston head 334A will not cause the spring fingers 345A, 347A to spread apart when the enlarged head 372A of the peg 368A is disposed in the space between the front and rear projections of the spring fingers 345A, 347A. With the piston head 334A and the peg 368A engaged in this manner, reciprocation of the piston head 334A causes movement of the dome-shaped member 361A and the surrounding portion of the membrane 140 and thus causes fluid to be pumped into and out of the pump chamber of the cassette 312 in the same manner as described above.

Like the front surfaces of the front projections 349A, 353A of the spring fingers 345A, 347A, the rear surfaces of the rear projections 351A, 355A are angled at about 15 degrees to about 75 degrees (e.g., about 30 degrees to about 60 degrees, about 45 degrees). An internal shaft 357A sits within an axial bore formed in the piston head 334A positioned behind the bore 336A in which the clamp mechanism 338A is contained. The internal shaft 357A is fixed to the housing of the PD cycler such that the piston head 334A moves relative to the shaft 357A as the piston head 334A reciprocates. To disconnect the piston head 334A from the peg 368A after treatment, the piston head 334A is retracted into the PD cycler a sufficient distance so that the shaft 357A contacts the rear surfaces of the rear projections 351A, 355A of the spring fingers 345A, 347A. This contact, due to the angled orientation of the rear surfaces of the rear projections 351A, 355A, causes the spring fingers 345A, 347A to spread apart. Further retraction of the piston head 334A causes the front projections 349A, 353A to move back beyond the peg 368A.

Figure 25:
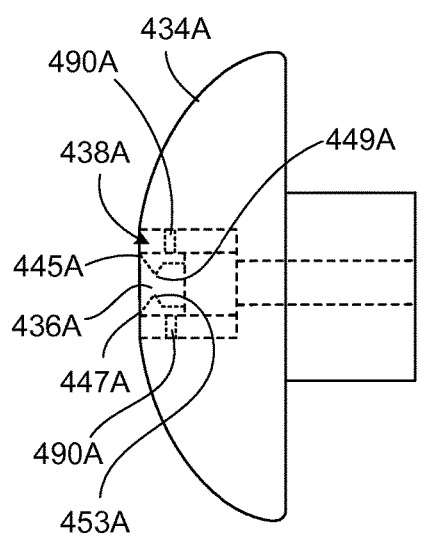
FIG. 25 is a diagrammatic side view of a translatable piston head that has a recess containing a clamp with resilient fingers of a slightly different configuration for engaging the peg of one of the dome-shaped fastening members of the PD cassette of FIG. 22 to mechanically connect the piston head to the dome-shaped fastening member of the PD cassette. Internal features of the piston head are shown in dashed lines.
Figure 26:
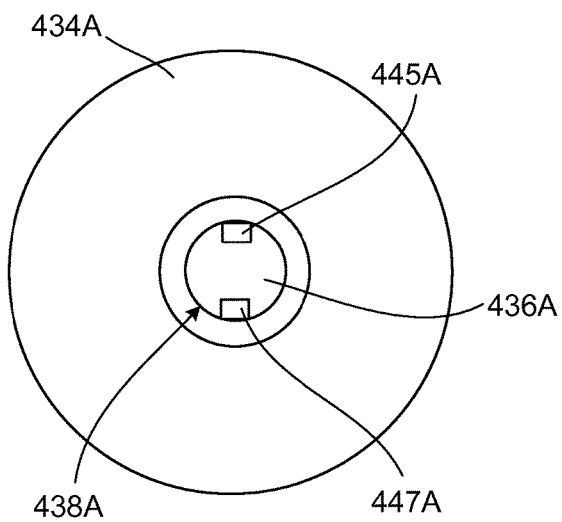
FIG. 26 is a front view of the piston head of FIG. 25.

FIGS. 25 and 26 illustrate a slightly different piston head 434A that can be secured to the piston shaft 135A of one of the PD cyclers described above and can engage the peg 368A of the cassette 312 to allow a pumping action to be produced in a pump chamber formed between a recessed region of the base 156 of the cassette 312 and the dome-shaped member 361A and membrane 140 when the piston is reciprocated. As shown in FIGS. 25 and 26, the piston head 434A includes a bore 436A in which a clamp mechanism 438A including two resilient spring fingers 445A, 447A is contained. Central portions of the spring fingers 445A, 447A are attached to a radially inwardly extending annular projection 490 of the piston head 434A. Any of various attachment techniques, such as adhesive bonding, thermal welding, and/or mechanical fastening techniques, can be used to attach the spring fingers 445A, 447A to the annular projection 490A.

Still referring to FIGS. 25 and 26, the spring fingers 445A, 447A include projections 449A, 453A that extend radially inward from base portions of the fingers 445A, 447A. The projections 449A, 453A have chamfers at their leading, front ends and their trailing, rear ends that are angled in opposite directions by about 15 degrees to about 75 degrees (e.g., about 30 degrees to about 60 degrees, about 45 degrees) relative to the longitudinal axis of the piston. The piston head 434A is mechanically connected to the cassette 312 in much the same way as the piston head 334A described above. In particular, the piston head 434A is advanced into the dome-shaped member 361A such that front surfaces of the projections 449A, 453A of the spring fingers 445A, 447A contact the enlarged head 372A of the peg 368A and, due to the angled orientation of the font surfaces of the projections 449A, 453A, cause the spring fingers 445A, 447A to deflect radially outward. The spring fingers 445A, 447A spread apart a sufficient distance to allow the enlarged head 372A of the peg 368A to slide forward past the projections 449A, 453A and into a space formed between the spring fingers 445A, 447A behind the projections 449A, 453A.

To disconnect the piston head 434A from the peg 368A after treatment, the piston head 434A is retracted into the PD cycler. As the piston head 434A is retracted, a point is reached at which the resistance of the membrane 140 pulling on the dome-shaped member 361A is greater than the force required to spread the fingers 445A, 447A apart. At this point, continued retraction of the piston head 434A causes the chamfered rear surfaces of the projections 449A, 453A to slide axially along the enlarged head 372A of the peg 368A of the cassette 312 of the spring fingers 445A, 447A, causing the spring fingers 445A, 447A to spread apart thereby allowing the peg 368A to be released from the space behind the projections 449A, 453A of the fingers 445A, 447A.

While the cassette interface 110 of the PD cycler 102 has been described as including locating pins 148 that help to ensure that the dome-shaped members of the cassette are aligned with the pistons 133A, 133B when the cassette is positioned in the cassette compartment 114, other structures or techniques can be used to ensure this alignment. In some implementations, for example, the cassette is placed against the door of the PD cycler with the hollow projections of the cassette disposed in recesses of the PD cycler's door, and the cassette is held in this position by retainer clips attached to the door. Upon closing the door, the pistons of the PD cycler align with the dome-shaped members of the cassette.

While the door 108 of each of the PD cyclers above has been described as including an inflatable pad that, when inflated, can press the cassette against the cassette interface, the inflatable pad can alternatively be positioned behind the cassette interface such that the cassette interface can be moved toward the door 108 to compress the cassette therebetween. Similarly, as an alternative to an inflatable pad, any of various mechanisms that can be operated to move a surface of the door 108 toward the cassette interface or vice versa can be used.

While the door 108 of the PD cyclers described above are shown as being positioned on a front face of the PD cyclers, the doors can alternatively be positioned at various other locations on the PD cyclers. For example, the doors could be positioned on a top face of the PD cycler such that the cassette is slid into the cassette compartment in a substantially horizontal orientation instead of a substantially vertical orientation. In some implementations, the door and the cassette interface of the PD cycler are positioned at an angle of about 10 to about 35 degrees to vertical when the PD cycler is rested on a horizontal surface. It has been found that this configuration makes it easier for the user to load the cassette into the cassette compartment.

While the cassettes discussed above have two pump chambers, the cassettes can alternatively have more or fewer than two pump chambers.

While each of the pump chambers of the cassettes described above has been described as including a fluid inlet port and a fluid outlet port, in certain implementations, the pump chambers include a single port that is used as both an inlet and an outlet. In such implementations, the inflatable valve members of the PD cycler that act on the valve portions of the cassettes would be activated and deactivated in a slightly different sequence to allow fluid to be drawn into the pump chamber from a desired location and then to be forced out of the pump chamber to a desired location.

While certain PD cyclers above have been described as including a touch screen and associated buttons, the PD cyclers can alternatively or additionally include other types of screens and user data entry systems. In certain implementations, for example, the cycler includes a display screen with buttons (e.g., feather touch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

While the mechanically connectable piston heads and cassettes described above have been described as being part of PD systems, these types of piston heads and cassettes can be used in any of various other types of medical fluid pumping systems. Other examples of medical fluid pumping systems in which the piston heads and cassettes described herein can be used include hemodialysis systems, blood perfusion systems, and intravenous infusion systems.

Similarly, while many of the systems above have been described as being used to pump dialysis solution, other types of dialysis fluids can be pumped through the cassettes. As an example, in the case of cassettes used with hemodialysis machines, blood can be pumped through the cassettes. In addition, priming solutions, such as saline, can similarly be pumped through cassettes using the various different systems and techniques described above. Similarly, as an alternative to dialysis fluids, any of various other types of medical fluids can be pumped through the above-described cassettes depending on the type of medical fluid pumping machines with which the cassettes are used.

What is claimed is:

1. A medical fluid pumping machine comprising:
a piston head that can be linearly displaced, the piston head comprising a latch secured to a body portion of the piston head, the latch slidable relative to the body portion between a retracted position and an extended position in which an engagement surface of the latch is positioned radially outward of a perimeter of the body portion, the piston head being configured to be disposed within a recess defined by a fastening member of a medical fluid cassette, and the engagement surface of the latch being configured to engage an engagement surface of the fastening member of the medical fluid cassette when the piston head is disposed in the recess such that, when the piston head is disposed in the recess and is moved linearly away from a base of the cassette with the latch in the extended position, the engagement surface of the latch of the piston head is engaged with the engagement surface of the fastening member and pulls the fastening member and a flexible membrane to which the fastening member is attached away from the base to increase a volume of a fluid pump chamber defined in the cassette between the flexible membrane and the base.

2. The medical fluid pumping machine of claim 1, wherein the latch of the piston head comprises a contact surface that extends radially beyond the perimeter of the body portion when the latch is in the extended position.

3. The medical fluid pumping machine of claim 2, wherein the latch of the piston head is configured to move radially inwardly when the piston head is inserted into the recess of the fastening member.

4. The medical fluid pumping machine of claim 1, wherein the latch of the piston head is radially movable relative to the body portion of the piston head.

5. The medical fluid pumping machine of claim 1, wherein the engagement surface of the latch is configured to be positioned radially inward of the perimeter of the body portion when the latch is in the retracted position.

6. The medical fluid pumping machine of claim 1, wherein the piston head is constructed to become mechanically connected to the fastening member when the piston head is moved toward the base of the cassette and to become disconnected from the fastening member when the piston head is moved away from the base of the cassette.

7. The medical fluid pumping machine of claim 1, wherein the medical fluid pumping machine is a dialysis machine.

8. The medical fluid pumping machine of claim 1, wherein the medical fluid pumping machine defines a cassette compartment configured to receive the cassette.

9. The medical fluid pumping machine of claim 8, wherein the cassette compartment is defined by a door and a face of the medical fluid pumping machine.

10. The medical fluid pumping machine of claim 1, wherein the body portion comprises front and rear members, and the latch is positioned in a space defined between the front and rear members.

11. The medical fluid pumping machine of claim 10, wherein the piston head further comprises a latch lock having a first angled surface that sits adjacent an associated first angled surface of the latch such that radially inward movement of the latch causes axial movement of the latch lock in a first axial direction.

12. The medical fluid pumping machine of claim 11, wherein the piston head further comprises a spring disposed between the latch lock and the front member to resist the axial movement of the latch lock in the first axial direction.

13. The medical fluid pumping machine of claim 12, wherein the latch and the latch lock are configured such that when a force applied to the latch to move the latch radially inwardly and to move the latch lock axially is released, the spring expands and moves the latch lock in a second axial direction opposite the first axial direction and causes the latch to move radially outwardly.

14. The medical fluid pumping machine of claim 1, further comprising a latch lock configured to move axially in a first axial direction when the latch moves radially inward.

15. A medical fluid pumping machine comprising:
a piston head that can be linearly displaced, the piston head comprising
a latch secured to a body portion of the piston head, the latch having an extended position in which an engagement surface of the latch is positioned radially outward of a perimeter of the body portion, the piston head being configured to be disposed within a recess defined by a fastening member of a medical fluid cassette, and the engagement surface of the latch being configured to engage an engagement surface of the fastening member of the medical fluid cassette when the piston head is disposed in the recess such that, when the piston head is disposed in the recess and is moved linearly away from a base of the cassette with the latch in the extended position, the engagement surface of the latch of the piston head is engaged with the engagement surface of the fastening member and pulls the fastening member and a flexible membrane to which the fastening member is attached away from the base to increase a volume of a fluid pump chamber defined in the cassette between the flexible membrane and the base, and a latch lock having a first angled surface that sits adjacent an associated first angled surface of the latch such that radially inward movement of the latch causes axial movement of the latch lock in a first axial direction.

16. The medical fluid pumping machine of claim 15, wherein the latch of the piston head comprises a contact surface that extends radially beyond the perimeter of the body portion when the latch is in the extended position.

17. The medical fluid pumping machine of claim 16, wherein the latch of the piston head is configured to move radially inwardly when the piston head is inserted into the recess of the fastening member.

18. The medical fluid pumping machine of claim 15, wherein the latch of the piston head is radially movable relative to the body portion of the piston head.

19. The medical fluid pumping machine of claim 15, wherein the latch has a retracted position in which the engagement surface of the latch positioned radially inward of the perimeter of the body portion.

20. The medical fluid pumping machine of claim 15, wherein the piston head is constructed to become mechanically connected to the fastening member when the piston head is moved toward the base of the cassette and to become disconnected from the fastening member when the piston head is moved away from the base of the cassette.

* * * * *

UNITED STATES PATENT AND TRADEMARK OFFICE
CERTIFICATE OF CORRECTION

| | |
|---|---|
| PATENT NO. | : 10,143,791 B2 |
| APPLICATION NO. | : 14/870926 |
| DATED | : December 4, 2018 |
| INVENTOR(S) | : Sean Farrell et al. |

Page 1 of 1

It is certified that error appears in the above-identified patent and that said Letters Patent is hereby corrected as shown below:

In the Claims

<u>Claim 13</u>
Column 28, Line 38, delete "that" and insert --that,--.

Signed and Sealed this
Twenty-second Day of January, 2019

Andrei Iancu
*Director of the United States Patent and Trademark Office*